US011248029B2

(12) United States Patent
Muro et al.

(10) Patent No.: US 11,248,029 B2
(45) Date of Patent: Feb. 15, 2022

(54) ICAM-1 TARGETED FUSION ENZYMES

(71) Applicant: University of Maryland, College Park, College Park, MD (US)

(72) Inventors: Silvia Muro, Gaithersburgh, MD (US); Jing Chen, Nanjing (CN); Melani Solomon, Laurel, MD (US); Kevin Gray, Washington, DC (US)

(73) Assignee: University of Maryland, College Park, College Park, MD (US)

( * ) Notice: Subject to any disclaimer, the term of this patent is extended or adjusted under 35 U.S.C. 154(b) by 0 days.

(21) Appl. No.: 16/951,774

(22) Filed: Nov. 18, 2020

(65) Prior Publication Data

US 2021/0147495 A1 May 20, 2021

Related U.S. Application Data

(60) Provisional application No. 62/936,988, filed on Nov. 18, 2019.

(51) Int. Cl.

| | |
|---|---|
| ***C07K 14/47*** | (2006.01) |
| ***C12N 9/16*** | (2006.01) |
| ***C12N 9/40*** | (2006.01) |
| ***C12N 9/24*** | (2006.01) |
| ***C07K 14/705*** | (2006.01) |

(52) U.S. Cl.

CPC ................ *C07K 14/47* (2013.01); *C12N 9/16* (2013.01); *C12N 9/2402* (2013.01); *C12N 9/2465* (2013.01); *C12Y 302/01022* (2013.01); *C12Y 302/01045* (2013.01); *C07K 2319/055* (2013.01); *C07K 2319/21* (2013.01); *C07K 2319/33* (2013.01); *C07K 2319/50* (2013.01)

(58) Field of Classification Search

None

See application file for complete search history.

(56) References Cited

U.S. PATENT DOCUMENTS 8,889,127 B2 11/2014 Muro Galindo et al.
8,926,946 B2 1/2015 Muro Galindo et al.

OTHER PUBLICATIONS

Garnacho et al. (ICAM-1 targeting, intracellular trafficking, and functional activity of polymer nanocarriers coated with a fibrinogen-derived peptide for lysosomal enzyme replacement, Journal of Drug Targeting, 2017, vol. 25, No. 9-10, 786-795).*

Muro, Silvia, et al., Lysosomal enzyme delivery by ICAM-1-targeted nanocarriers bypassing glycosylation- and clathrin-dependent endocytosis, Molecular Therapy, Jan. 2006, pp. 135-141, vol. 13, No. 1.

Garnacho, Carmen, et al., Delivery of acid sphingomyelinase in normal and Niemann-Pick disease mice using ICAM-1-targeted polymer nanocarriers, Journal of Pharmacology and Experimental Therapeutics, Feb. 20, 2008, pp. 400-408, vol. 325, No. 2.

Hsu, Janet, et al., Enhanced endothelial delivery and biochemical effects of α-galactosidase by ICAM-1-targeted nanocarriers for Fabry disease, Journal of Controlled Release, Nov. 1, 2010, pp. 323-331, vol. 149, No. 3.

Muro Silivia, et al., Design of ICAM-1-targeting strategies for brain delivery of lysosomal therapies, Molecular Genetics and Metabolism, Feb. 2011, p. S31, vol. 102.

Hsu, Janet, et al., Enhanced delivery of α-glucosidase for Pompe disease by ICAM-1-targeted nanocarriers: comparative performance of a strategy for three distinct lysosomal storage disorders, Nanomedicine: Nanotechnology, Biology, and Medicine, Jul. 2012, pp. 731-739, vol. 8, No. 5.

Garnacho, Carmen, et al., A Fibrinogen-Derived Peptide Provides Intercellular Adhesion Molecule-1-Specific Targeting and Intraendothelial Transport of Polymer Nanocarriers in Human Cell Cultures and Mice, Journal of Pharmacology and Experimental Therapeutics, Mar. 2012, pp. 638-647, vol. 340, No. 3.

Papademetriod, Jason, et al., Comparative binding, endocytosis, and biodistribution of antibodies and antibody-coated carriers for targeted delivery of lysosomal enzymes to ICAM-1 versus transferrin receptor, Journal of Inherited Metabolic Disease, Sep. 12, 2012, pp. 467-477, vol. 36.

Hsu, Janet, et al., Enhancing Biodistribution of Therapeutic Enzymes In Vivo by Modulating Surface Coating and Concentration of ICAM-1-Targeted Nanocarriers, Journal of Biomedical Nanotechnology, Feb. 2014, pp. 345-354, vol. 10, No. 2.

Serrano, Daniel, et al., A fibrinogen-derived peptide induces clathrin- and caveolaeindependent endocytosis in endothelial cells, Federation of American Societies for Experimental Biology, Apr. 1, 2012, p. 605.3 (2 pages), vol. 26, No. S1.

(Continued)

*Primary Examiner* — Suzanne M Noakes
*Assistant Examiner* — Jae W Lee
(74) *Attorney, Agent, or Firm* — Hodgson Russ LLP

(57) ABSTRACT

Proteins, nucleic acids encoding the proteins, compositions comprising the proteins, and methods are provided. The proteins have the ability to be self-targeted to ICAM-1 and, if desired, enzymatically-released at acidic pH. The ICAM-1-targeting peptides are provided as single copies or multiples repeats, and can be separated by linkers from the enzyme segment, from which the ICAM-1 targeting peptides can be released, if desired, at acidic pH. These fusion proteins enhance the activity of the enzyme segment within or liberated from the fusion protein, and provide increased recognition and targeting of diseased organs, transport from the bloodstream across the endothelium into said diseased organ, and intracellular uptake and lysosomal trafficking by cells in them, both in peripheral tissues and the central nervous system. Representative nucleotide and amino acid sequences of these fusion proteins, as well as in vitro, cellular, and in vivo animal data are provided. The described proteins can be used as a protein therapy, a gene therapy, or an implanted cell therapy.

13 Claims, 21 Drawing Sheets
(10 of 21 Drawing Sheet(s) Filed in Color)
Specification includes a Sequence Listing.

(56) References Cited

OTHER PUBLICATIONS

Hsu, Janet, et al., Enhanced Kidney and Heart Delivery of α-Galactosidase by Modulating Enzyme Load and Carrier Bulk-Concentration of ICAM-1-Targeted Nanocarriers, Molecular Genetics and Metabolism, Feb. 2012, p. S37, vol. 105, No. 2.

Hsu, Janet, et al., Specific Binding, Uptake, and Transport of ICAM-1-Targeted Nanocarriers Across Endothelial and Subendothelial Cell Components of the Blood-Brain Barrier, Pharmaceutical Research, Feb. 21, 2014, pp. 1855-1866, vol. 31.

Rappaport, Jeff, et al., Clathrin-Mediated Endocytosis Is Impaired in Type A-B Niemann-Pick Disease Model Cells and Can Be Restored by ICAM-1-Mediated Enzyme Replacement, Molecular Pharmaceutics, Jun. 20, 2014, pp. 2887-2895, vol. 11, No. 8.

Hsu, Janet, et al., Targeting, Endocytosis, and Lysosomal Delivery of Active Enzymes to Model Human Neurons by ICAM-1-Targeted Nanocarriers, Pharmaceutical Research, Oct. 16, 2014, pp. 1264-1278, vol. 32.

Rappaport, Jeff, et al., Altered Clathrin-Independent Endocytosis in Type A Niemann-Pick Disease Cells and Rescue by ICAM-1-Targeted Enzyme Delivery, Molecular Pharmaceutics, Apr. 7, 2015, pp. 1366-1376, vol. 12, No. 5.

Rappaport, Jeff, et al., A Comparative Study on the Alterations of Endocytic Pathways in Multiple Lysosomal Storage Disorders, Molecular Pharmaceutics, Dec. 24, 2015, pp. 357-368, vol. 13, No. 2.

Ghaffarian, Rasa, et al., Intra- and trans-cellular delivery of enzymes by direct conjugation with non-multivalent anti-ICAM molecules, Journal of Controlled Release, Jul. 27, 2016, pp. 221-230, vol. 238.

Manthe, Rachel L., et al., ICAM-1-targeted nanocarriers attenuate endothelial release of soluble ICAM-1, an inflammatory regulator, Bioengineering and Translational Medicine, Dec. 20, 2016, pp. 109-119, vol. 2, No. 1.

Garnacho, Carmen, et al., Enhanced Delivery and Effects of Acid Sphingomyelinase by ICAM-1-Targeted Nanocarriers in Type B Niemann-Pick Disease Mice, Molecular Therapy, Jul. 5, 2017, pp. 1686-1696, vol. 25, No. 7.

Garnacho, Carmen, et al., ICAM-1 targeting, intracellular trafficking, and functional activity of polymer nanocarriers coated with a fibrinogen-derived peptide for lysosomal enzyme replacement, Journal of Drug Targeting, Jul. 14, 2017, pp. 786-795, vol. 25, No. 9-10.

Serrano, Daniel, et al., Endothelial cell adhesion molecules and drug delivery applications, Mechanobiology of the Endothelium, Chapter 9, 2014, 53 pages, CRC press, Boca Raton, USA.

Muro, Silvia, Strategies for delivery of therapeutics into the central nervous system for treatment of lysosomal storage disorders, Drug Delivery and Translational Research, May 31, 2012, pp. 169-186, vol. 2.

Solomon, Melani, et al., Lysosomal enzyme replacement therapies: Historical development, clinical outcomes, and future perspectives, Advanced Drug Delivery Reviews, May 11, 2017, pp. 109-134, vol. 118.

Kelly, Jessica M., et al., Emerging therapies for neuropathic lysosomal storage disorders, Progress in Neurobiology, Oct. 8, 2016, pp. 166-180, vol. 152.

Futerman, Anthony H., et al., The cell biology of lysosomal storage disorders, Nature Reviews Molecular Cell Biology, Jul. 1, 2004, pp. 554-565, vol. 5.

Schuchman, E. H., The pathogenesis and treatment of acid sphingomyelinase-deficient Niemann-Pick disease, Journal of Inherited Metabolic Disease, Jul. 12, 2007, pp. 654-663, vol. 30, No. 5.

Germain, Dominique P., et al, Fabry disease, Orphanet Journal of Rare Diseases, Nov. 22, 2010, 49 pages, vol. 5, Article 30.

Mistry, Pramod K., et al, Gaucher disease: Progress and ongoing challenges, Molecular Genetics and Metabolism, Nov. 17, 2016, pp. 8-21, vol. 120, No. 1-2.

* cited by examiner

A.

| | Units/mg | | |
|---|---|---|---|
| Reaction Condition | Neutral pH No cathepsinB | Acidic pH No cathepsinB | Acidic pH + cathepsinB |
| CHO3E7- ASM control (E) | 0.8 | 4.6 | 4.8 |
| CHO3E7- Fusion B | 0.9 | 5.7 | 8.8 |
| CHO3E7- Fusion C | 1.0 | 6.5 | 7.7 |
| CHO3E7- Fusion D | 0.9 | 6.0 | 7.6 |
| 293Hek- Fusion B | 0.9 | 5.8 | |
| Expi-CHO-S- Fusion B | 1.0 | 6.3 | 8.2 |
| CHO3E7- EK cleaved Fusion B | 1.5 | 7.2 | 10.6 |
| Expi-CHO-S- EK cleaved Fusion B | 1.5 | 7.3 | 10.5 |

B.

C.

D.

$$LR = \frac{\% \frac{ID}{g} tissue}{\% \frac{ID}{g} blood}$$

$$LR = \frac{\% \frac{ID}{g}\, tissue}{\% \frac{ID}{g}\, blood}$$

a=Hemoglobin Concentration Distribution width, b=Red blood cells distribution width, c=Cellular Hemoglobin Concentration Mean, d=Mean Corpuscular Hemoglobin (Hb) concentration

B.

C.

D.

| Clinical sign | Score | |
|---|---|---|
| | Control | Fusion treated |
| $ Grooming | 0 | 0 |
| # Activity | 0 | 0 |

$ 0=normal, 1= lack of grooming, 2=rough coat, 3= very rough coat
0=normal, 1= Minor changes, 2= Inactive, 3= Unresponsive

ICAM-1 TARGETED FUSION ENZYMES

CROSS-REFERENCE TO RELATED APPLICATIONS

This application claims priority to U.S. provisional patent application No. 62/936,988, filed Nov. 18, 2019, the entire disclosure of which is incorporated herein by reference.

SEQUENCE LISTING

The instant application contains a Sequence Listing which has been submitted electronically in ASCII format and is hereby incorporated by reference in its entirety. Said ASCII file, created on Nov. 30, 2020, is named Muro_UMD_NPA_ST25_revised.txt and is 95,365 bytes in size.

FIELD

The present disclosure relates generally to compositions and methods for treating lysosomal storage diseases (LSDs) and other diseases where lysosomal enzyme activities are beneficial.

BACKGROUND

LSDs are caused by defects in one or more hydrolytic enzymes of lysosomes in cells that digest biomacromolecules for cellular housekeeping. Lack of this function results in unwanted build-up of these molecules in cells and depending on the enzyme affected, specific substrate processing is impaired, and severity ranges from life-long debilitation to death. Supplementing defective enzymes by enzyme replacement therapy (ERT) is the most accepted treatment and a "universal" approach at present. However, there is an ongoing need for compositions and methods for use as ERT treatments. In addition, the activity of these lysosomal enzymes is also applicable to the treatment of other maladies. For instance, ceramide, the product of the activity of acid sphingomyelinase which is deficient in the LSD called types A and B Niemann-Pick disease, can induce cellular apoptosis when in excess. Hence, ERT methods and compositions for treatment of types A and B Niemann-Pick disease can also be used for cancer treatment. Similarly, mutations and defects in lysosomal enzyme glucocerebrosidase, which is deficient in the LSD called Gaucher disease, constitute a main hallmark in Parkinson's disease. It has been shown that increased activity of this enzyme improves the outcome of Parkinson's in animal models. Hence, ERT methods and compositions for treatment Gaucher disease can also be used for treatment of Parkinson's, but to date there remains an ongoing need for improved compositions and methods for prophylaxis and/or treatment of such ERT conditions. The present disclosure is pertinent to these needs.

BRIEF SUMMARY

The present disclosure provides compositions and methods that are useful for treating a variety of LSDs. The compositions include fusion proteins, for use in treating one or more LSDs, or additional diseases which may benefit from these enzyme activities.

Data presented in this disclosure demonstrate that, unexpectedly and unpredictably, the described fusion proteins exhibit enhanced enzymatic activity in conditions mimicking lysosomes, such as lysosomal pH, both as such fusion proteins and also after the enzyme segment has been liberated from the fusion protein, relative to the same enzyme that is not provided in a fusion protein context. This enhanced activity cannot be explained solely by the precise enzyme segment sequence used to form the fusion protein, because when the same enzyme segment is used to produce an enzyme without fusion to ICAM-1 targeting peptides, its activity is lower than that of the fusion protein or the enzymatic segment liberated from the fusion protein.

Data presented in this disclosure also support the use of the described fusion proteins for improved effects in cellular models and in mouse organs, including but not necessarily limited to the lung and brain, the latter of which no previously described enzyme replacement therapy has been able to access in a therapeutic dose. With respect to the fusion proteins provided by the disclosure, they generally comprise: i) one or more intercellular adhesion molecule-1 (ICAM-1) targeting segments; ii) an enzyme segment that is catalytically active at the pH of a lysosome; iii) optionally a first protease cleavage sequence segment between i) and ii), and optionally, one or more of: iv) a secretion signal; v) a protein purification tag; and vi) a second protease cleavage signal, such as for use in protein purification of iv) and v) from the final product. The form and content of the fusion protein can be changed depending on, for example, its method of delivery.

In embodiments, the ICAM-1 targeting segment comprises amino acid SEQ ID NO 1 NNQKIVNIKEKVAQIEA (2γ3) or respective nucleotide sequence, which are comprised in fusion proteins containing amino acid or nucleotide SEQ ID NO 2, 3, 4, 5, 7, 8, 10, 11, 13, 14, 15, 16, 18, 19, 21, 22. This is in contrast to non-targeted enzyme sequences shown as control in some embodiments, such as amino acid or nucleotide SEQ ID NO 6, 9, 12, 17, 20, and 23. In both cases, that of fusion proteins or control non-targeted enzymes, nucleotide sequences provided include codon optimization for expression in mammalian cells, but this should not limit the use of other codon sequences encoding similar amino acids to those described. In some embodiments, the ICAM-1 targeting sequence may be repeated, and thus may appear in the fusion protein more than once. In embodiments, the enzyme segment comprises at least one of Acid sphingomyelinase (ASM), Alpha galactosidase (aGal), or Glucocerebrosidase (GCase), or a catalytically active fragment of any of said enzymes. The fusion protein may be delivered to an individual in need thereof using any of a variety of delivery forms and methods. The disclosure includes administration of the described fusion proteins, and polynucleotides encoding them, such as RNA or DNA or a suitable expression vector, or cells producing said proteins or nucleic acids or vectors. Thus, expression vectors, mRNA, and cDNAs encoding the fusion proteins are included. Also included are cells, including but not limited to mammalian cells, which further include but are not limited to human cells, that produce described fusion proteins or comprise the described vectors containing said sequences, as well as said cells to which a described fusion protein has bound, and/or which have internalized the fusion protein. The described proteins can be used as a protein therapy, a gene therapy, or by way of an implanted cell therapy, wherein the implanted cells express a described fusion protein. Organelles and cellular vesicles, such as lysosomes and exosomes, which comprise an intact or cleaved fusion protein, and organs, such as the lungs, liver or brain, to which these fusion proteins have been delivered are also included within the scope of the disclosure.

BRIEF DESCRIPTION OF THE FIGURES

The patent or application file contains at least one drawing executed in color. Copies of this patent or patent application publication with color drawing(s) will be provided by the Office upon request and payment of the necessary fee.

DETAILED DESCRIPTION

Figure 1:
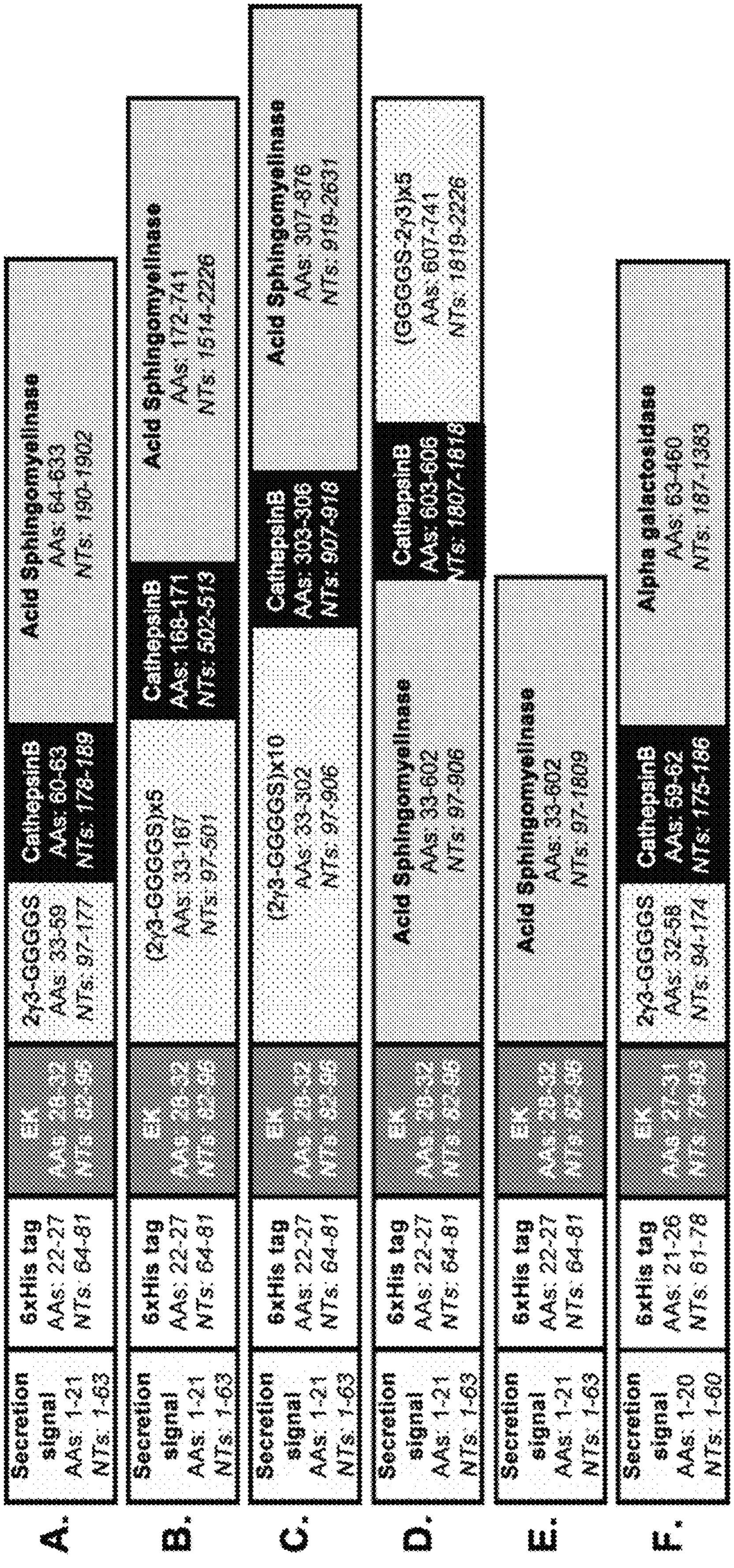
FIG. 1. Schematics of representative fusion proteins. (A.) Human acid sphingomyelinase (ASM) with one copy of the 2γ3 ICAM-1-targeting peptide at the amino terminus; (B.) human ASM with five tandem-repeats of the 2γ3 ICAM-1-targeting peptide at the amino terminus; (C.) human ASM with ten tandem-repeats of the 2γ3 ICAM-1-targeting peptide at the amino terminus; (D.) human ASM with five tandem-repeats of the 2γ3 ICAM-1-targeting peptide at the carboxyl terminus; (E.) human ASM control; (F.) human alpha galactosidase (αGal) with one copy of the 2γ3 ICAM-1-targeting peptide at the amino terminus; (G.) human αGal with five tandem-repeats of the 2γ3 ICAM-1-targeting peptide at the carboxyl terminus; (H.) human αGal control; (I.) human glucocerebrosidase (GCase) with one copy of the 2γ3 ICAM-1-targeting peptide at the amino terminus; (J.) human GCase with five tandem-repeats of the 2γ3 ICAM-1-targeting peptide at the amino terminus; and (K.) human GCase control.
Figure 1:
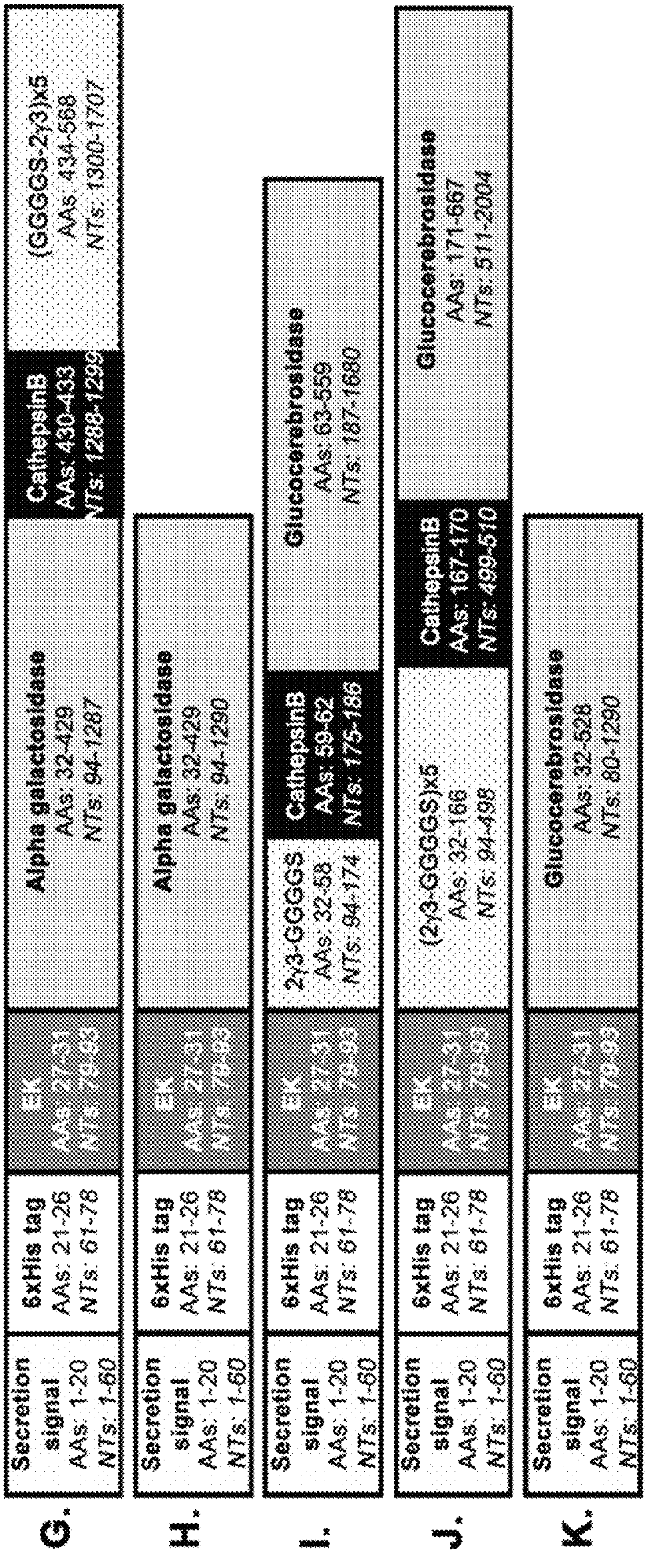

Unless defined otherwise herein, all technical and scientific terms used in this disclosure have the same meaning as commonly understood by one of ordinary skill in the art to which this disclosure pertains.

Every numerical range given throughout this specification includes its upper and lower values, as well as every narrower numerical range that falls within it, as if such narrower numerical ranges were all expressly written herein.

The disclosure includes all nucleotide and amino acid sequences described herein, and every nucleotide sequence referred to herein includes its complementary DNA sequence, and also includes the RNA equivalents thereof, and vice versa. All sequences described herein, whether nucleotide or amino acid, include sequences having 50.0-99.9% identity, inclusive, and including all numbers and ranges of numbers there between to the first decimal point. The identity may be determined across the entire sequence, or a segment thereof that retains its intended function. Homologous sequences from, for example, other enzymes, protease cleavage sites, secretion signals, and targeting moieties, are included within the scope of this disclosure, provided such homologous sequences also retain their intended function. Further, proteins of the present disclosure include functionally equivalent molecules in which amino acid residues are substituted for residues within the sequence resulting in a silent or conservative change. For example, one or more amino acid residues within the sequence can be substituted by another amino acid of a similar polarity that acts as a functional equivalent, resulting in a silent or conservative alteration. Substitutes for an amino acid within the sequence may be selected from other members of the class to which the amino acid belongs. For example, the nonpolar (hydrophobic) amino acids include, but are not limited to, alanine, leucine, isoleucine, valine, proline, phenylalanine, tryptophan, methionine, and combinations thereof. The polar neutral amino acids include, but are not limited to, glycine, serine, threonine, cysteine, tyrosine, asparagine and glutamine, and combinations thereof. The positively charged (basic) amino acids include, but are not limited to, arginine, lysine and histidine. The negatively charged (acidic) amino acids include aspartic acid, glutamic acid, and combinations thereof. Also included within the scope of the disclosure are proteins or fragments or derivatives thereof which exhibit the same or similar biological activity and derivatives which are differentially modified during or after translation, for example, by glycosylation, proteolytic cleavage, and the like.

Any result obtained using a method described herein can be compared to any suitable reference, such as a known value, or a control sample or control value, suitable examples of which will be apparent to those skilled in the art, given the benefit of this disclosure. In embodiments, any result obtained herein can be compared to a value obtained from analysis of components of the fusion proteins described herein, but wherein the components are configured differently, or are present in different copy numbers, or in a different stoichiometry, or are not present in the same, intact polypeptide. In embodiments, the disclosure provides for an improved result, relative to a result obtained using a targeting moiety and an enzyme that are present in the same composition, but are not present in the same polypeptide or were produced in the same polypeptide prior to enzyme release or liberation. In embodiments, the improved result comprises any one or combination of improved and/or increased enzymatic activity, such as enzyme activity measured at a pH below physiological pH, such as in a lysosome, an improved pharmacokinetic property, improved bioavailability property, improved stability, improved shelf life, improved production yield, improved safety, improved duration of activity, improved biodistribution, improved incorporation into a lysosome, and/or an improved effect on any sign or symptom of a lysosomal storage disease. In embodiments, a result obtained using a composition described herein is improved, relative to a result obtained using a composition that comprises a particulate carrier. In an embodiment, a fusion protein of this disclosure displays increased targeting and/or catalytic activity than a control enzyme that is not a component of a fusion protein. In embodiments, a fusion protein of this disclosure displays a measurable improvement relative to a control enzyme that is not a component of a fusion enzyme. In embodiments, a 1-10 fold improvement is achieved. In non-limiting embodiments, a fusion protein of this disclosure displays ≥700-1000% (7-10-fold) better targeting and/or ≥300% (3-fold) better catalytic activity than a control enzyme such as acid sphingomyelinase (ASM), with ≥50% enhancement after protease cleavage of the enzyme.

Figure 6:
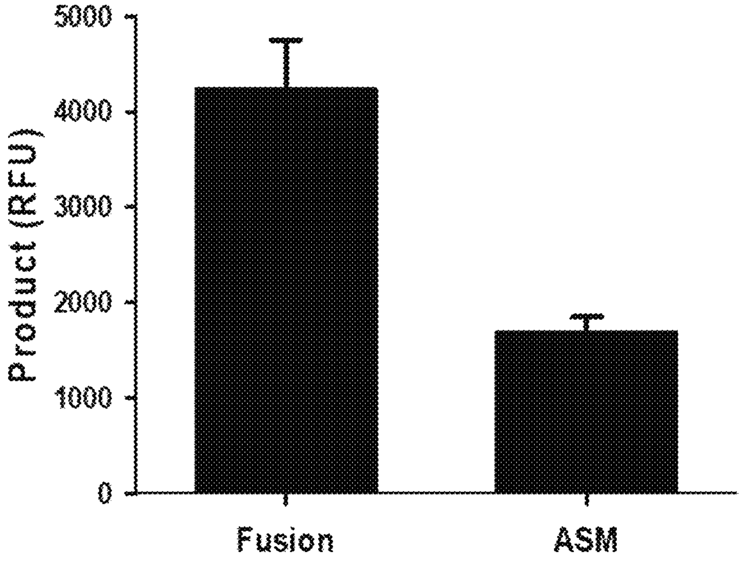
FIG. 6. Table (A.) showing comparative in vitro enzymatic activity of fusion proteins and respective non-fusion enzyme control and enterokinase (EK) cleaved fusion proteins, prior and after release with cathepsin B, at lysosomal versus neutral pH, and for fusions produced in different cell lines. (B., C., D.) Enzymatic activity, under lysosomal conditions of fusion proteins ((B.), fusion ASM; (C.) fusion GCase; (D.) fusion α-Gal) compared to respective control non-targeted enzymes.
Figure 6:
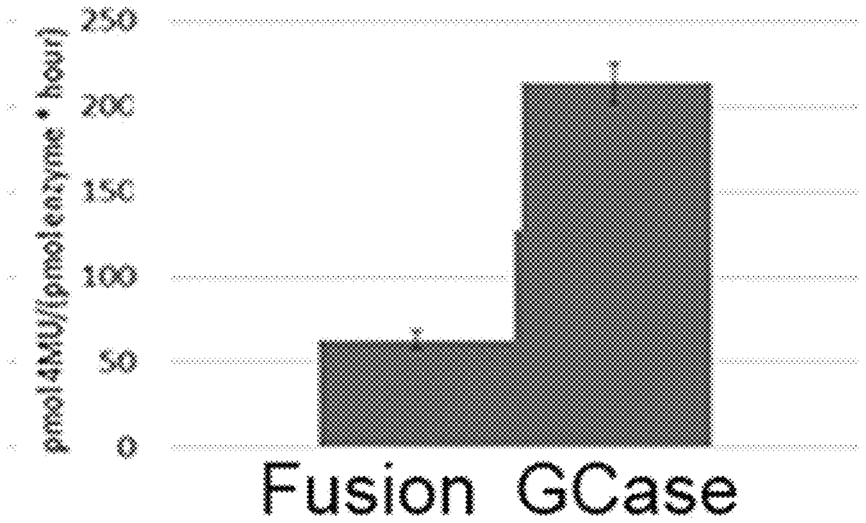
Figure 6:
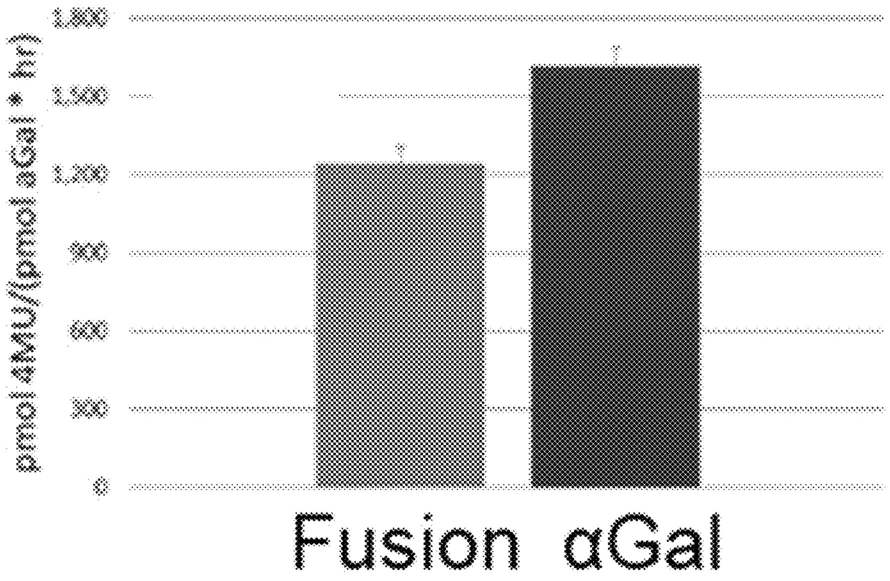

In connection with the foregoing, the present disclosure unexpectedly reveals, as in part demonstrated by Example 6 and FIG. 6 and the data in the Table referred to therein, that after cathepsin B cleavage of the fusion protein, the released enzyme, which no longer contains any other domains but the enzyme, exhibits more activity than an enzyme that was not previously part of a fusion protein. For example, both constructs sequence B and E (said constructs illustrated in FIG. 1) only differ in the targeting peptide and cathepsin B sequence. After cathepsin B cleavage, both products of sequences B and E are no different, yet after cathepsin B cleavage the product of B remains more active than the product of E. Without intending to be bound by any particular theory, it is considered that the fusion protein may have fold differently and, once liberated by protease activity, the enzyme part is more active. Hence, it is considered that the folding of the fusion protein is not the same than the non-fused enzyme. Thus, the disclosure provides for production of a fusion protein that contains a segment that is more active when freed from the fusion protein, relative to the same segment that is used in the absence of the fusion protein. In embodiments, a described fusion protein may therefore be considered to be a prodrug that is suitable for ERT, among other uses.

In one aspect, the disclosure comprises recombinant polypeptides, i.e., fusion proteins, for use in treating one or more LSDs, or additional diseases which may benefit from these enzyme activities, wherein the fusion proteins generally comprises:

i) one or more intercellular adhesion molecule-1 (ICAM-1) targeting segments;

ii) an enzyme segment that is catalytically active at the pH of a lysosome;

iii) optionally a first protease cleavage sequence segment between i) and ii), and optionally, one or more of:

iv) a secretion signal;

v) a protein purification tag; and vi) a second protease cleavage signal, such as for use in protein purification, for removal of iv) and v) from the final product.

In embodiments, a fusion protein of this disclosure comprises or consists of any combination of i)-vi), provided at least i) and ii), and preferably at least i), ii) and iii) are present.

Representative and non-limiting configurations of segments of fusion proteins that are included in this disclosure are provided in Example 1 and FIG. 1. Representative amino acid sequences of each of these segments, and DNA sequences encoding them, are also provided herein, but are not intended to be limiting. Representative amino acid sequences for constructs A-K in FIG. 1 are provided below as amino acid sequences 13-23, respectively. Numbering in FIG. 1 corresponds with amino acid numbers in the annotated segments of the construct maps.

Where polypeptides of this disclosure are described, expression vectors encoding the polypeptides are also included. The expression vectors can be used in production of the polypeptides, and/or as therapeutic agents, such as DNA vaccines. Representative and non-limiting DNA sequences encoding proteins are provided below.

In embodiments, the ICAM-1 targeting segment comprises or consists of the sequence NNQKIVNIKEKVAQIEA (SEQ ID NO: 1), referred to herein from time to time as 2γ3. In embodiments, the 2γ3 sequence is repeated in the fusion protein. In embodiments, the 2γ3 sequence is repeated 2 to 10 times in the fusion protein. In embodiments, one 2γ3 sequence is proximal to another sequence, such as a Gly and Ser containing sequence. e.g., a linker sequence. In embodiments, a suitable Gly Ser sequence contains GGGGS (SEQ ID NO:24). In embodiments, distinct 2γ3 segments are separated by a segment comprising the sequence GGGGSGGGGS (SEQ ID NO:25). A variety of other linkers are known in the art and can be used with embodiments of this disclosure.

As an alternative to 2γ3, other ICAM-1 targeting peptide sequences can be used. Some examples include but are not necessarily limited to:

(SEQ ID NO: 26)
NNQKIVNLKEKVAQLEA;

(SEQ ID NO: 27)
NNQKLVNIKEKVAQIEA;

(SEQ ID NO: 28)
YPASYQR;

(SEQ ID NO: 29)
YQATPLP;

(SEQ ID NO: 30)
GSLLSAA;

(SEQ ID NO: 31)
FSPHSRT;

(SEQ ID NO: 32)
YPFLPTA
and (SEQ ID NO: 33)
GCKLCAQ.

In embodiments, a fusion protein described herein comprises a targeting segment and/or a lysosomal enzyme segment described in U.S. Pat. No. 8,778,307, from which the description of targeting moieties and lysosomal enzymes are incorporated herein by reference.

The enzyme segment of the fusion proteins described herein can comprise any enzyme or catalytic fragment thereof that is also described herein. In non-limiting embodiments, the enzyme or catalytic fragment thereof can function in a lysosome. In one embodiment, the enzyme is Acid sphingomyelinase (ASM). In another embodiment, the enzyme is Alpha galactosidase. In another embodiment the enzyme is Glucocerebrosidase (GCase). The amino acid sequences of each of these enzymes are known in the art. As noted above, representative and non-limiting sequences are provided in the examples below, and representative configurations on the enzyme segment in relation to the other components of the fusion proteins are shown in Example 1 and FIG. 1. Any fusion protein of this disclosure may comprise or consist of the sequence of functional fusion proteins depicted in FIG. 1.

In embodiments, the fusion proteins provided by this disclosure comprise a first and second protease cleavage sequence. In general, the first and second protease cleavage sites are distinct from one another, and do not appear elsewhere in the fusion proteins.

In embodiments, the first cleavage sequence comprises a sequence that is cleaved by any protease originally located in a lysosome, which may be located within endosomes or lysosomes, or secreted extracellularly by cells. In embodiments, the protease cleavage signal is cleaved by any endosomal cysteine proteases, such cysteine proteases known in the art as Cathepsins. In embodiments, the protease recognition sequence is recognized by cathepsin L or cathepsin B. In an embodiment, a protease cleavage site used in fusion proteins of this disclosure comprises the sequence GFLG (SEQ ID NO:34). In this regard, representative and non-limiting examples of first protease cleavage site configurations in relation to fusion proteins of this disclosure are shown in Example 1 and FIG. 1, and by way of the sequences provided with this disclosure. In FIG. 1, the represented protease cleavage site is designated as Cathepsin B. The first protease recognition cleavage sequence is configured such that it can liberate the enzyme segment from the remainder of the fusion protein upon cleavage in a suitable physiological solution, such as within a lysosome. In embodiments the protease is thus sequestered to a lysosome, and therefore the enzyme is only liberated subsequent to being taken up by the lysosome. In embodiments, the disclosure thus provides a prodrug that is only activated in the lysosome, or another environment with a sufficiently low pH level such that the protease is active. In embodiments, the prodrug itself has enzymatic activity.

In embodiments, a fusion protein of this disclosure comprises a second protease cleavage signal which is intended to be used in protein isolation and/or purification. In embodiments, the second protease cleavage site is distinct from the first protease cleavage site. In specific but non-limiting embodiments, second protease cleavage sites that can be used in embodiments of this disclosure include the EK cleavage sequence DDDDK (SEQ ID NO:35), Tobacco etch virus (ENLYFQ (SEQ ID NO:36)), Factor Xa site IEGR (SEQ ID NO:37), matrix metalloproteinase 9 (MMP-9) PXXXX, where X in position 2 and 3 is any residue, position 3 is a hydrophobic residue, and the X in position 5 is S or T (SEQ ID NO:38), papain XXXXZRUXXX (SEQ ID NO:39) (where U is any residue but V), and Thrombin LVPRGS (SEQ ID NO:40).

In embodiments, a fusion protein of this disclosure comprises a secretion signal that is used for protein production and/or purification. Any suitable secretion signal can be used and many are known in the art. In one non-limiting embodiments, the secretion signal comprises (SEQ ID NO: 41)
METDTLLLWVLLLWVPGSTG
or (SEQ ID NO: 42)
MGWSCIILFLVATATGVHSD.

In embodiments, fusion proteins provided in this disclosure may include protein purification tags. Any suitable protein purification tag can be used. In a non-limiting embodiment, a poly-histidine tag is used. A His-tag as used herein is a linear sequence of n histidine residues where n is typically 6-8.

In embodiments, the disclosure comprises administering therapeutically effective amounts of a described fusion protein to an individual in need thereof. In embodiments, the fusion protein to be used in a therapeutic method will have been produced and processed such that the secretion signal and the protein purification tag are removed from a portion of the fusion protein comprising the ICAM-1 targeting and enzyme segments by cleavage at the second protease cleavage sequence. In other embodiments, the purification tag is not removed.

Therapeutically effective amount means that amount of a recombinant polypeptide of this disclosure that will elicit the biological or medical response of a subject that is being sought. A "therapeutically effective amount" in certain implementations means an amount sufficient to prevent or reduce signs and/or symptoms of any disorder wherein an enzyme described herein could have a prophylactic and/or therapeutic benefit.

In embodiments, a therapeutically effective amount rescues an LSD disorder caused by a deficiency of one or more lysosomal enzymes. Effective amounts of polypeptides of this disclosure will depend in part on the particular LSD, the size and weight of the individual, etc. For any recombinant polypeptide disclosed herein, an effective dose can be estimated initially either in cell culture assays or in animal models, usually mice, rabbits, dogs, pigs, or non-human primates. The animal model is also used to achieve a desirable concentration range and route of administration. Such information can then be used to determine useful doses and routes for administration in humans. In embodiments, a fusion protein of this disclosure is administered such that it reaches the lungs and/or brain of an individual. Prophylactic dosing and uses are also included in this disclosure. Prophylactic or therapeutic doses can encompass a broad range of concentration including, but limited to, 0.01 mg/Kg to 20 mg/Kg.

In embodiments, the disclosure provides compositions comprising the described polypeptides, such as pharmaceutical formulations. In embodiments, the non-limiting compositions are free of particulate carriers. In embodiments, compositions are free of any one or combination of polystyrene nanocarriers, poly-lactic co-glycolic acid (PLGA) nanocarriers, polyethylene glycol (PEG), poly-lactic acid (PLA) nanocarriers, and biopolymeric dendrimers. In embodiments, a protein or polynucleotide encoding the protein as provided herein is not covalently or ionically coupled to a particle.

In embodiments, a pharmaceutical composition comprises a pharmaceutically acceptable carrier. Suitable carriers include, for example, diluents, adjuvants, excipients, or other vehicles with which the present complexes may be administered to an individual. Non-limiting examples of materials which can serve as pharmaceutical carriers include: sugars, such as lactose, glucose and sucrose; starches, such as corn starch and potato starch; cellulose, including sodium carboxymethyl cellulose, ethyl cellulose and cellulose acetate; powdered tragacanth; malt; gelatin; talc; excipients, such as cocoa butter; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; phosphate buffer solutions; and other non-toxic compatible substances employed in pharmaceutical formulations. The composition, if desired, can also contain minor amounts of wetting or emulsifying agents, or pH buffering agents. Some examples of compositions suitable for mixing a composition of this disclosure can be found in: Remington: The Science and Practice of Pharmacy (2005) 21st Edition, Philadelphia, Pa. Lippincott Williams & Wilkins.

Methods of using the therapeutic compositions include administration by any acceptable approaches including but not limited orally and parenterally. For example, the recombinant polypeptides can be administered intramuscularly, subdermally, subcutaneously, topically, intracranially, intratracheally, by instillation, intravenously, and intra-arterial. In embodiments, the fusion protein is loaded on or in cells for release in the body, e.g., cells such as erythrocytes can be loaded with proteins, injected in circulation, and release the protein over time which then target the intended organs. In embodiments, a fusion protein of the disclosure is administered in combination with any suitable nanoparticles. In embodiments, a composition comprising a fusion protein may be administered by a device, such as a medical pump, implant, patch, or chip.

In embodiments, a polypeptide or polynucleotide encoding such polypeptide is administered to an individual in need thereof. In embodiments, the individual in need thereof has been diagnosed with or is suspected of having any disorder that is correlated with a lysosomal storage disease, non-limiting examples of which include Pompe Disease, GM1 gangliosidosis, Tay-Sachs disease, GM2 gangliosidosis, Sandhoff disease, Fabry disease, Gaucher disease, metachromatic leukodystrophy, Krabbe disease, Niemann-Pick disease type A, Niemann-Pick disease type B, Niemann-Pick disease type C, Niemann-Pick disease type D, Farber disease, Wolman disease, Hurler Syndrome, Scheie Syndrome, Hurler-Scheie Syndrome, Hunter Syndrome, Sanfilippo A Syndrome, Sanfilippo B Syndrome, Sanfilippo C Syndrome, Sanfilippo D Syndrome, Morquio A disease, Morquio B disease, Maroteaux-Lamy disease, Sly Syndrome, α-mannosidosis, β-mannosidosis, fucosidosis, aspartylglucosaminuria, sialidosis, mucolipidosis II, mucolipidosis III, mucolipidosis IV, Goldberg Syndrome, Schindler disease, cystinosis, Salla disease, infantile sialic acid storage disease, Batten disease, infantile neuronal ceroid lipofuscinosis, or prosaposin.

In alternative embodiments, the individual has any type of cancer, or Parkinson's disease. In embodiments, the cancer is a blood cancer or a solid tumor, either primary or metastatic, that affects any part of the body.

The disclosure includes expression vectors encoding the fusion proteins, and methods of making the fusion protein using the expression vectors. In general, a method of making the fusion proteins comprises allowing expression of an expression vector encoding the fusion proteins in a cell culture, and separating the protein from the cell culture using any suitable approach. The proteins can be separated and purified to any desired degree of purity. In certain embodiments, the disclosure includes cell cultures that contain the expression vectors. In certain embodiments, the cell cultures are eukaryotic cell cultures.

In embodiments, the disclosure includes administering to an individual an expression vector encoding a fusion protein described herein, or otherwise configured to result in expression of the fusion protein once the expression vector is introduced into a cell. In embodiments, any of a variety of retroviral vectors, such as lentiviral vectors, or adenoviruses, adeno-associated viruses, herpes, and vaccinia viruses can be used. In embodiments, RNA encoding the fusion protein can be directly injected into the cells or otherwise introduced to the individual. Polynucleotide vectors can include modified nucleotides or phosphate backbone moieties, many suitable examples of which are known in the art. CRISPR/Cas technology can also be used to introduce in the genome the coding sequence of the described fusion proteins.

In one representative approach, which is further illustrated by the Examples presented below, 5 tandem repeats of 2γ3 were cloned for enhanced ICAM-1 affinity, each repeat separated from the next by a short peptide linker to enable their independent folding (targeting domain=135 amino acids). At the carboxyl-terminus of the targeting domain, a 4 amino acid cathepsin B sequence was placed to enable lysosomal cleavage and release of human ASM, which was cloned at the carboxyl-terminus of the release domain. This catalytic domain is 570 amino acids-long and encompasses human ASM mRNA sequence starting at His62, which lacks the enzyme's natural secretion sequence. The targeting+cleavage+catalytic cassette ("functional domains") was preceded at the amino-terminus by "production domains", consisting of a 21 amino acid signal peptide for secretion of the fusion protein from transfected cells into the culture medium, a 6 amino acid His-tag for affinity purification, and a 5 amino acid enterokinase cleavage site to separate the production domains from the functional domains which constitute the intended fusion protein. The full sequence was cloned into a plasmid vector to enable transient and stable expression in mammalian cells. In addition, computer predictions were pursued to examine the resulting conformation of the targeted fusion proteins. Results suggested that the designed fusion protein would match the folding of respective human wild-type enzymes which endogenously reside in lysosomes of our bodies.

To produce data described in the Examples below, a plasmid vector containing the expression cassette for an ASM fusion protein was transfected in CHO-3E7, Expi-CHO-S and 293-6E cells. In all cases, collection of the cell medium 5-7 days post-transfection, followed by affinity purification using the His-tag domain and electrophoresis under reducing conditions, showed a protein band of ≈80 KDa (expected size), quantified as ≈90% purity. Similar cells were transfected with plasmids containing the expression cassettes for GCase and αGal fusion proteins, respectively, which also resulted in the production of proteins of expected size and purity ranging from 39 to 90%. Subsequent optimization of the purification protocol raised purity to ≥90% in all cases. Electrophoresis under non-reducing conditions revealed monomeric, dimeric, and tetrameric protein at ≈25%, 25%, 50% for 293 cells and 30%, 15%, 55% for CHO cells in the case of ASM fusion protein. This was because natural ASM assembles into monomeric and oligomeric forms in the body, all of which are functional. Three independent production rounds in CHO cells showed high reproducibility. The production yield was high, e.g. ≈5-8 mg/L of culture for CHO-3E7 and ≈35-40 mg/mL for Expi-CHO-S. Western blot (WB) validated that the fusion protein contained His-tag and enzyme modules, for which antibodies are available. It also validated that the His-tag was cleaved off the fusion protein by enterokinase, which was then removed by size exclusion chromatography for a final purity of ≈85%. In the case of an ASM fusion protein, WB also showed that cathepsin B cleavage released a protein band of ≈70 KDa recognized by anti-ASM, as expected. Similar results were obtained for GCase fusion protein and αGal fusion protein.

When hundreds of copies of 73 peptides are coupled on the surface of polymer nanoparticles, particles target human and mouse ICAM-1 (Garnacho et al., J Pharm Exp Ther, 340:638 & Garnacho et al., J Drug Targeting. 25:786). However, these peptides were never tested outside the context of these high affinity nanoparticles. We observed that, in CHO cells that expressed 2γ3-ASM fusion protein, ASM was stained using anti-ASM+FITC-secondary antibody, abundant label associated with the cells. This was in contrast to non-transfected CHO cells, despite the fact that CHO cells express natural ASM, which we verified by Western blotting (WB). Fluorescence detection could have been enabled by enhanced expression of fusion protein over natural ASM, yet we had demonstrated that fusion protein is secreted to the cell medium. In fact, WB validated the almost absence of fusion protein in cell lysates vs. the cell medium. Therefore, the fluorescence signal may be due to binding of secreted fusion protein on cells, indicating ICAM-1 binding, as WB verified the presence of ICAM-1 expression in these CHO cells. In addition, incubation of purified fusion protein with HUVEC cells (known to express ICAM-1) for 3 h at 37-C, followed by cell fixation, permeabilization and staining using anti-ASM+FITC-secondary antibody, showed bright green-FITC dots indicative of endo-lysosomal uptake of the fusion protein by cells. This was not observed when HUVECs were incubated with control non-targeted ASM (Olipudase), demonstrating the targeting ability of the fusion protein.

After demonstrating the presence of an ASM enzyme sequence in the fusion protein, its catalytic function was assessed. For this purpose, a commercial kit was used, which is based on catalytic hydrolysis of sphingomyelin and final production of fluorescent Resorufin, which can be quantified by spectrofluorometry. As further demonstrated in the Examples below, in the absence of cathepsin B or low cathepsin B concentration, some ASM activity was found over negative control levels, indicating that the fusion protein is active. More importantly, ASM activity doubled upon raising cathepsin B concentration, indicating that a fully active enzyme results upon release by cathepsin B. Furthermore, ASM activity increased by several fold at pH 4.5, which is reflective of lysosomal conditions, vs. neutral pH 7.4. These results suggest that maximal ASM activity will be obtained upon lysosomal delivery of the fusion protein, which would prevent any undesirable ASM activity in circulation, observed for Olipudase. Similar results were found for GCase and αGal fusion proteins, indicating that all fusion proteins have prevalent activity under lysosomal conditions. In addition, the catalytic activity of the fusion protein under lysosomal conditions was 2-3-fold enhanced compared to the control ASM. The activity of GCase and αGal fusion proteins was also enhanced compared to their respective controls.

Next, both the targeting and trafficking of fusion proteins were compared against similar control non-targeted enzymes. For example, in a pharmacological model of ASM deficiency, cell association of control ASM was much lower (7-10 fold by immunofluorescence detection and 3-4 fold by radioisotopic tracing) compared to ASM fusion protein. Similarly, association of GCase fusion protein to induced pluripotent stem cell (iPS)-derived neurons from a Gaucher patient was about 3 fold enhanced compared to respective control non-targeted enzyme. In the latter case, GCase fusion was visualized to traffic to lysosomes in neurons, while control Cerezyme® used at similar activity units was not visible.

Skin fibroblasts from patients diagnosed for ASM deficiency (NPD) and skin fibroblasts from healthy individuals were tested as a part of this disclosure. No personal data was associated with them. First, both healthy and diseased cells were incubated overnight with a commercial fluorescent sphingomyelin (BODIPY-FL-C12-sphingomyelin), a substrate analogue for ASM, which fluoresces green. Microscopy examination of said cells showed that diseased cells accumulated increased levels of sphingomyelin compared to healthy cells. Incubation of diseased cells for 5 h with control, non-targeted ASM (from which Olipudase was derived) vs. similar concentration of fusion protein resulted in differential degradation of the stored sphingomyelin. Control ASM only degraded 4% of the sphingomyelin stored in diseased cell vs. 27% degradation for the fusion protein, which represents a 6-7-fold improvement in the intracellular activity after only 5 h incubation. Similar results were found for GCase fusion protein and αGal fusion proteins when compared to respective control enzymes in skin fibroblasts from patient with Gaucher disease and Fabry disease, respectively.

Apart from enhanced enzymatic activity and substrate reduction observed by fusion proteins, additional effects were studied. For instance, fluorescence microscopy showed that acidic compartments such as lysosomes were aberrantly engorged in iPS-derived neurons from Gaucher patients compared to healthy wildtype counterparts. Incubation with GCase fusion protein normalized the size of said compartments while control Cerezyme exerted only a partial reduction. In addition, GCase fusion protein did not cause cytotoxicity after 48 incubation with iPS-derived neurons compared to a positive control, $H_2O_2$, which is known to cause cell death.

Next, the capacity of fusion proteins to be transported across the BBB was tested in a multicellular model consisting of human brain endothelial cells, human astrocytes and iPS-derived neurons from a Gaucher patient. After validating the barrier function of this model, GCase fusion protein was demonstrated to cross this BBB model and accumulate in the subjacent neurons, while control non-targeted enzyme was trapped in the BBB and did not significantly accumulate in neurons after 24 h incubation. Additionally, pre-incubation of this model with anti-ICAM antibody blocked the interaction of GCase fusion with cells, while pre-incubation with anti-mannose-6-phosphate receptor antibody did not. This demonstrated an ICAM-1, not mannose-6-phosphate receptor, mediated process.

The ASM knock-out mouse mimics both type A (neurological) and type B (peripheral) NPD. We radiolabeled samples and injected i.v. 0.13 mg/Kg of $^{125}$I-ASM-fusion protein or $^{125}$I-ASM in mice. Measurement of the radiotracer in blood and tissues showed that both proteins disappeared fast from the circulation: by 1 h, 20% of the injected dose (% ID) was in blood for ASM and only 8.5% ID for the ASM-fusion protein. Since Olipudase has shown systemic toxicity, a reduction in circulation time for ASM-fusion protein may improve this. ASM-fusion protein was detected in the brain, lung, liver, spleen, heart, and kidneys, all of which need treatment. The localization ratio, which is the tissue-to-blood accumulation (% ID per gram in an organ over % ID per gram in the blood), was increased for the ASM-fusion protein over control ASM even after only 1 h after one single dose: e.g., 35% increase in the brain (main target in type A NPD) and 80% increase in the lung, 3.3-fold in the liver, and 3-fold in the spleen (main targets in type B NPD). Hence, the fusion protein had enhanced in vivo delivery. In addition, this fusion protein was loaded on nanoparticles, which showed enhanced removal from the circulation and enhanced targeting to peripheral organs (e.g. the lungs) and the central nervous system (e.g. the brain) compared to fusion protein not loaded in nanoparticles. Next, mice were injected i.v. with 0.6 mg/kg of ASM-fusion protein without nanoparticles, every two days for a total of 6 injections, vs. mice injected with control buffer. At the end of the experiment, blood and organs were measured for sphingomyelin and cholesterol, disease hallmarks. Multiple sphingomyelin and cholesterol species were reduced, which is needed for therapy. Ceramide product (associated to Olipudase side effects) was not significantly increased. An example is shown below for the brain, the organ where Olipudase has no effect. As seen, in the Examples below, 10 sphingomyelin species and 16 cholesterol species were lowered upon treatment with ASM-fusion protein. Instead, only a ceramide species was slightly increased upon treatment which suggest lack of any major ceramide burst which may lead to relevant side effects.

Mice were monitored each day during the study. The mice showed no statistical changes in the body weight for ASM-fusion protein vs. control buffer, or for parameters such as grooming and general activity. Hematological (RBCs, all types of leukocytes, platelets) and biochemical (glucose) tests showed no statistically significant changes between mice injected with fusion protein vs. control buffer, and this was also true for renal toxicity markers (BUN, creatinine) and hepatic toxicity markers (alkaline phosphatase). This, together with no overt increase in ceramide, the ASM product which is burst-produced and leads to toxicity of current ASM-Olipudase ERT, shows relative safety of the presently provided fusion strategy.

It will be apparent to those skilled in the art that the foregoing description illustrates: 1) fusion proteins of this disclosure have been generated and encompass various configurations of a 2γ3 ICAM-1 targeting module and ASM, GCase, or αGal catalytic modules, separated by a cathepsin B cleavable peptide which leads to the release of functional enzyme within the lysosomes; (2) these fusion protein possess enhanced targeting, trans-BBB transport, cellular uptake, and lysosomal trafficking in pharmacological cell models and patient cells; and (3) fusion proteins provide enhanced catalytic activity under lysosomal conditions in vitro and in cell cultures, in comparison to control non-targeted enzymes and commercial enzymes; (4) they provide enhanced substrate reduction and lysosomal size reduction; and (5) these fusion proteins surpassed both the targeting and functional performance, with respect to control enzyme, in mouse models (particularly the brain), with no appreciable side effects.

The foregoing results are reiterated and expanded upon by the following Examples, which are presented in order to more fully illustrate the preferred embodiments of the invention and should in no way be construed as limiting the scope of the invention.

Unless indicated otherwise, for representative demonstrations described in these Examples, controls correspond to the cDNA or amino acid sequence of non-targeted enzymes, while all other cases represent the cDNA or amino acid sequence of fusion proteins consisting of an ICAM-1 targeting domain and an enzyme domain, separated by a cleavage domain to release the enzyme domain from the targeting domain in the lysosome. In all cases, control and others, the cDNA or amino acid sequences may contain at the amino terminus of the proteins a signal peptide domain for secretion, followed by a tag domain for purification, followed by a domain for cleavage of said signal and tag domains.

EXAMPLES

Example 1, illustrated by FIG. 1, Expression cassette of ICAM-1-targeted fusion enzymes. Schematics of the domain design for: (A) Human acid sphingomyelinase (ASM) with one copy of the 2γ3 ICAM-1-targeting peptide at the amino terminus; (B) human ASM with five tandem-repeats of the 2γ3 ICAM-1-targeting peptide at the amino terminus; (C) human ASM with ten tandem-repeats of the 2γ3 ICAM-1-targeting peptide at the amino terminus; (D) human ASM with five tandem-repeats of the 2γ3 ICAM-1-targeting peptide at the carboxyl terminus; (E) human ASM control; (F) human alpha galactosidase (αGal) with one copy of the 2γ3 ICAM-1-targeting peptide at the amino terminus; (G) human αGal with five tandem-repeats of the 2γ3 ICAM-1-targeting peptide at the carboxyl terminus; (H) human αGal control; (I) human glucocerebrosidase (GCase) with one copy of the 2γ3 ICAM-1-targeting peptide at the amino terminus; (J) human GCase with five tandem-repeats of the 2γ3 ICAM-1-targeting peptide at the amino terminus; and (K) human GCase control. Controls correspond to the non-targeted enzymes, while all other cases represent fusion proteins consisting of a targeting domain and an enzyme domain, separated by a cathepsin B cleavage domain to release enzyme domain from the targeting domain in the lysosome. In all cases, control and others, the expression cassettes contain at the amino terminus of the fusion proteins a signal peptide domain for secretion, followed by a His-tag domain for purification, followed by an enterokinase domain (EK) for cleavage of said signal and tag domains. Also, in all cases, human enzymes are truncated at their amino termini to eliminate endogenous signal peptides. From these amino acid (AAs) designs, the corresponding nucleotide (NTs) designs were made using codon optimization for the intended expression in mammalian cells.

Figure 2:
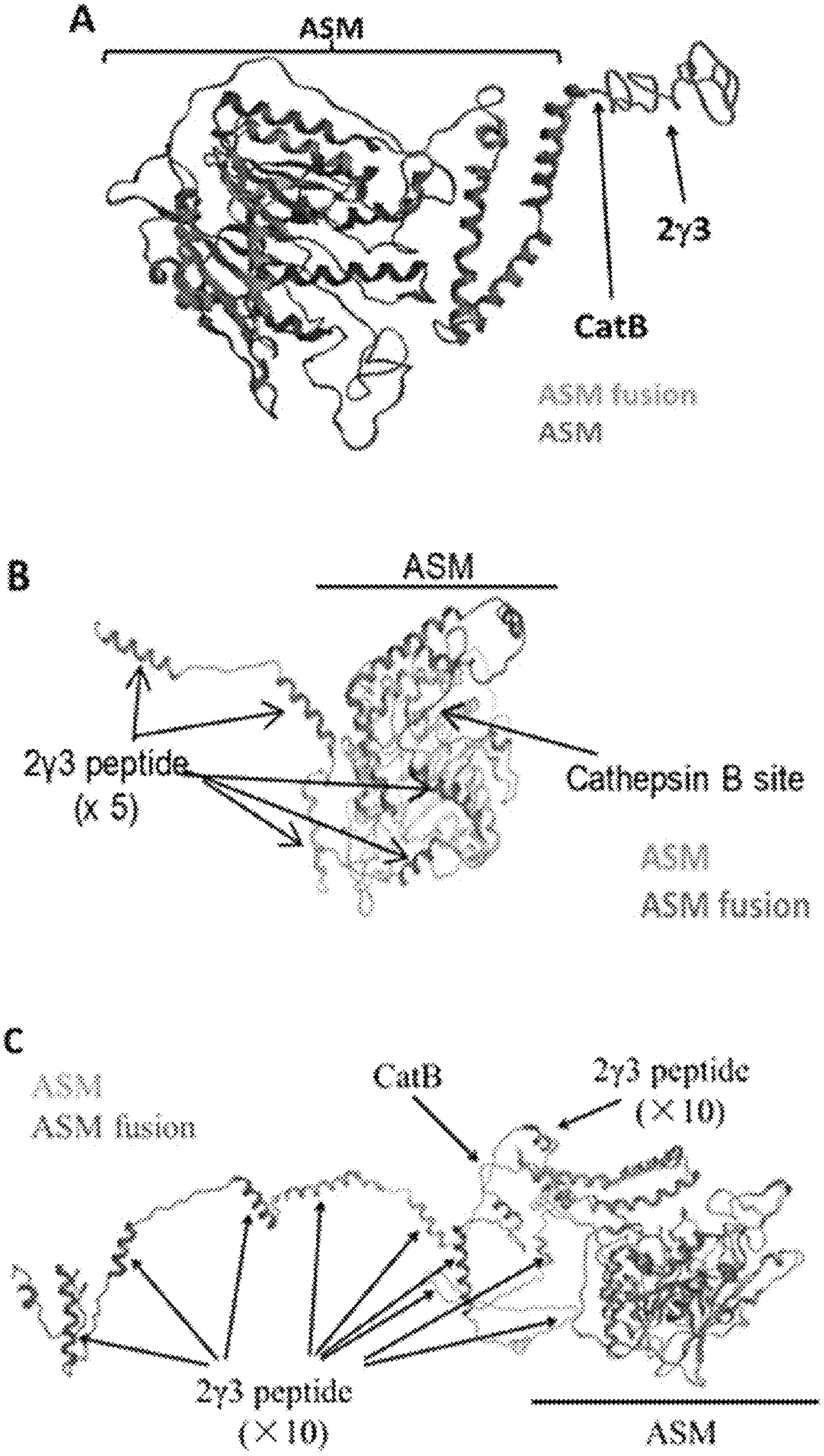
FIG. 2. Cartoon depictions of in silico simulations of the structure of fusion protein from FIG. 1: (A) ASM fusion A in FIG. 1, (B) ASM fusion B in FIG. 1, (C) ASM fusion C in FIG. 1, (D) ASM fusion D in FIG. 1, (E) αGal fusion G in FIG. 1, and (F) GCase fusion J in FIG. 1.
Figure 2:
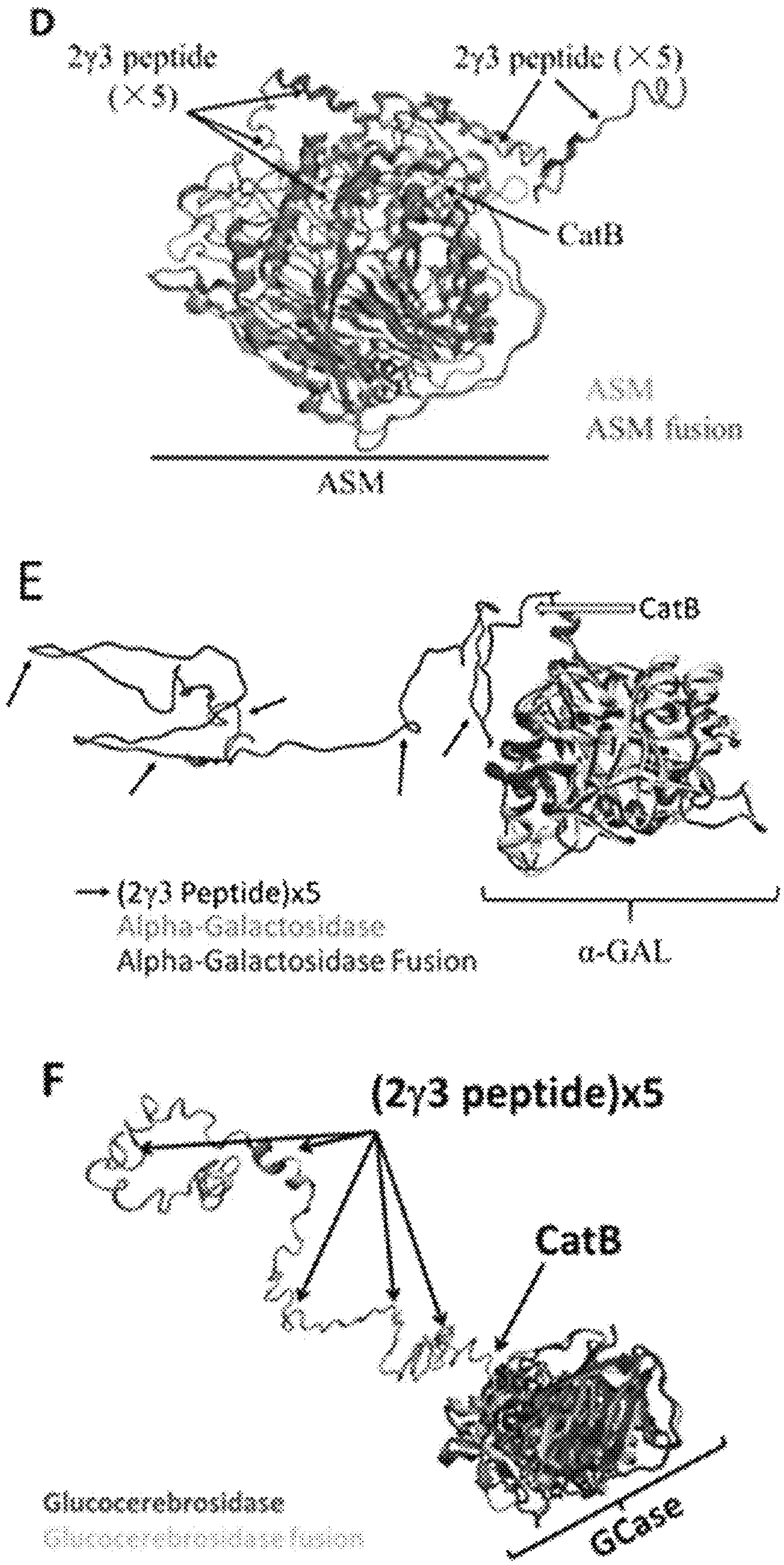

Example 2, illustrated by FIG. 2. Predicted structure of ICAM-1-targeted fusion enzymes. A) Fusion protein containing one copy of the 2γ3 ICAM-1-targeting peptide at the amino terminus, followed by a cathepsin B (CatB) cleavage site for lysosomal release of truncated human acid sphingomyelinase (ASM). (B) Fusion protein containing five tandem-repeats of the 2γ3 ICAM-1-targeting peptide at the amino terminus, followed by CatB cleavage site for lysosomal release of truncated human ASM. (C) Fusion protein containing ten tandem-repeats of the 2γ3 ICAM-1-targeting peptide at the amino terminus, followed by CatB cleavage site for lysosomal release of truncated human ASM. (D) Fusion protein containing truncated human ASM at the amino terminus, followed by CatB cleavage site for lysosomal release, followed by five tandem-repeats of the 2γ3 ICAM-1-targeting peptide at the carboxy terminus. (E) Fusion protein containing truncated human alpha galactosidase (αGal) at the amino terminus, followed by CatB cleavage site for lysosomal release, followed by five tandem-repeats of the 2γ3 ICAM-1-targeting peptide at the carboxy terminus. (F) Fusion protein containing five tandem-repeats of the 2γ3 ICAM-1-targeting peptide at the amino terminus, followed by CatB cleavage site for lysosomal release of truncated human glucocerebrosidase (GCase).

Figure 3:
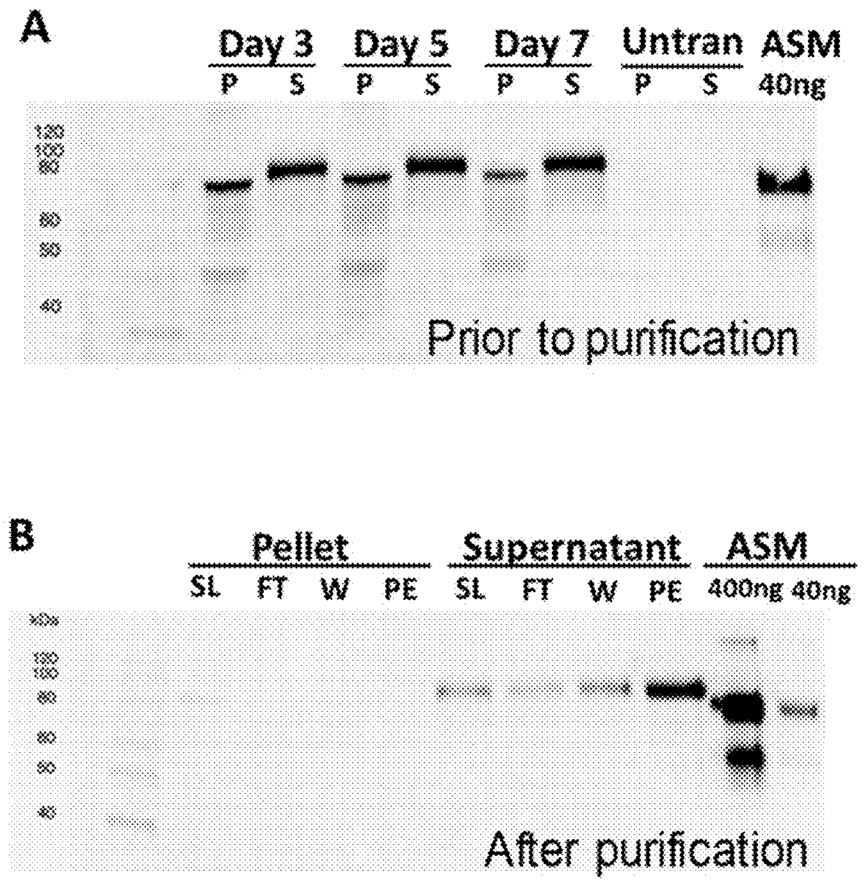
FIG. 3. Photographs of gels after protein electrophoresis followed by western blotting of fusion proteins secreted by CHO cells. (A) prior to and (B) after fusion protein affinity purification via His-tag domain.

Example 3, illustrated by FIG. 3. Production and purification of ICAM-1-targeted fusion enzymes. Protein electrophoresis followed by western blotting of fusion proteins secreted by CHO cells, shown (A) prior and (B) after fusion protein affinity purification via His-tag domain. Fusion protein is that shown in panel (B) in Example 2 above. (A) Higher molecular weight band in the cell medium supernatant (S) corresponds to the fusion protein, versus the low molecular weight band in the cell pellet (P), which corresponds to the cell endogenous enzyme. ASM=control purified recombinant enzyme has lower molecular weight than fusion protein and similar to endogenous ASM in cells. Different production days are shown. (B) No fusion protein is purified from the cell pellet fractions (Sample (SL), Flow-through after passing through an anti-his tag affinity column (FT), wash fraction (W), and pooled elution from the affinity column (PE)), since endogenous ASM does not have a His-tag. Fusion protein is present in the corresponding fractions from the cell medium supernatant, verifying its secretion. The pooled eluted fraction of the cell medium supernatant is enriched for the fusion protein. Untran=untransfected control cells.

Figure 4:
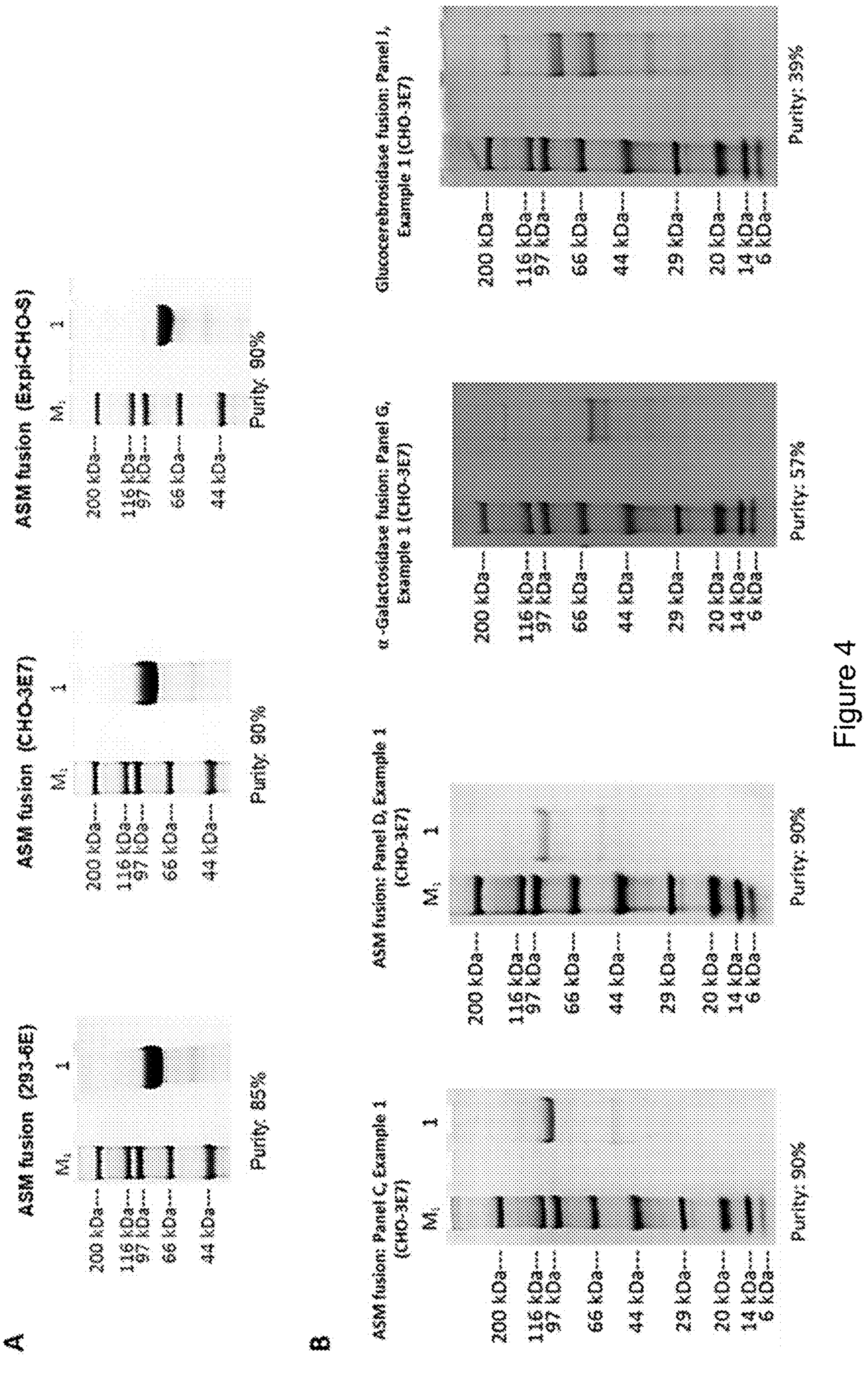
FIG. 4. Photographs of gels after protein electrophoresis followed by Coomassie blue after purification of (A) the same fusion enzyme from different cell sources or (B) different fusion enzymes in the same cell source. The data show reproducibility and purity of ICAM-1-targeted fusion enzymes.

Example 4, illustrated by FIG. 4. Reproducibility and purity of ICAM-1-targeted fusion enzymes. (A) Electrophoresis followed by Coomassie blue staining demonstrate that the fusion protein in panel (B) in Example 2 above was independently produced in and purified from three mammalian cell lines (293-6E, CHO-3E7, and Expi-CHO-S), showing great reproducibility and purity. (B) Other fusion proteins are shown, including fusion proteins in panels C, D, G and J (Example 1 above) all produced in the CHO-3E7 cell line.

Figure 5:
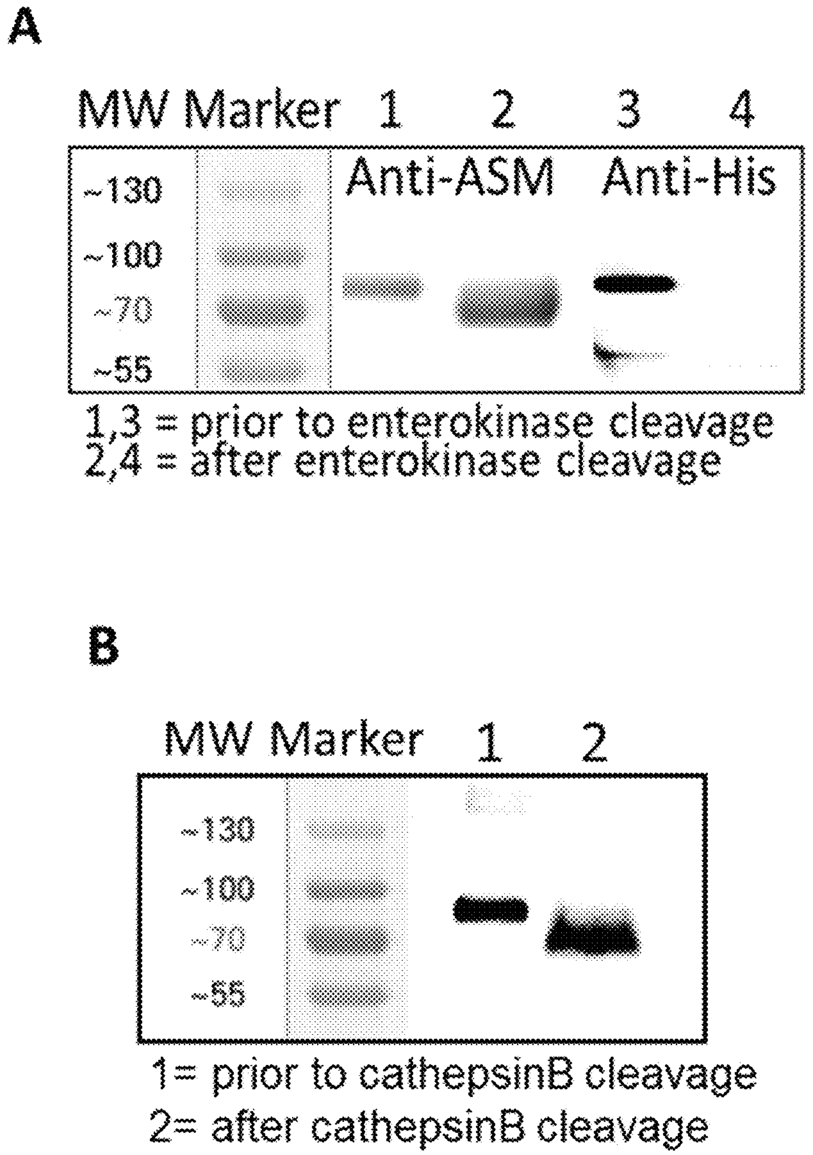
FIG. 5. Photographs of gels after protein electrophoresis followed by Western blotting of ICAM-1-targeted fusion enzymes. (A) Prior to and after cleavage with enterokinase. (B) Prior to and after cleavage with cathepsin.

Example 5, illustrated by FIG. 5. Western blotting of ICAM-1-targeted fusion enzymes. (A) After purification of the fusion protein shown in panel (B) in Example 2 above, Western blotting was conducted using antibody to detect the enzyme domain (ASM) and the His-tag domain used for purification, both prior and after enterokinase cleavage to remove the His-tag from the fusion protein. (B) Similarly, the purified fusion protein shown in panel (B) in Example 2 above was cleaved with cathepsin B to remove the targeting group from the enzyme and western blotting was conducted to determine the enzyme domain (ASM). The lower molecular weight band corresponds to that of the ASM portion of the fusion protein.

Example 6, illustrated by FIG. 6. Enzymatic activity of ICAM-1-targeted fusion enzymes. (A) The table shows the comparative in vitro enzymatic activity of fusion proteins and respective non-fusion enzyme control as well as some enterokinase (EK) cleaved fusion proteins, prior and after release with cathepsin B, at lysosomal versus neutral pH, and for fusions produced in different cell lines where B, C, D and E are as in Example 1. (B) Enzymatic activity, under lysosomal conditions, of fusion protein B in Example 1 was additionally compared to full recombinant ASM produced by He et. al. (He, Miranda et al. 1999), which served as basis for Genzyme Olipudase®. The fusion enzymes are more active in lysosomal conditions (acidic) compared to circulation conditions (neutral) and are even more active after removal of the His tag, as expected. (C) Enzymatic activity, under lysosomal conditions, of GCase fusion protein J in Example 1 compared to control non-targeted GCase protein K in Example 1. (D) Enzymatic activity, under lysosomal conditions, of α-Gal fusion protein G in Example 1 compared to control non-targeted α-Gal protein H in Example 1.

Figure 7:
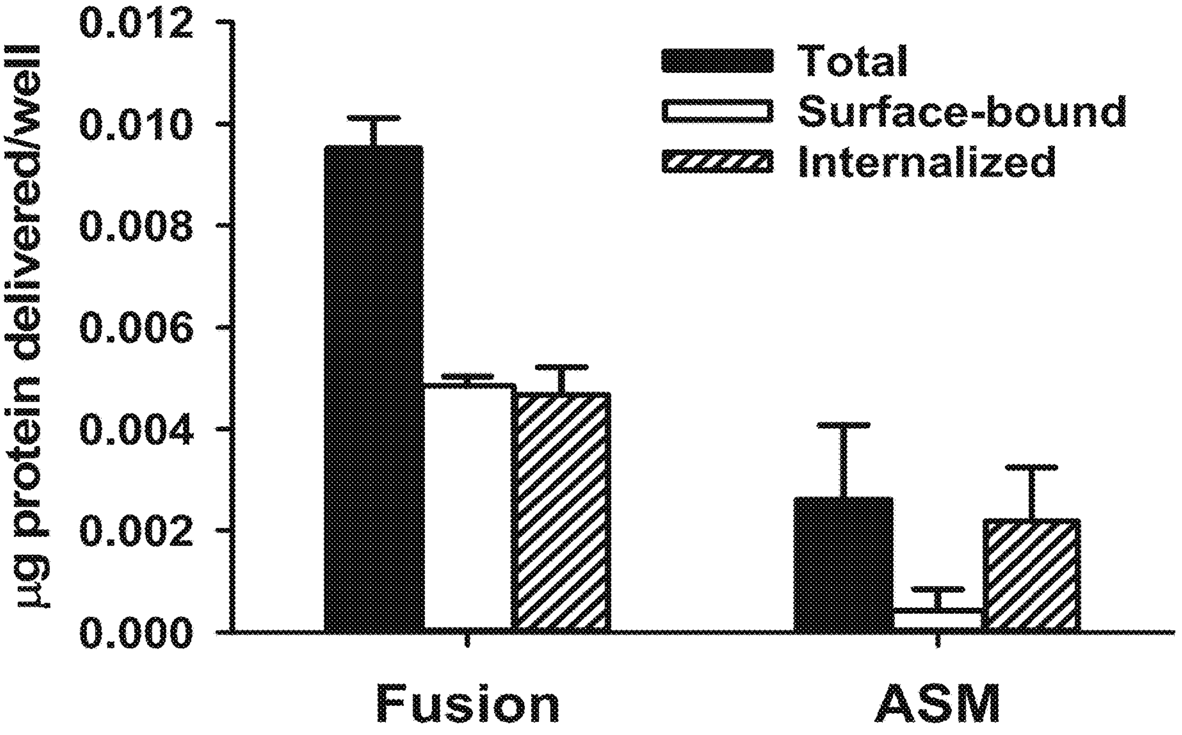
FIG. 7. Graph showing cell binding and internalization of an ICAM-1-targeted fusion enzyme compared to respective control non-targeted enzyme.

Example 7, illustrated by FIG. 7. Cell binding and internalization of ICAM-1-targeted fusion enzymes. A pharmacological model of Niemann-Pick disease types A and B was used, which consists of treating cells with imipramine, a small molecule known to degrade endogenous ASM. Cells were additionally treated with TNFα to mimic an inflammatory status, as it pertains to Niemann-Pick disease. Cells were then incubated for 3 hours at 37-C with either fusion protein B in Example 1 (after enterokinase cleavage), or full recombinant ASM produced by He et. al. (He, Miranda et al. 1999), which served as basis for Genzyme Olipudase®. In both cases, proteins were labeled with $^{125}$Iodine to allow tracing of their association with cells. Surface-bound fraction was eluted with a glycine solution and the remaining, non-eluted fraction corresponds to internalized protein. The sum of both fractions represents the total cell association.

Figure 8:
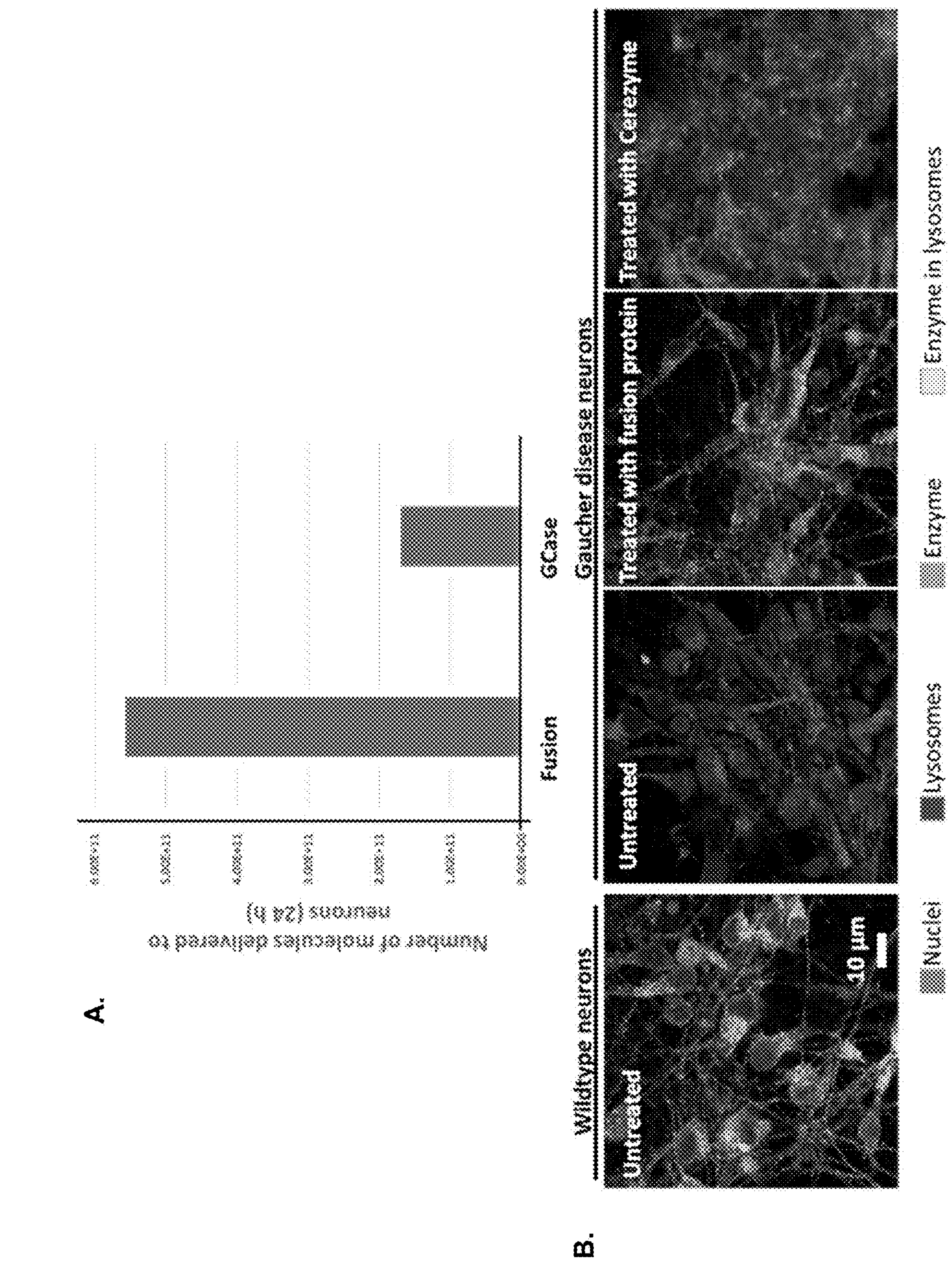
FIG. 8. Graph (A.) and fluorescence microscopy images (B.) showing, respectively, uptake and lysosomal trafficking of an ICAM-1-targeted fusion enzyme by induced pluripotent stem cells (iPS)-derived Gaucher disease neurons, compared to respective control non-targeted enzyme.

Example 8, Illustrated by FIG. 8. Uptake and lysosomal trafficking of ICAM-1-targeted fusion enzymes by neurons. (A) Induced pluripotent stem cells (iPS)-derived neurons bearing mutations from a Gaucher disease patient and treated with TNFα to mimic an inflammatory status, were incubated for 24 h at 37° C. with either targeted fusion GCase protein J in Example 1 or with control non-targeted GCase protein K in Example 1 (both after enterokinase cleavage). In both cases, these proteins had been pre-labeled with $^{125}$Iodine to trace them. The number of molecules associated to cells was quantified using a gamma counter to measure the radioactive label. (B) iPS-derived neurons bearing the wildtype GCase sequence, or, bearing Gaucher disease mutations and treated with TNFα to mimic an inflammatory status, were fixed, permeabilized and stained using fluorescently-labeled antibodies to detect lysosomes (anti-Lamp) in red color and GCase enzyme (anti-GCase) in green color. Lysosomal trafficking of these proteins appears in green+red=yellow-orange color. Cell nuclei was stained in blue using DAPI. The same procedure was used for mutant neurons after 24 h treatment with either targeted fusion GCase protein or control non-targeted Cerezyme, a commercial recombinant GCase. Scale bar=10 μm.

Figure 9:
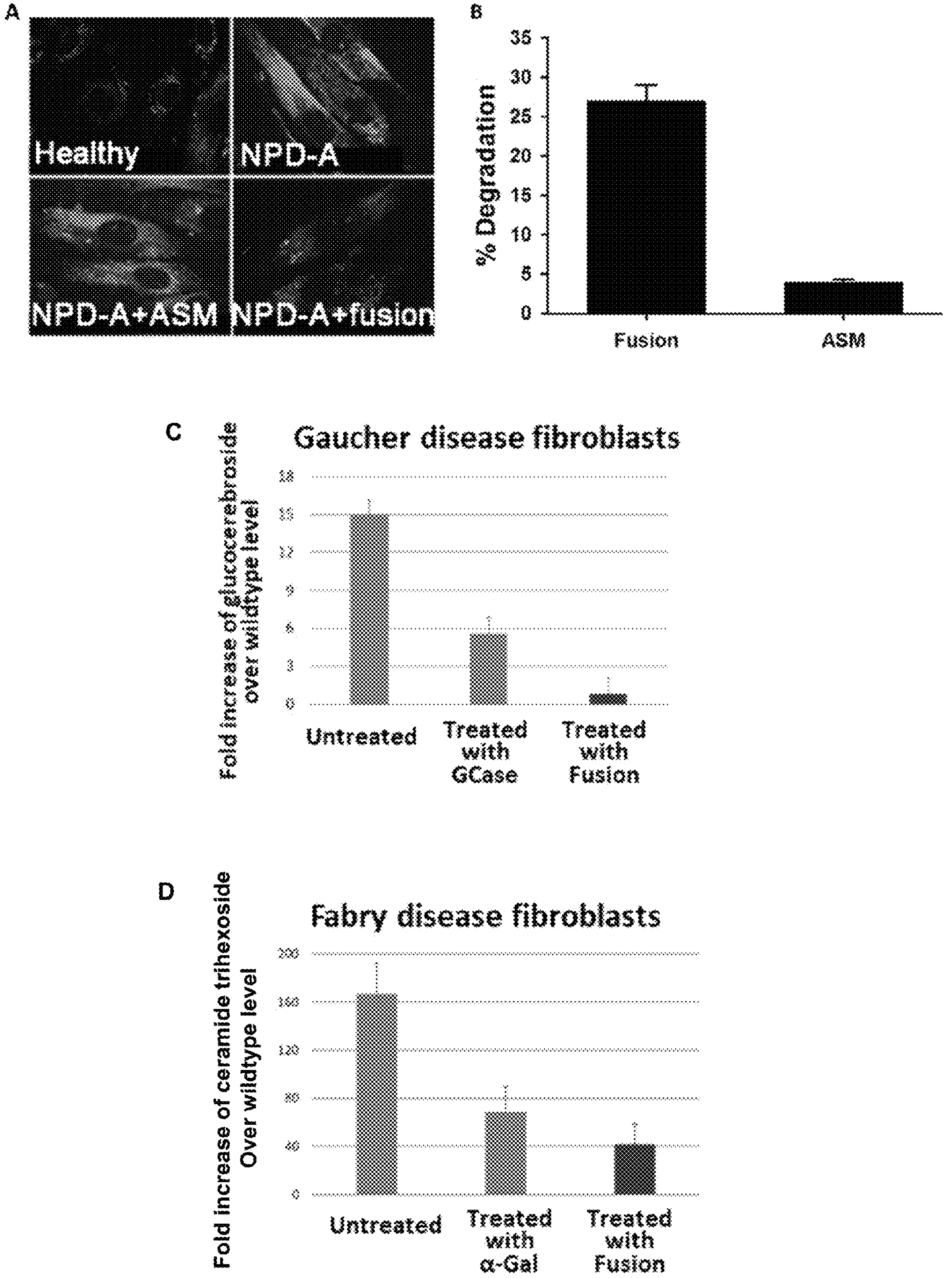
FIG. 9. Results showing reduction of lysosomal storage in patient cells (fibroblasts) by ICAM-1-targeted fusion enzymes. (A) Fluorescence microscopy images, and (B) graph showing quantification of the level of a fluorescent substrate analogue degraded by fusion protein or non-fusion control delivered to cells from a type A Niemann-Pick patient. (C), (D) Graphs showing quantifications similar to (B) in the case of fusion proteins delivered to cells from Gaucher disease and Fabry disease, respectively. In all cases, graphs show increased therapeutic degradation of the respective substrate analog by the fusion protein compared to non-targeted control.

Example 9, illustrated by FIG. 9. Reduction of lysosomal storage in patient cells by ICAM-1-targeted fusion enzymes. (A) Sphingomyelin labeling with BODIPY-FL-C12-sphingomyelin in cultured fibroblasts from healthy versus Niemann-Pick type A patient cells, prior to or after incubation with the same dose (16.7 μg/mL) of fusion ASM or non-fusion control. Sphingomyelin aberrantly accumulated in patient cells, since this is the substrate of ASM, which is deficient in these patients. (B) Quantification of the level of BODIPY-FL-C12-sphingomyelin degraded by fusion protein or non-fusion control delivered to patient cells, showing increased therapeutic degradation of the substrate by the fusion protein. (C) Fibroblasts from a Gaucher disease patient were incubated with fluorescent N-hexanoyl-NBD-glucosylceramide to visualize the accumulation of this lipid due to disease, and then left untreated or treated for 5 h with either targeted GCase fusion protein J from Example 1 or control non-targeted GCase protein K from Example 1 (both after enterokinase cleavage). The level of fluorescent N-hexanoyl-NBD-glucosylceramide in wildtype fibroblasts was also visualized and normalized to 1, so that the lipid level in untreated or treated diseased cells was compared to wild-type levels (fold increase). (D) A similar experiment to (C) is shown, yet this time tracing the accumulation of fluorescent N-Dodecanoyl-NBD-ceramide trihexoside in wildtype fibroblasts and fibroblasts from a Fabry disease patient that were either not treated or treated with α-Gal fusion protein G from Example 1 or control non-targeted α-Gal protein H from Example 1 (both after enterokinase cleavage).

Figure 10:
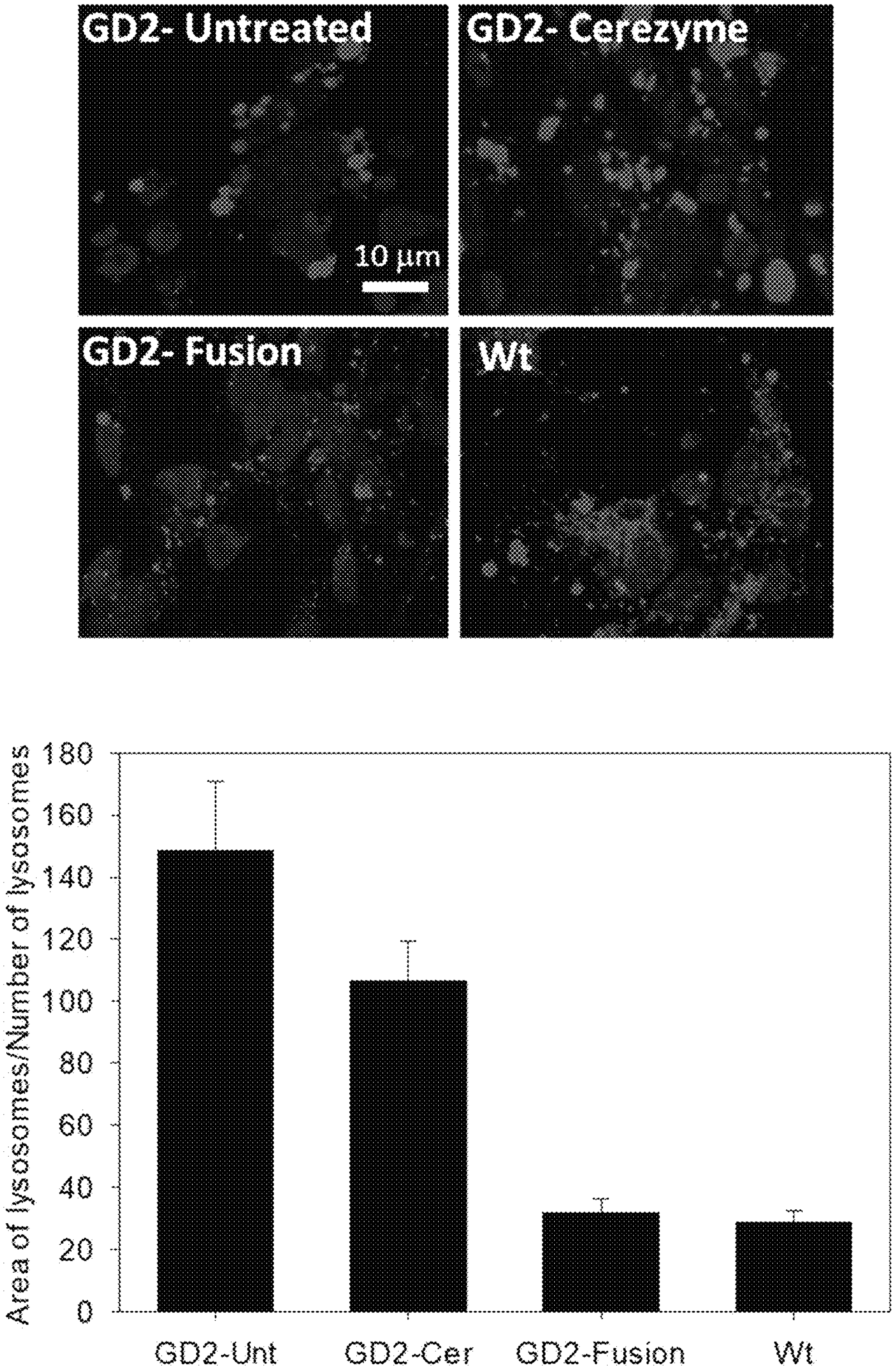
FIG. 10. Fluorescent micrographs (top) and quantification graph (bottm) showing that ICAM-1-targeted fusion enzymes normalize the size of lysosomes in Gaucher disease iPS-neurons, which are aberrantly enlarged compared to wildtype cells. Commercial Cerezyme only slightly attenuates the said lysosomal engorgement.

Example 10, illustrated by FIG. 10. Attenuation of the enlargement of lysosomes in diseased neurons by ICAM-1-targeted fusion enzymes. (A) Induced pluripotent stem cells (iPS)-derived neurons bearing wildtype GCase sequence (Wt) or bearing mutations from a Gaucher disease patient (GD2) were treated with TNFα to mimic an inflammatory status. Then, cells were left untreated (GD2-Unt) or were incubated for 24 h at 37° C. with ether targeted fusion GCase protein J in Example 1 (after enterokinase cleavage) or with commercially available Cerezyme. Lysotracker was used to label lysosomes with red fluorescence and cells were fixed. Microscopy was finally used to image lysosomes and quantify their average size (area they occupy per cell/number of lysosomal vesicles per cell).

Figure 11:
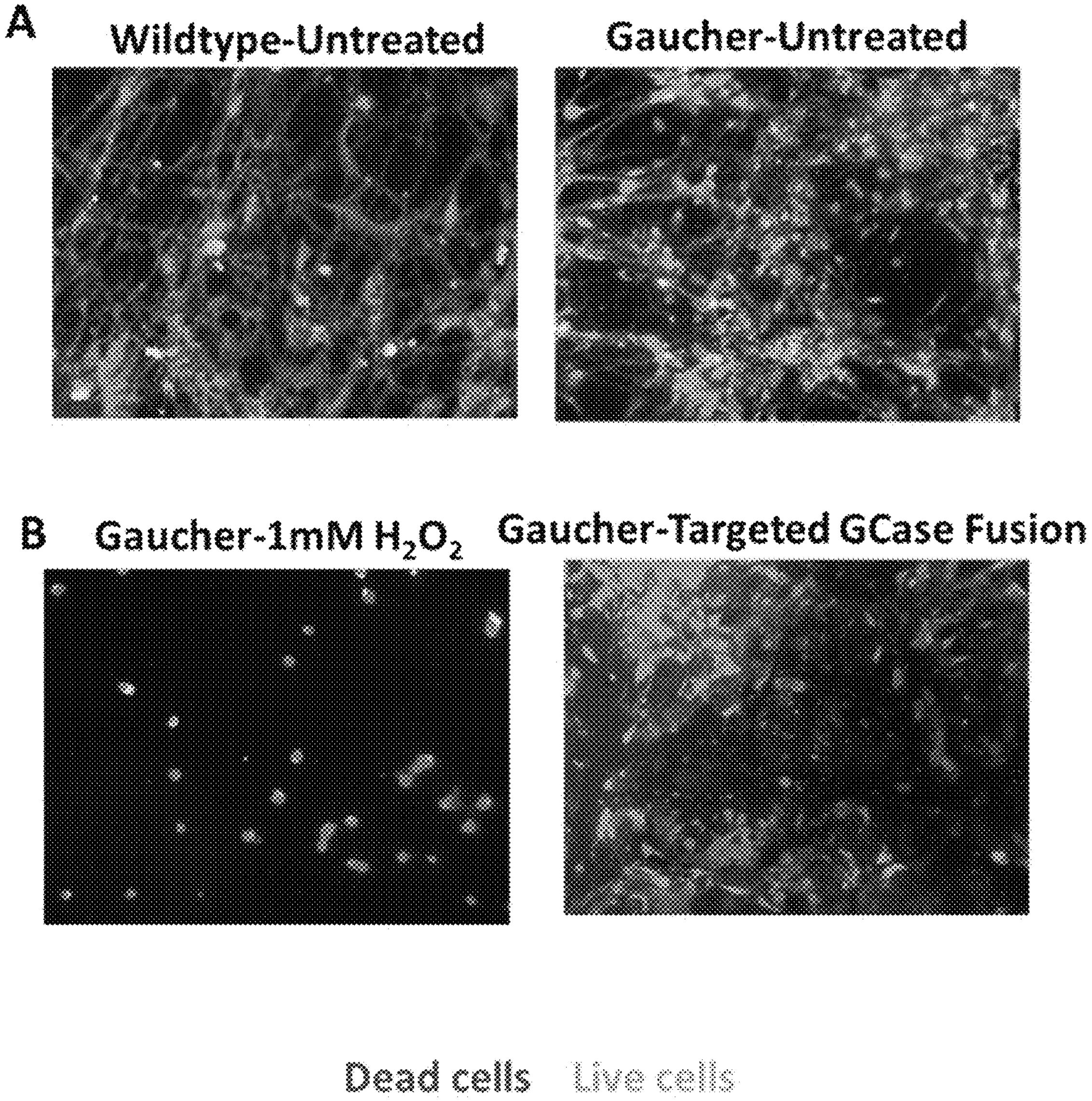
FIG. 11. Fluorescent micrographs showing lack of cytotoxicity of ICAM-1-targeted fusion proteins. (A) iPS-derived wildtype neurons compared to Gaucher disease neurons. (B) Gaucher neurons treated with control hydrogen peroxide, which is known to be cytotoxic, or with fusion protein.

Example 11, illustrated by FIG. 11. Lack of cytotoxicity of ICAM-1-targeted fusion proteins. (A) Induced pluripotent stem cells (iPS)-derived neurons bearing wildtype GCase sequence or bearing Gaucher patient mutations were treated with TNFα overnight to mimic an inflammatory status. The number of live cells or dead cells were visualized using a live/dead viability assay where calcein stains the cytoplasm of live cells green while ethidium homodimer stains dead cell nuclei red, respectively. (B) Similarly, neurons bearing Gaucher patient mutations were incubated with 1 mM $H_2O_2$ for 1 h to induce cell death as a control or for 48 h with targeted GCase fusion protein J in example 1 (after enterokinase cleavage), then the same live/dead assay was used.

Figure 12:
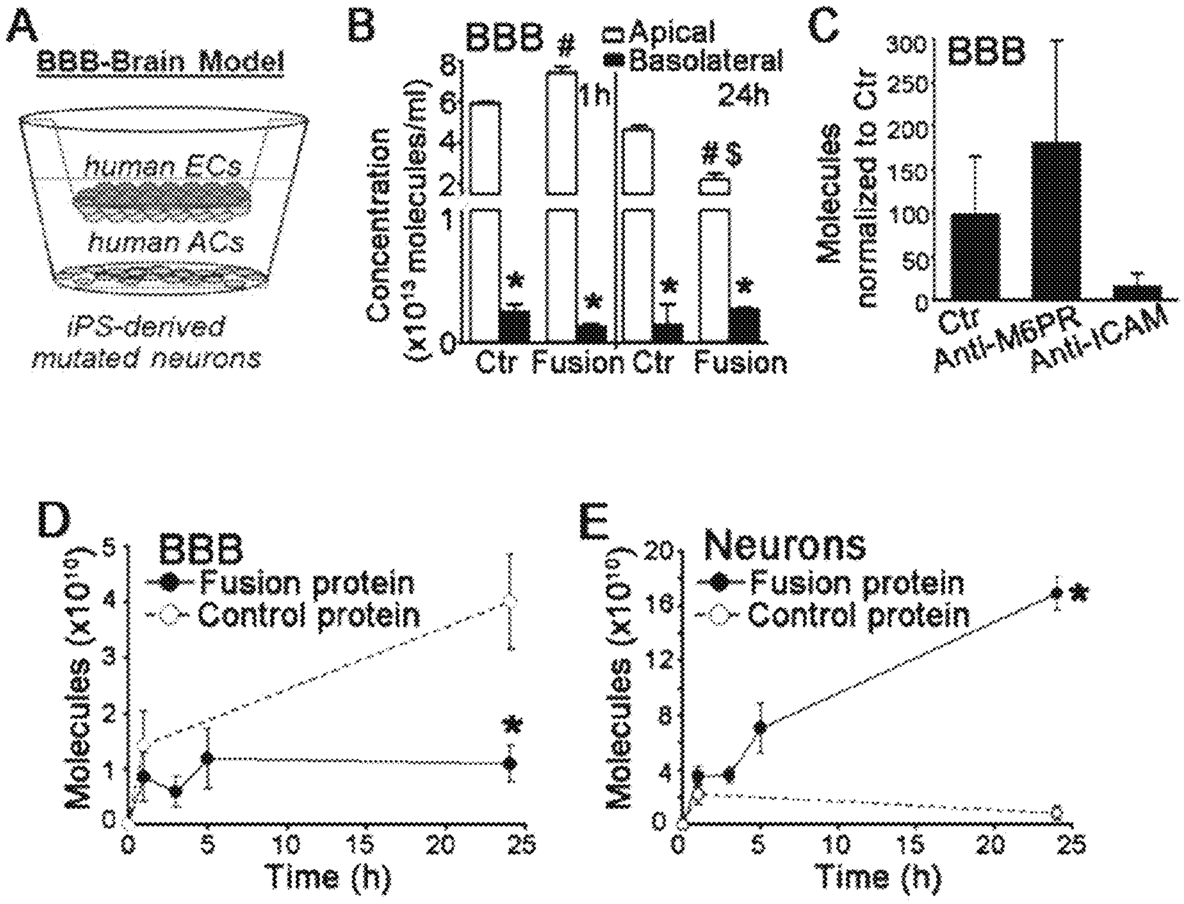
FIG. 12. Model and graphical results showing transcytosis of ICAM-1-targeted fusion enzymes across models of the blood-brain barrier (BBB) and uptake by subjacent neurons. (A) Multi-cellular Transwell model. (B) Graph showing the concentration of fusion protein or control non-targeted enzyme in the apical or basolateral transwell chambers, demonstrating barrier function. (C) Graph showing that ICAM-1 blockage reduces the amount of fusion protein that interacted with the BBB. (D) Graph showing much higher BBB entrapment of the non-targeted enzyme compared to respective fusion protein. (E) Graph showing much higher uptake of fusion protein by Gaucher disease neurons compared to non-targeted enzyme.

Example 12, illustrated by FIG. 12. Transcytosis of ICAM-1-targeted fusion enzymes across models of the blood-brain barrier and uptake by subjacent neurons. (A) Transwell model of the blood-brain barrier formed by human brain endothelial cells growing on the apical side of a porous filter, astrocytes growing on the basolateral side of the same filter, and these two cellular monolayers separating an apical chamber (mimicking the blood vessel side) from a basolateral chamber (mimicking the brain tissue side). These cells were treated with conduritol-β-epoxide to mimic a Gaucher disease phenotype. Induced pluripotent stem cells (iPS)-derived neurons bearing mutations from a Gaucher disease patient were grown on the bottom of the basolateral chamber. Cells were additionally treated with TNFα to mimic an inflammatory status typical of this disease. (B) ICAM-1 targeted fusion GCase protein J (example 1; after enterokinase cleavage) or control (Ctr) non-targeted GCase protein K (example 1; after enterokinase cleavage) were pre-labeled with $^{125}$Iodine for tracing purposes and added to the apical chamber above the BBB for 1 h or 24 h. After this time, the amount of proteins in the apical or in the basolateral chambers was quantified. The graph shows the concentration of protein molecules left in either chamber, demonstrating the lack of free diffusion or leakage across this BBB model, which can thus be considered a good barrier model. (C) The amount of targeted fusion GCase that interacted with the BBB was quantified after 3 h and compared to the amount of targeted fusion GCase interacting the BBB when cells had been pre-incubated with anti-mannose-6-phosphate receptor or anti-ICAM receptor to block the respective receptor. (D) Presence of fusion GCase protein or control GCase in the BBB or (E) basolateral iPS-neurons over time. Data are average±SEM,* $p<0.05$ (Student's t-test).

Figure 13:
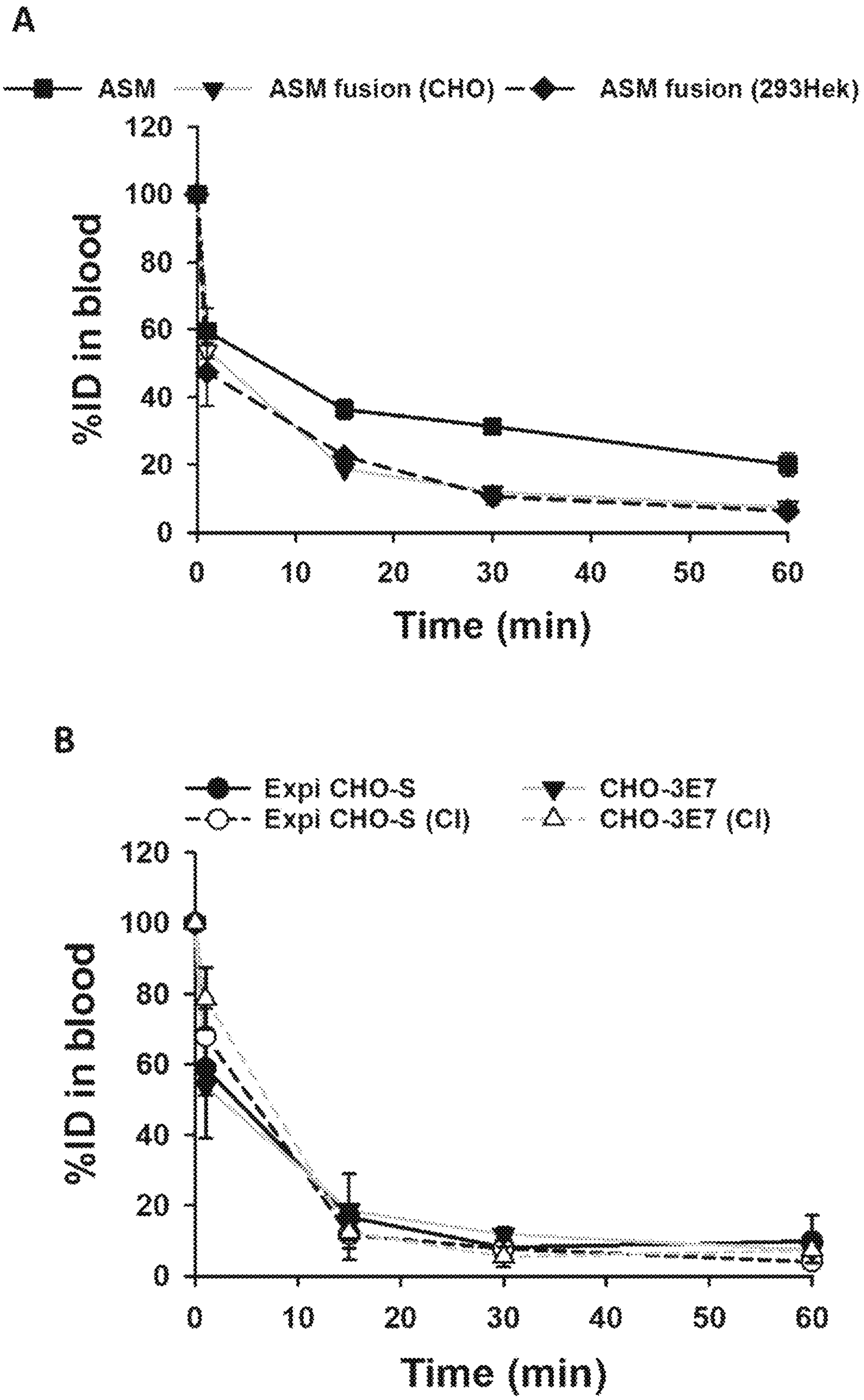
FIG. 13. Graphs showing circulation of ICAM-1-targeted fusion enzymes in mice. (A) A fusion protein produced in two different cell sources compared to a non-targeted enzyme from which Olipudase® is derived. (B) Circulation of the same fusion protein from two different cell sources, before and after cleavage (Cl) of the His-tag domain.

Example 13, illustrated by FIG. 13. Circulation of ICAM-1-targeted fusion enzymes in mice. Blood levels of proteins labeled with $^{125}$Iodine, expressed as a percentage of the injected dose (0.13 mg/Kg), determined at the indicated times after their intravenous injection in ASM knockout mice, the model for Niemann-Pick disease type A and B. (A) Fusion protein B in Example 1, produced from two different cell sources (CHO-3E7 versus Hek 293 cells) is compared to full recombinant ASM produced by He et. al. (He, Miranda et al. 1999), which served as basis for Genzyme's Olipudase®. Faster disappearance of fusion proteins is expected due to targeting to tissues, and should be beneficial in lowering systemic side effects and resistance due to immunorecognition. (B) Circulation of the same fusion in two different CHO cell lines, before and after cleavage (Cl) of the His-tag domain by enterokinase.

Figure 14:
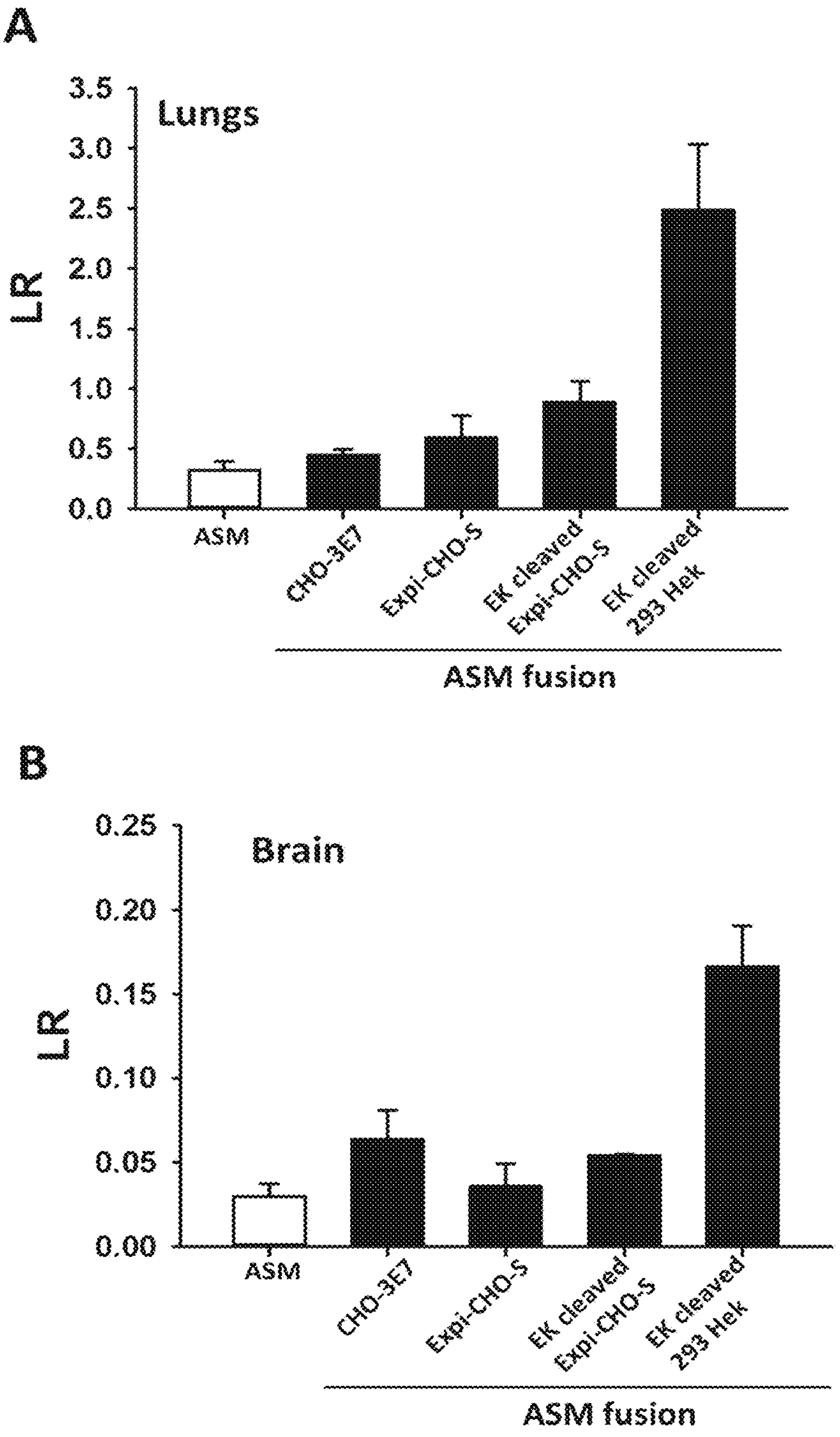
FIG. 14. Graphs showing enhanced (A) lung and (B) brain distribution of ICAM-1-targeted fusion enzymes in mice compared to non-targeted enzyme.

Example 14, illustrated by FIG. 14. Lung and brain distribution of ICAM-1-targeted fusion enzymes in mice. (A) Lung and (B) brain levels of proteins labeled with $^{125}$Iodine, expressed as the localization ratio (LR), 60 minutes after intravenous injection of 0.13 mg/Kg in mice (lung and brain are main targets for Niemann-Pick disease type B and A, respectively). Fusion protein B in Example 1, produced from three cell sources (CHO-3E7, Expi-CHO-S versus Hek 293 cells), prior or after cleavage with enterokinase (EK) to remove His-tag, is compared to full recombinant ASM produced by He et. al. (He, Miranda et al. 1999), which served as basis for Genzyme's Olipudase®. Enhanced targeting is shown for all fusion protein.

Figure 15:
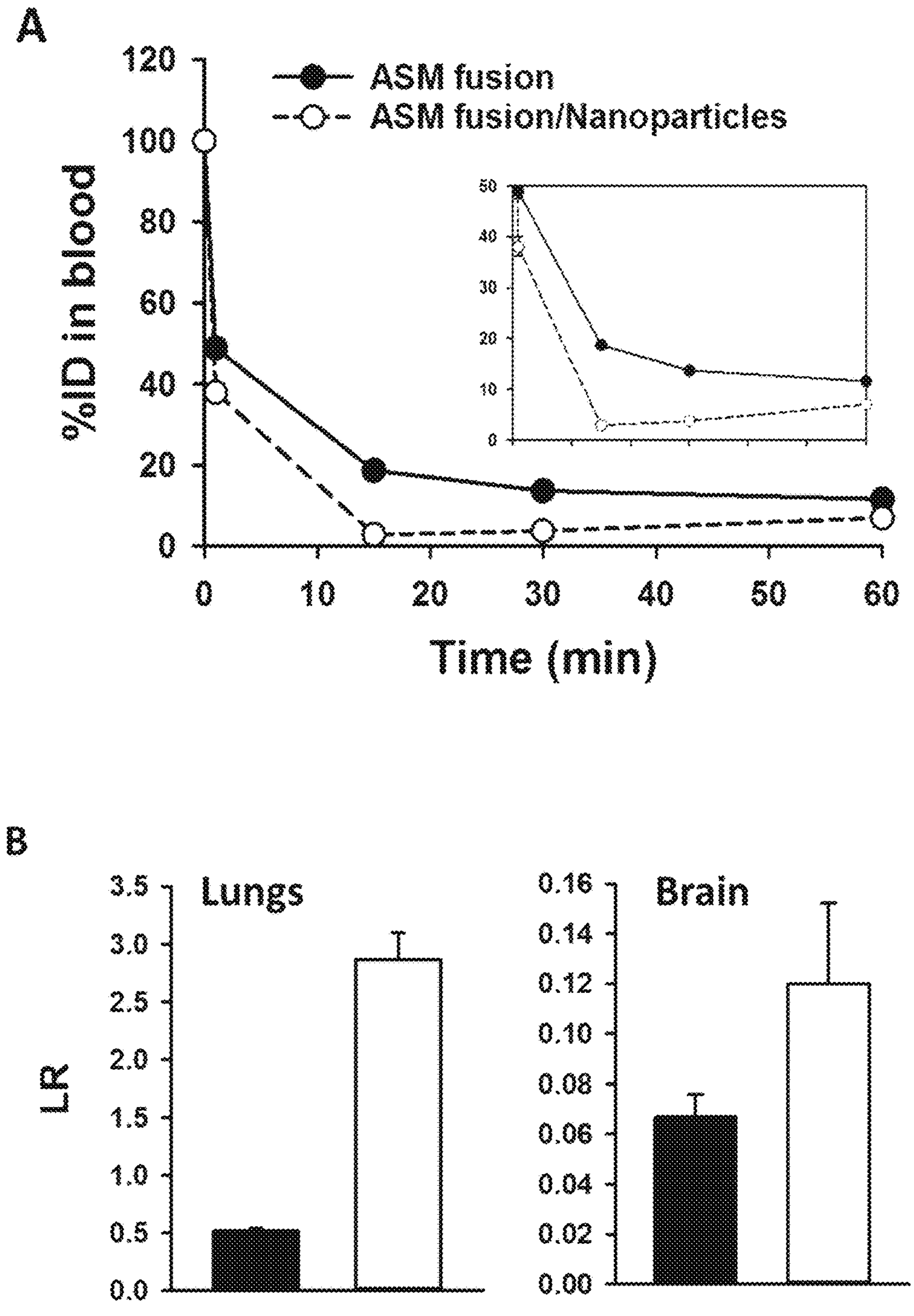
FIG. 15. Graphs showing (A) higher blood levels and (B) lower lung and (C) brain levels of a fusion protein injected as such in mice compared to the same fusion protein loaded in a nanoparticle formulation.

Example 15, illustrated by FIG. 15. Lung and brain distribution of ICAM-1-targeted fusion enzymes administered in mice as nanoparticle formulations. (A) Blood levels of a "naked" fusion protein compared to a fusion protein loaded in a nanoparticle formulation, determined at the indicated times after their intravenous injection and expressed as a percentage of the injected dose (% ID) in blood. The nanoparticle formulation had faster disappearance (the inset shows a close up of the large graph for additional detail), which is expected due to the increase targeting to tissues (see B) and should be beneficial in lowering any potential systemic side effects of the fusion protein. and resistance due to immunorecognition. (B) Lung and brain levels of "naked" versus nanoparticle-loaded fusion protein, expressed as the localization ratio (LR) found 60 min after injection (lung and brain are main targets for Niemann-Pick disease type B and A, respectively). The nanoparticle formulation showed 5-6 fold enhanced lung accumulation and 2-fold enhanced brain accumulation.

Figure 16:
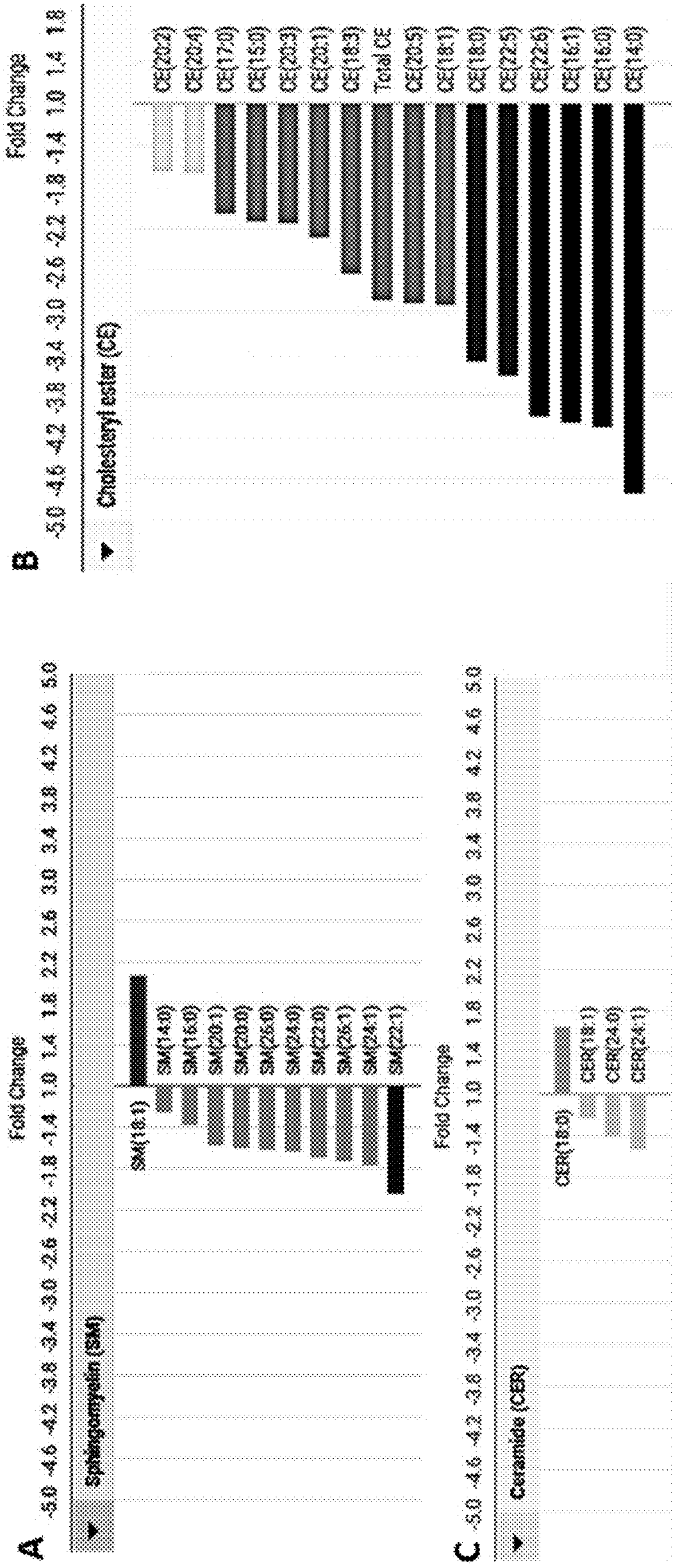
FIG. 16. Graphs showing brain effects of ICAM-1-targeted fusion enzymes in mice following an every other day dosing schedule over a two week period. (A) Sphingomyelin (SM), the substrate of the ASM enzyme, which aberrantly accumulates in the brain of diseased mice (as in humans) was measured to be reduced upon treatment. (B) Esterified cholesterol (CE), which associates to sphingomyelin and also accumulates in the disease, was also measured to be reduced by fusion enzyme treatment. (C) Ceramide (CER), the product of the ASM catalytic reaction, which accumulates and causes side effects by Olipudase®, was determined.

Example 16, illustrated by FIG. 16. Brain effects of ICAM-1-targeted fusion enzymes in mice. ASM knockout mice were injected with 0.6 mg/Kg of enterokinase cleaved fusion protein B in Example 1 every two days, for a total of 6 injections, and were compared to mice injected with vehicle buffer but no fusion protein (sham control). At the end of the experiment, (A) sphingomyelin (SM), the substrate of the ASM enzyme, which aberrantly accumulates in the brain of diseased mice (as in humans) was measured. (B) Cholesterol (CE), which associates to sphingomyelin and also accumulates in the disease, was also measured. (C) Ceramide (CER), the product of the ASM catalytic reaction, which accumulates and causes side effects by Olipudase®, was determined. In all cases, increases of SM, CE, or CER are marked as a positive fold change (bar on the right of the middle line), while decreases are marked as a negative fold change (bars on the left of the middle line). Middle lines are non-treated diseased controls. Both SM and CE were significantly lowered, without dangerous.

Figure 17:
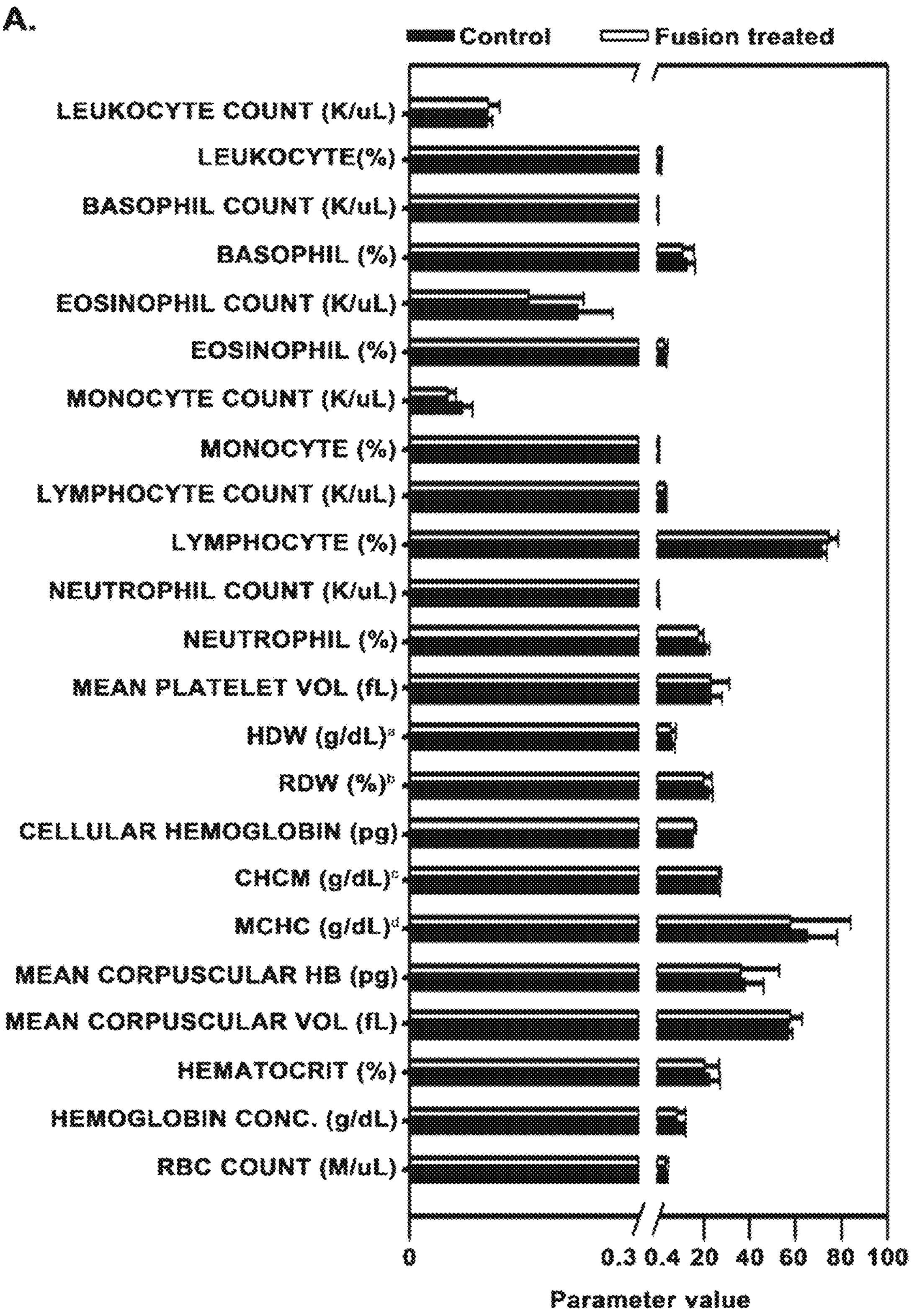
FIG. 17. Graphs showing side effects of ICAM-1-targeted fusion enzymes in mice. (A.) Hematology parameters, (B.) markers of liver and kidney toxicity, (C.) body weight, and (D.) behavior, none showed signs of toxicity.
Figure 17:
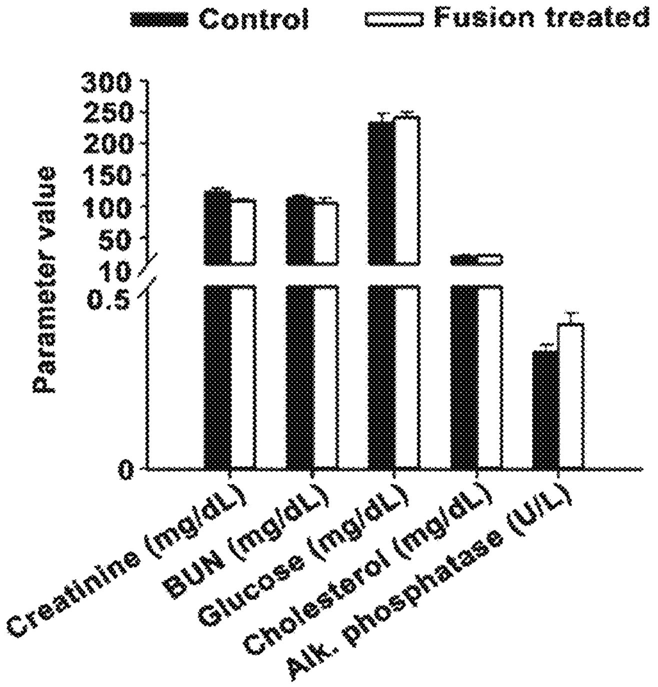
Figure 17:
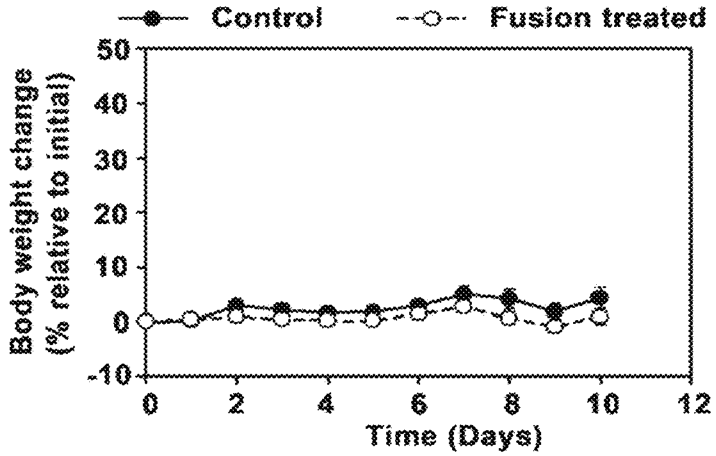

Example 17, illustrated by FIG. 17. Side effects of ICAM-1-targeted fusion enzymes in mice. The same animals shown in example 16 were examined for side effects, including: (A) hematology parameters, (B) markers of liver and kidney toxicity, (C) body weight, and (D) behavior. In terms of all the parameters tested, treatment with the fusion protein did not induce toxicity compared to the sham treated group (control).

It will be recognized from the foregoing description and figures that the strategy described herein provides improved results in peripheral organs, which are the main target for type B NPD and many other LSDs. This is expected to help lower the dose required for therapeutic activity in these organs with concomitant decrease in cost and side effects, which benefits both drug manufacturers and patients, and can be extended from NPD to all current lysosomal ERTs used for peripheral organ treatment. In addition, the present fusion protein strategy exhibits enhanced targeting and measurable functional effects in the brain, a non-peripheral organ of the central nervous system where no current lysosomal ERT can reach. Thus, this strategy represents a breakthrough in the treatment of type A NPD and is applicable to ≈40 additional LSDs with neurological syndromes. Lastly, unlike previous nanoparticulate formulations, which involved polymeric materials that have never been approved for chronic use in pediatric patients, the fusion protein platform described herein can be produced by classical biotechnological means, as done for current ERTs approved by FDA. Reproducibility, high yield and purity, and versatility of production in different cells supports manufacturing and reduces regulatory hurdles for implementing embodiments of the disclosure.

The following sequences are representative and non-limiting examples of embodiments of the disclosure, and relate to the constructs depicted in FIG. 1, and to the results described herein.

```
Sequence 1. Amino acid sequence of the ICAM-1 targeting segment, 2γ3.
NNQKIVNIKEKVAQIEA (SEQ ID NO: 1)

Sequence 2. cDNA sequence of the expression cassette for human acid sphingomyelinase
(ASM) with one copy of the 2γ3 ICAM-1-targeting peptide at the amino terminus
ATGGAGACCGACACACTGCTCCTGTGGGTCCTGCTCCTCTGGGTGCCAGGAAGTACAGGAGAT
CACCATCACCATCACCACGACGACGACGACAAGAATAACCAAAAGATTGTGAATATCAAAGAG
AAAGTGGCTCAGATTGAGGCTGGAGGCGGAGGAAGCGGCGGCGGAGGAAGCGGATTTCTGGGA
CACCCTCTTTCTCCCCAAGGCCATCCTGCCAGGTTACATCGCATAGTGCCCCGGCTCCGAGAT
GTCTTTGGGTGGGGGAACCTCACCTGCCCAATCTGCAAAGGTCTATTCACCGCCATCAACCTC
GGGCTGAAGAAGGAACCCAATGTGGCTCGCGTGGGCTCCGTGGCCATCAAGCTGTGCAATCTG
CTGAAGATAGCACCACCTGCCGTGTGCCAATCCATTGTCCACCTCTTTGAGGATGACATGGTG
GAGGTGTGGAGACGCTCAGTGCTGAGCCCATCTGAGGCCTGTGGCCTGCTCCTGGGCTCCACC
TGTGGGCACTGGGACATTTTCTCATCTTGGAACATCTCTTTGCCTACTGTGCCGAAGCCGCCC
CCCAAACCCCCTAGCCCCCCAGCCCCAGGTGCCCCTGTCAGCCGCATCCTCTTCCTCACTGAC
CTGCACTGGGATCATGACTACCTGGAGGGCACGGACCCTGACTGTGCAGACCCACTGTGCTGC
CGCCGGGGTTCTGGCCTGCCGCCCGCATCCCGGCCAGGTGCCGGATACTGGGGCGAATACAGC
AAGTGTGACCTGCCCCTGAGGACCCTGGAGAGCCTGTTGAGTGGGCTGGGCCCAGCCGGCCCT
TTTGATATGGTGTACTGGACAGGAGACATCCCCGCACATGATGTCTGGCACCAGACTCGTCAG
GACCAACTGCGGGCCCTGACCACCGTCACAGCACTTGTGAGGAAGTTCCTGGGGCCAGTGCCA
GTGTACCCTGCTGTGGGTAACCATGAAAGCACACCTGTCAATAGCTTCCCTCCCCCCTTCATT
GAGGGCAACCACTCCTCCCGCTGGCTCTATGAAGCGATGGCCAAGGCTTGGGAGCCCTGGCTG
```

-continued

CCTGCCGAAGCCCTGCGCACCCTCAGAATTGGGGGGTTCTATGCTCTTTCCCCATACCCCGGT
CTCCGCCTCATCTCTCTCAATATGAATTTTTGTTCCCGTGAGAACTTCTGGCTCTTGATCAAC
TCCACGGATCCCGCAGGACAGCTCCAGTGGCTGGTGGGGGAGCTTCAGGCTGCTGAGGATCGA
GGAGACAAAGTGCATATAATTGGCCACATTCCCCCAGGGCACTGTCTGAAGAGCTGGAGCTGG
AATTATTACCGAATTGTAGCCAGGTATGAGAACACCCTGGCTGCTCAGTTCTTTGGCCACACT
CATGTGGATGAATTTGAGGTCTTCTATGATGAAGAGACTCTGAGCCGGCCGCTGGCTGTAGCC
TTCCTGGCACCCAGTGCAACTACCTACATCGGCCTTAATCCTGGTTACCGTGTGTACCAAATA
GATGGAAACTACTCCGGGAGCTCTCACGTGGTCCTGGACCATGAGACCTACATCCTGAATCTG
ACCCAGGCAAACATACCGGGAGCCATACCGCACTGGCAGCTTCTCTACAGGGCTCGAGAAACC
TATGGGCTGCCCAACACACTGCCTACCGCCTGGCACAACCTGGTATATCGCATGCGGGGCGAC
ATGCAACTTTTCCAGACCTTCTGGTTTCTCTACCATAAGGGCCACCCACCCTCGGAGCCCTGT
GGCACGCCCTGCCGTCTGGCTACTCTTTGTGCCCAGCTCTCTGCCCGTGCTGACAGCCCTGCT
CTGTGCCGCCACCTGATGCCAGATGGGAGCCTCCCAGAGGCCCAGAGCCTGTGGCCAAGGCCA
CTGTTTTGCTAG (SEQ ID NO: 2)

Sequence 3. cDNA sequence of the expression cassette for human ASM with five tandem-repeats of the 2γ3 ICAM-1-targeting peptide at the amino terminus.

ATGGAGACCGACACACTGCTCCTGTGGGTCCTGCTCCTCTGGGTGCCAGGAAGTACAGGAGA
TCACCATCACCATCACCACGACGACGACGACAAGAATAACCAAAAGATTGTGAATATCAAAG
AGAAAGTGGCTCAGATTGAGGCTGGAGGCGGAGGAAGCGGCGGCGGAGGAAGCAATAATCAG
AAAATCGTCAACATTAAGGAAAAGGTCGCCCAGATTGAAGCAGGAGGCGGCGGCAGCGGCGG
AGGCGGAAGCAATAATCAGAAGATTGTTAACATCAAAGAAAAGGTGGCCCAAATTGAAGCAG
GAGGAGGAGGATCTGGAGGCGGAGGCAGCAATAACCAGAAGATCGTCAACATCAAGGAAAAG
GTGGCTCAGATCGAGGCAGGAGGCGGAGGAAGCGGAGGGGGCGGCTCTAACAACCAGAAAAT
CGTGAACATCAAAGAGAAAGTGGCTCAGATCGAAGCCGGCGGAGGAGGATCCGGAGGAGGAG
GAAGCGGATTTCTGGGACACCCTCTTTCTCCCCAAGGCCATCCTGCCAGGTTACATCGCATA
GTGCCCCGGCTCCGAGATGTCTTTGGGTGGGGGAACCTCACCTGCCCAATCTGCAAAGGTCT
ATTCACCGCCATCAACCTCGGGCTGAAGAAGGAACCCAATGTGGCTCGCGTGGGCTCCGTGG
CCATCAAGCTGTGCAATCTGCTGAAGATAGCACCACCTGCCGTGTGCCAATCCATTGTCCAC
CTCTTTGAGGATGACATGGTGGAGGTGTGGAGACGCTCAGTGCTGAGCCCATCTGAGGCCTG
TGGCCTGCTCCTGGGCTCCACCTGTGGGCACTGGGACATTTTCTCATCTTGGAACATCTCTT
TGCCTACTGTGCCGAAGCCGCCCCCAAACCCCCTAGCCCCCCAGCCCCAGGTGCCCCTGTC
AGCCGCATCCTCTTCCTCACTGACCTGCACTGGGATCATGACTACCTGGAGGGCACGGACCC
TGACTGTGCAGACCCACTGTGCTGCCGCCGGGGTTCTGGCCTGCCGCCCGCATCCCGGCCAG
GTGCCGGATACTGGGGCGAATACAGCAAGTGTGACCTGCCCCTGAGGACCCTGGAGAGCCTG
TTGAGTGGGCTGGGCCCAGCCGGCCCTTTTGATATGGTGTACTGGACAGGAGACATCCCCGC
ACATGATGTCTGGCACCAGACTCGTCAGGACCAACTGCGGGCCCTGACCACCGTCACAGCAC
TTGTGAGGAAGTTCCTGGGGCCAGTGCCAGTGTACCCTGCTGTGGGTAACCATGAAAGCACA
CCTGTCAATAGCTTCCCTCCCCCCTTCATTGAGGGCAACCACTCCTCCCGCTGGCTCTATGA
AGCGATGGCCAAGGCTTGGGAGCCCTGGCTGCCTGCCGAAGCCCTGCGCACCCTCAGAATTG
GGGGGTTCTATGCTCTTTCCCCATACCCCGGTCTCCGCCTCATCTCTCTCAATATGAATTTT
TGTTCCCGTGAGAACTTCTGGCTCTTGATCAACTCCACGGATCCCGCAGGACAGCTCCAGTG
GCTGGTGGGGGAGCTTCAGGCTGCTGAGGATCGAGGAGACAAAGTGCATATAATTGGCCACA
TTCCCCCAGGGCACTGTCTGAAGAGCTGGAGCTGGAATTATTACCGAATTGTAGCCAGGTAT
GAGAACACCCTGGCTGCTCAGTTCTTTGGCCACACTCATGTGGATGAATTTGAGGTCTTCTA
TGATGAAGAGACTCTGAGCCGGCCGCTGGCTGTAGCCTTCCTGGCACCCAGTGCAACTACCT
ACATCGGCCTTAATCCTGGTTACCGTGTGTACCAAATAGATGGAAACTACTCCGGGAGCTCT
CACGTGGTCCTGGACCATGAGACCTACATCCTGAATCTGACCCAGGCAAACATACCGGGAGC
CATACCGCACTGGCAGCTTCTCTACAGGGCTCGAGAAACCTATGGGCTGCCCAACACACTGC
CTACCGCCTGGCACAACCTGGTATATCGCATGCGGGGCGACATGCAACTTTTCCAGACCTTC
TGGTTTCTCTACCATAAGGGCCACCCACCCTCGGAGCCCTGTGGCACGCCCTGCCGTCTGGC
TACTCTTTGTGCCCAGCTCTCTGCCCGTGCTGACAGCCCTGCTCTGTGCCGCCACCTGATGC
CAGATGGGAGCCTCCCAGAGGCCCAGAGCCTGTGGCCAAGGCCACTGTTTTGCTAG (SEQ ID NO: 3)

Sequence 4. cDNA sequence of the expression cassette for human ASM with ten tandem-repeats of the 2γ3 ICAM-1-targeting peptide at the amino terminus.

ATGGAGACCGACACACTGCTCCTGTGGGTCCTGCTCCTCTGGGTGCCAGGAAGTACAGGAGA
TCACCATCACCATCACCACGACGACGACGACAAGAATAACCAAAAGATTGTGAATATCAAAG
AGAAAGTGGCTCAGATTGAGGCTGGAGGCGGAGGAAGCGGCGGCGGAGGAAGCAATAATCAG
AAAATCGTCAACATTAAGGAAAAGGTCGCCCAGATTGAAGCAGGAGGCGGCGGCAGCGGCGG
AGGCGGAAGCAATAATCAGAAGATTGTTAACATCAAAGAAAAGGTGGCCCAAATTGAAGCAG
GAGGAGGAGGATCTGGAGGCGGAGGCAGCAATAACCAGAAGATCGTCAACATCAAGGAAAAG
GTGGCTCAGATCGAGGCAGGAGGCGGAGGAAGCGGAGGGGGCGGCTCTAACAACCAGAAAAT
CGTGAACATCAAAGAGAAAGTGGCTCAGATCGAAGCCGGCGGAGGAGGATCCGGAGGAGGAG
GAAGCAATAACCAAAAGATTGTGAATATCAAAGAGAAAGTGGCTCAGATTGAGGCTGGAGGC
GGAGGAAGCGGCGGCGGAGGAAGCAATAATCAGAAAATCGTCAACATTAAGGAAAAGGTCGC
CCAGATTGAAGCAGGAGGCGGCGGCAGCGGCGGAGGCGGAAGCAATAATCAGAAGATTGTTA
ACATCAAAGAAAAGGTGGCCCAAATTGAAGCAGGAGGAGGAGGATCTGGAGGCGGAGGCAGC
AATAACCAGAAGATCGTCAACATCAAGGAAAAGGTGGCTCAGATCGAGGCAGGAGGCGGAGG
AAGCGGAGGGGGCGGCTCTAACAACCAGAAAATCGTGAACATCAAAGAGAAAGTGGCTCAGA
TCGAAGCCGGCGGAGGAGGATCCGGAGGAGGAGGAAGCGGATTTCTGGGACACCCTCTTTCT
CCCCAAGGCCATCCTGCCAGGTTACATCGCATAGTGCCCCGGCTCCGAGATGTCTTTGGGTG
GGGGAACCTCACCTGCCCAATCTGCAAAGGTCTATTCACCGCCATCAACCTCGGGCTGAAGA
AGGAACCCAATGTGGCTCGCGTGGGCTCCGTGGCCATCAAGCTGTGCAATCTGCTGAAGATA
GCACCACCTGCCGTGTGCCAATCCATTGTCCACCTCTTTGAGGATGACATGGTGGAGGTGTG
GAGACGCTCAGTGCTGAGCCCATCTGAGGCCTGTGGCCTGCTCCTGGGCTCCACCTGTGGGC
ACTGGGACATTTTCTCATCTTGGAACATCTCTTTGCCTACTGTGCCGAAGCCGCCCCCCAAA
CCCCCTAGCCCCCCAGCCCCAGGTGCCCCTGTCAGCCGCATCCTCTTCCTCACTGACCTGCA

-continued

CTGGGATCATGACTACCTGGAGGGCACGGACCCTGACTGTGCAGACCCACTGTGCTGCCGCC
GGGGTTCTGGCCTGCCGCCCGCATCCCGGCCAGGTGCCGGATACTGGGGCGAATACAGCAAG
TGTGACCTGCCCCTGAGGACCCTGGAGAGCCTGTTGAGTGGGCTGGGCCCAGCCGGCCCTTT
TGATATGGTGTACTGGACAGGAGACATCCCCGCACATGATGTCTGGCACCAGACTCGTCAGG
ACCAACTGCGGGCCCTGACCACCGTCACAGCACTTGTGAGGAAGTTCCTGGGGCCAGTGCCA
GTGTACCCTGCTGTGGGTAACCATGAAAGCACACCTGTCAATAGCTTCCCTCCCCCCTTCAT
TGAGGGCAACCACTCCTCCCGCTGGCTCTATGAAGCGATGGCCAAGGCTTGGGAGCCCTGGC
TGCCTGCCGAAGCCCTGCGCACCCTCAGAATTGGGGGGTTCTATGCTCTTTCCCCATACCCC
GGTCTCCGCCTCATCTCTCTCAATATGAATTTTTGTTCCCGTGAGAACTTCTGGCTCTTGAT
CAACTCCACGGATCCCGCAGGACAGCTCCAGTGGCTGGTGGGGGAGCTTCAGGCTGCTGAGG
ATCGAGGAGACAAAGTGCATATAATTGGCCACATTCCCCCAGGGCACTGTCTGAAGAGCTGG
AGCTGGAATTATTACCGAATTGTAGCCAGGTATGAGAACACCCTGGCTGCTCAGTTCTTTGG
CCACACTCATGTGGATGAATTTGAGGTCTTCTATGATGAAGAGACTCTGAGCCGGCCGCTGG
CTGTAGCCTTCCTGGCACCCAGTGCAACTACCTACATCGGCCTTAATCCTGGTTACCGTGTG
TACCAAATAGATGGAAACTACTCCGGGAGCTCTCACGTGGTCCTGGACCATGAGACCTACAT
CCTGAATCTGACCCAGGCAAACATACCGGGAGCCATACCGCACTGGCAGCTTCTCTACAGGG
CTCGAGAAACCTATGGGCTGCCCAACACACTGCCTACCGCCTGGCACAACCTGGTATATCGC
ATGCGGGGCGACATGCAACTTTTCCAGACCTTCTGGTTTCTCTACCATAAGGGCCACCCACC
CTCGGAGCCCTGTGGCACGCCCTGCCGTCTGGCTACTCTTTGTGCCCAGCTCTCTGCCCGTG
CTGACAGCCCTGCTCTGTGCCGCCACCTGATGCCAGATGGGAGCCTCCCAGAGGCCCAGAGC
CTGTGGCCAAGGCCACTGTTTTGCTAG (SEQ ID NO: 4)

Sequence 5. cDNA sequence of the expression cassette for human ASM with five tandem-repeats of the 2γ3 ICAM-1-targeting peptide at the carboxyl terminus.

ATGGAGACCGACACACTGCTCCTGTGGGTCCTGCTCCTCTGGGTGCCAGGAAGTACAGGAGA
TCACCATCACCATCACCACGACGACGACGACAAGCACCCTCTTTCTCCCCAAGGCCATCCTG
CCAGGTTACATCGCATAGTGCCCCGGCTCCGAGATGTCTTTGGGTGGGGGAACCTCACCTGC
CCAATCTGCAAAGGTCTATTCACCGCCATCAACCTCGGGCTGAAGAAGGAACCCAATGTGGC
TCGCGTGGGCTCCGTGGCCATCAAGCTGTGCAATCTGCTGAAGATAGCACCACCTGCCGTGT
GCCAATCCATTGTCCACCTCTTTGAGGATGACATGGTGGAGGTGTGGAGACGCTCAGTGCTG
AGCCCATCTGAGGCCTGTGGCCTGCTCCTGGGCTCCACCTGTGGGCACTGGGACATTTTCTC
ATCTTGGAACATCTCTTTGCCTACTGTGCCGAAGCCGCCCCCCAAACCCCCTAGCCCCCCAG
CCCCAGGTGCCCCTGTCAGCCGCATCCTCTTCCTCACTGACCTGCACTGGGATCATGACTAC
CTGGAGGGCACGGACCCTGACTGTGCAGACCCACTGTGCTGCCGCCGGGGTTCTGGCCTGCC
GCCCGCATCCCGGCCAGGTGCCGGATACTGGGGCGAATACAGCAAGTGTGACCTGCCCCTGA
GGACCCTGGAGAGCCTGTTGAGTGGGCTGGGCCCAGCCGGCCCTTTTGATATGGTGTACTGG
ACAGGAGACATCCCCGCACATGATGTCTGGCACCAGACTCGTCAGGACCAACTGCGGGCCCT
GACCACCGTCACAGCACTTGTGAGGAAGTTCCTGGGGCCAGTGCCAGTGTACCCTGCTGTGG
GTAACCATGAAAGCACACCTGTCAATAGCTTCCCTCCCCCCTTCATTGAGGGCAACCACTCC
TCCCGCTGGCTCTATGAAGCGATGGCCAAGGCTTGGGAGCCCTGGCTGCCTGCCGAAGCCCT
GCGCACCCTCAGAATTGGGGGGTTCTATGCTCTTTCCCCATACCCCGGTCTCCGCCTCATCT
CTCTCAATATGAATTTTTGTTCCCGTGAGAACTTCTGGCTCTTGATCAACTCCACGGATCCC
GCAGGACAGCTCCAGTGGCTGGTGGGGGAGCTTCAGGCTGCTGAGGATCGAGGAGACAAAGT
GCATATAATTGGCCACATTCCCCCAGGGCACTGTCTGAAGAGCTGGAGCTGGAATTATTACC
GAATTGTAGCCAGGTATGAGAACACCCTGGCTGCTCAGTTCTTTGGCCACACTCATGTGGAT
GAATTTGAGGTCTTCTATGATGAAGAGACTCTGAGCCGGCCGCTGGCTGTAGCCTTCCTGGC
ACCCAGTGCAACTACCTACATCGGCCTTAATCCTGGTTACCGTGTGTACCAAATAGATGGAA
ACTACTCCGGGAGCTCTCACGTGGTCCTGGACCATGAGACCTACATCCTGAATCTGACCCAG
GCAAACATACCGGGAGCCATACCGCACTGGCAGCTTCTCTACAGGGCTCGAGAAACCTATGG
GCTGCCCAACACACTGCCTACCGCCTGGCACAACCTGGTATATCGCATGCGGGGCGACATGC
AACTTTTCCAGACCTTCTGGTTTCTCTACCATAAGGGCCACCCACCCTCGGAGCCCTGTGGC
ACGCCCTGCCGTCTGGCTACTCTTTGTGCCCAGCTCTCTGCCCGTGCTGACAGCCCTGCTCT
GTGCCGCCACCTGATGCCAGATGGGAGCCTCCCAGAGGCCCAGAGCCTGTGGCCAAGGCCAC
TGTTTTGCGGATTTCTGGGAGGCGGAGGAGGATCCGGAGGAGGAGGAAGCAATAACCAAAAG
ATTGTGAATATCAAAGAGAAAGTGGCTCAGATTGAGGCTGGAGGCGGAGGAAGCGGCGGCGG
AGGAAGCAATAATCAGAAAATCGTCAACATTAAGGAAAAGGTCGCCCAGATTGAAGCAGGAG
GCGGCGGCAGCGGCGGAGGCGGAAGCAATAATCAGAAGATTGTTAACATCAAAGAAAAGGTG
GCCCAAATTGAAGCAGGAGGAGGAGGATCTGGAGGCGGAGGCAGCAATAACCAGAAGATCGT
CAACATCAAGGAAAAGGTGGCTCAGATCGAGGCAGGAGGCGGAGGAAGCGGAGGGGGCGGCT
CTAACAACCAGAAAATCGTGAACATCAAAGAGAAAGTGGCTCAGATCGAAGCCTAG (SEQ ID NO: 5)

Sequence 6. cDNA sequence of the expression cassette for human ASM control.

ATGGAGACCGACACACTGCTCCTGTGGGTCCTGCTCCTCTGGGTGCCAGGAAGTACAGGAGA
TCACCATCACCATCACCACGACGACGACGACAAGCACCCTCTTTCTCCCCAAGGCCATCCTG
CCAGGTTACATCGCATAGTGCCCCGGCTCCGAGATGTCTTTGGGTGGGGGAACCTCACCTGC
CCAATCTGCAAAGGTCTATTCACCGCCATCAACCTCGGGCTGAAGAAGGAACCCAATGTGGC
TCGCGTGGGCTCCGTGGCCATCAAGCTGTGCAATCTGCTGAAGATAGCACCACCTGCCGTGT
GCCAATCCATTGTCCACCTCTTTGAGGATGACATGGTGGAGGTGTGGAGACGCTCAGTGCTG
AGCCCATCTGAGGCCTGTGGCCTGCTCCTGGGCTCCACCTGTGGGCACTGGGACATTTTCTC
ATCTTGGAACATCTCTTTGCCTACTGTGCCGAAGCCGCCCCCCAAACCCCCTAGCCCCCCAG
CCCCAGGTGCCCCTGTCAGCCGCATCCTCTTCCTCACTGACCTGCACTGGGATCATGACTAC
CTGGAGGGCACGGACCCTGACTGTGCAGACCCACTGTGCTGCCGCCGGGGTTCTGGCCTGCC
GCCCGCATCCCGGCCAGGTGCCGGATACTGGGGCGAATACAGCAAGTGTGACCTGCCCCTGA
GGACCCTGGAGAGCCTGTTGAGTGGGCTGGGCCCAGCCGGCCCTTTTGATATGGTGTACTGG
ACAGGAGACATCCCCGCACATGATGTCTGGCACCAGACTCGTCAGGACCAACTGCGGGCCCT
GACCACCGTCACAGCACTTGTGAGGAAGTTCCTGGGGCCAGTGCCAGTGTACCCTGCTGTGG
GTAACCATGAAAGCACACCTGTCAATAGCTTCCCTCCCCCCTTCATTGAGGGCAACCACTCC
TCCCGCTGGCTCTATGAAGCGATGGCCAAGGCTTGGGAGCCCTGGCTGCCTGCCGAAGCCCT

-continued

GCGCACCCTCAGAATTGGGGGGTTCTATGCTCTTTCCCCATACCCCGGTCTCCGCCTCATCT
CTCTCAATATGAATTTTTGTTCCCGTGAGAACTTCTGGCTCTTGATCAACTCCACGGATCCC
GCAGGACAGCTCCAGTGGCTGGTGGGGGAGCTTCAGGCTGCTGAGGATCGAGGAGACAAAGT
GCATATAATTGGCCACATTCCCCCAGGGCACTGTCTGAAGAGCTGGAGCTGGAATTATTACC
GAATTGTAGCCAGGTATGAGAACACCCTGGCTGCTCAGTTCTTTGGCCACACTCATGTGGAT
GAATTTGAGGTCTTCTATGATGAAGAGACTCTGAGCCGGCCGCTGGCTGTAGCCTTCCTGGC
ACCCAGTGCAACTACCTACATCGGCCTTAATCCTGGTTACCGTGTGTACCAAATAGATGGAA
ACTACTCCGGGAGCTCTCACGTGGTCCTGGACCATGAGACCTACATCCTGAATCTGACCCAG
GCAAACATACCGGGAGCCATACCGCACTGGCAGCTTCTCTACAGGGCTCGAGAAACCTATGG
GCTGCCCAACACACTGCCTACCGCCTGGCACAACCTGGTATATCGCATGCGGGGCGACATGC
ACTTTTCCAGACCTTCTGGTTTCTCTACCATAAGGGCCACCCACCCTCGGAGCCCTGTGGC
ACGCCCTGCCGTCTGGCTACTCTTTGTGCCCAGCTCTCTGCCCGTGCTGACAGCCCTGCTCT
GTGCCGCCACCTGATGCCAGATGGGAGCCTCCCAGAGGCCCAGAGCCTGTGGCCAAGGCCAC
TGTTTTGCTAG (SEQ ID NO: 6)

Sequence 7. cDNA sequence of the expression cassette for human alpha galactosidase (αGal) with one copy of the 2γ3 ICAM-1-targeting peptide at the amino terminus.
ATGGGCTGGTCCTGCATCATTCTGTTTCTGGTGGCTACCGCCACCGGCGTGCACTCTGATCA
CCACCACCATCACCACGACGATGACGACAAGAACAACCAGAAGATCGTCAACATCAAAGAGA
AGGTCGCCCAGATCGAGGCTGGAGGCGGAGGATCTGGTGGTGGCGGATCTGGATTCCTTGGC
CTGGACAACGGCCTGGCTAGAACCCCTACCATGGGATGGCTGCACTGGGAGAGATTCATGTG
CAACCTGGACTGCCAAGAGGAACCCGACTCCTGCATCTCCGAGAAGCTGTTCATGGAAATGG
CCGAGCTGATGGTGTCCGAAGGCTGGAAGGATGCCGGCTACGAGTACCTGTGCATCGACGAC
TGTTGGATGGCCCCTCAGAGAGACTCTGAGGGCAGACTGCAGGCCGATCCTCAGAGATTTCC
CCACGGCATCAGACAGCTGGCCAACTACGTGCACTCCAAGGGCCTGAAGCTGGGCATCTATG
CCGACGTGGGCAACAAGACCTGTGCCGGCTTTCCTGGCTCCTTCGGCTACTACGATATCGAC
GCCCAGACCTTCGCTGACTGGGGAGTCGATCTGCTGAAGTTCGACGGCTGCTACTGCGACTC
CCTGGAAAATCTGGCCGACGGCTACAAGCACATGTCTCTGGCCCTGAACCGGACCGGCAGAT
CCATCGTGTATAGCTGCGAGTGGCCCCTGTACATGTGGCCCTTCCAGAAGCCTAACTACACC
GAGATCAGACAGTACTGCAACCACTGGCGGAACTTCGCCGACATCGACGATAGCTGGAAGTC
CATCAAGTCTATCCTGGACTGGACCTCCTTCAATCAAGAGCGGATCGTGGATGTGGCTGGCC
CTGGCGGATGGAACGATCCTGATATGCTGGTCATCGGCAACTTCGGCCTGTCCTGGAACCAG
CAAGTGACCCAGATGGCCCTGTGGGCCATTATGGCCGCTCCTCTGTTCATGTCCAACGACCT
GAGACACATCAGCCCTCAGGCCAAGGCTCTGCTGCAGGACAAGGATGTGATCGCTATCAACC
AGGATCCTCTGGGCAAGCAGGGCTACCAGTTGAGACAGGGCGACAACTTTGAAGTGTGGGAA
AGACCCCTGTCCGGCCTGGCATGGGCTGTCGCCATGATCAACAGACAAGAGATCGGCGGACC
CCGGTCCTACACAATCGCTGTTGCTTCTCTCGGCAAAGGCGTGGCCTGCAATCCTGCCTGTT
TCATCACACAGCTGCTGCCCGTGAAGAGAAAGCTGGGCTTTTACGAGTGGACCTCTCGGCTG
CGGTCCCACATCAATCCTACCGGAACAGTGCTGCTGCAGCTGGAAAACACCATGCAGATGTC
CCTGAAGGACCTGCTGTGA (SEQID NO: 7)

Sequence 8. cDNA sequence of the expression cassette for human αGal with five tandem-repeats of the 2γ3 ICAM-1-targeting peptide at the carboxyl terminus.
ATGGGCTGGTCCTGCATCATTCTGTTTCTGGTGGCTACCGCCACCGGCGTGCACTCTGATCA
CCACCACCATCACCACGACGATGACGACAAGCTGGACAACGGCCTGGCTAGAACCCCTACCA
TGGGATGGCTGCACTGGGAGAGATTCATGTGCAACCTGGACTGCCAAGAGGAACCCGACTCC
TGCATCTCCGAGAAGCTGTTCATGGAAATGGCCGAGCTGATGGTGTCCGAAGGCTGGAAGGA
TGCCGGCTACGAGTACCTGTGCATCGACGACTGTTGGATGGCCCCTCAGAGAGACTCTGAGG
GCAGACTGCAGGCCGATCCTCAGAGATTTCCCCACGGCATCAGACAGCTGGCCAACTACGTG
CACTCCAAGGGCCTGAAGCTGGGCATCTATGCCGACGTGGGCAACAAGACCTGTGCCGGCTT
TCCTGGCTCCTTCGGCTACTACGATATCGACGCCCAGACCTTCGCTGACTGGGGAGTCGATC
TGCTGAAGTTCGACGGCTGCTACTGCGACTCCCTGGAAAATCTGGCCGACGGCTACAAGCAC
ATGTCTCTGGCCCTGAACCGGACCGGCAGATCCATCGTGTATAGCTGCGAGTGGCCCCTGTA
CATGTGGCCCTTCCAGAAGCCTAACTACACCGAGATCAGACAGTACTGCAACCACTGGCGGA
ACTTCGCCGACATCGACGATAGCTGGAAGTCCATCAAGTCTATCCTGGACTGGACCTCCTTC
AATCAAGAGCGGATCGTGGATGTGGCTGGCCCTGGCGGATGGAACGATCCTGATATGCTGGT
CATCGGCAACTTCGGCCTGTCCTGGAACCAGCAAGTGACCCAGATGGCCCTGTGGGCCATTA
TGGCCGCTCCTCTGTTCATGTCCAACGACCTGAGACACATCAGCCCTCAGGCCAAGGCTCTG
CTGCAGGACAAGGATGTGATCGCTATCAACCAGGATCCTCTGGGCAAGCAGGGCTACCAGTT
GAGACAGGGCGACAACTTTGAAGTGTGGGAAAGACCCCTGTCCGGCCTGGCATGGGCTGTCG
CCATGATCAACAGACAAGAGATCGGCGGACCCCGGTCCTACACAATCGCTGTTGCTTCTCTC
GGCAAAGGCGTGGCCTGCAATCCTGCCTGTTTCATCACACAGCTGCTGCCCGTGAAGAGAAA
GCTGGGCTTTTACGAGTGGACCTCTCGGCTGCGGTCCCACATCAATCCTACCGGAACAGTGC
TGCTGCAGCTGGAAAACACCATGCAGATGTCCCTGAAGGACCTGCTGGGATTCCTTGGCGGA
GGCGGAGGATCTGGTGGTGGCGGATCTAACAACCAGAAGATCGTCAACATCAAAGAGAAGGT
CGCCCAGATCGAGGCTGGCGGCGGTGGATCAGGTGGCGGAGGAAGCAACAATCAGAAAATTG
TGAATATCAAAGAAAAAGTGGCTCAGATTGAAGCAGGCGGCGGAGGTAGCGGAGGTGGTGGC
TCTAACAATCAAAAAATCGTTAACATCAAAGAGAAAGTTGCTCAAATCGAAGCCGGCGGTGG
TGGTTCTGGCGGTGGTGGTAGTAACAATCAAAAGATCGTCAATATCAAAGAAAAGGTGGCAC
AAATCGAGGCAGGCGGAGGCGGCTCTGGCGGCGGAGGATCAAACAATCAGAAGATCGTTAC
ATCAAAGAAAAAGTGGCCCAAATTGAGGCCTGA (SEQ ID NO: 8)

Sequence 9. cDNA sequence of the expression cassette for human αGal control.
ATGGGCTGGTCCTGCATCATTCTGTTTCTGGTGGCTACCGCCACCGGCGTGCACTCTGATCA
CCACCACCATCACCACGACGATGACGACAAGCTGGACAACGGCCTGGCTAGAACCCCTACCA
TGGGATGGCTGCACTGGGAGAGATTCATGTGCAACCTGGACTGCCAAGAGGAACCCGACTCC
TGCATCTCCGAGAAGCTGTTCATGGAAATGGCCGAGCTGATGGTGTCCGAAGGCTGGAAGGA
TGCCGGCTACGAGTACCTGTGCATCGACGACTGTTGGATGGCCCCTCAGAGAGACTCTGAGG
GCAGACTGCAGGCCGATCCTCAGAGATTTCCCCACGGCATCAGACAGCTGGCCAACTACGTG -continued CACTCCAAGGGCCTGAAGCTGGGCATCTATGCCGACGTGGGCAACAAGACCTGTGCCGGCTT
TCCTGGCTCCTTCGGCTACTACGATATCGACGCCCAGACCTTCGCTGACTGGGGAGTCGATC
TGCTGAAGTTCGACGGCTGCTACTGCGACTCCCTGGAAAATCTGGCCGACGGCTACAAGCAC
ATGTCTCTGGCCCTGAACCGGACCGGCAGATCCATCGTGTATAGCTGCGAGTGGCCCCTGTA
CATGTGGCCCTTCCAGAAGCCTAACTACACCGAGATCAGACAGTACTGCAACCACTGGCGGA
ACTTCGCCGACATCGACGATAGCTGGAAGTCCATCAAGTCTATCCTGGACTGGACCTCCTTC
AATCAAGAGCGGATCGTGGATGTGGCTGGCCCTGGCGGATGGAACGATCCTGATATGCTGGT
CATCGGCAACTTCGGCCTGTCCTGGAACCAGCAAGTGACCCAGATGGCCCTGTGGGCCATTA
TGGCCGCTCCTCTGTTCATGTCCAACGACCTGAGACACATCAGCCCTCAGGCCAAGGCTCTG
CTGCAGGACAAGGATGTGATCGCTATCAACCAGGATCCTCTGGGCAAGCAGGGCTACCAGTT
GAGACAGGGCGACAACTTTGAAGTGTGGGAAAGACCCCTGTCCGGCCTGGCATGGGCTGTCG
CCATGATCAACAGACAAGAGATCGGCGGACCCCGGTCCTACACAATCGCTGTTGCTTCTCTC
GGCAAAGGCGTGGCCTGCAATCCTGCCTGTTTCATCACACAGCTGCTGCCCGTGAAGAGAAA
GCTGGGCTTTTACGAGTGGACCTCTCGGCTGCGGTCCCACATCAATCCTACCGGAACAGTGC
TGCTGCAGCTGGAAAACACCATGCAGATGICCCTGAAGGACCTGCTGTGA (SEQ ID NO: 9)

Sequence 10. cDNA sequence of the expression cassette for human glucocerebrosidase (GCase) with one copy of the 2γ3 ICAM-1-targeting peptide at the amino terminus.

ATGGGCTGGTCCTGCATCATTCTGTTTCTGGTGGCTACCGCCACCGGCGTGCACTCTGATCA
CCACCACCATCACCACGACGATGACGACAAGAACAACCAGAAGATCGTCAACATCAAAGAGA
AGGTCGCCCAGATCGAGGCTGGCGGCGGAGGATCTGGCGGAGGCGGATCTGGATTTTTGGGA
GCCAGACCTTGCATCCCCAAGTCCTTCGGCTACTCCTCTGTCGTGTGCGTGTGCAACGCCAC
CTACTGCGACAGCTTCGACCCTCCTACCTTTCCTGCTCTGGGCACATTCTCCAGATACGAGT
CCACCAGATCCGGCAGACGGATGGAACTGAGCATGGGCCCTATCCAGGCTAACCATACCGGC
ACAGGACTGCTGCTGACACTGCAGCCCGAGCAGAAATTCCAGAAAGTGAAAGGCTTCGGCGG
AGCCATGACCGATGCCGCCGCTCTGAATATTCTGGCTCTGAGCCCTCCTGCTCAGAACCTGC
TGCTCAAGTCCTACTTCTCCGAGGAAGGCATCGGCTACAACATCATCCGGGTGCCAATGGCC
TCCTGCGACTTCTCTATCCGGACCTACACCTACGCTGACACCCCTGACGATTTCCAGCTGCA
CAACTTCAGCCTGCCTGAAGAGGACACCAAGCTGAAGATCCCTCTGATCCACAGAGCCCTGC
AGCTGGCTCAGAGGCCTGTTTCTCTGCTGGCCTCTCCTTGGACCTCTCCAACCTGGCTGAAA
ACAAATGGCGCCGTGAACGGCAAGGGCTCCCTGAAAGGACAACCCGGCGATATCTACCACCA
GACCTGGGCCAGATACTTCGTGAAGTTCCTGGACGCCTACGCCGAGCACAAGCTGCAGTTTT
GGGCTGTGACCGCCGAGAACGAGCCTTCTGCTGGACTGCTGTCTGGCTACCCTTTCCAGTGC
CTGGGCTTTACCCCTGAGCACCAGAGAGACTTTATCGCCAGAGATCTGGGCCCCACACTGGC
CAATTCTACCCACCATAATGTGCGGCTGCTGATGCTGGACGACCAGAGACTGCTGTTGCCCC
ACTGGGCTAAAGTGGTGCTGACCGATCCTGAGGCCGCCAAATACGTGCACGGAATCGCCGTG
CACTGGTATCTGGACTTTCTGGCCCCTGCCAAGGCTACCCTGGGCGAGACACATAGACTGTT
CCCCAACACCATGCTGTTCGCCTCTGAGGCCTGTGTGGGCTCCAAGTTCTGGGAGCAGTCTG
TGCGACTCGGCTCTTGGGATAGAGGCATGCAGTACTCCCACTCCATCATCACCAACCTGCTG
TACCACGTCGTCGGCTGGACCGATTGGAACCTGGCACTGAATCCTGAAGGCGGCCCTAACTG
GGTCCGAAACTTCGTGGACTCCCCTATCATCGTGGACATCACCAAGGACACCTTCTACAAGC
AGCCCATGTTCTACCATCTGGGCCACTTCAGCAAGTTCATCCCCGAGGGCTCTCAGAGAGTC
GGCCTGGTTGCCTCTCAGAAGAACGACCTGGACGCTGTGGCTCTGATGCACCCTGATGGATC
TGCTGTGGTGGTCGTGCTGAACCGGTCCTCCAAAGATGTGCCCCTGACCATCAAGGATCCCG
CCGTGGGATTCCTGGAAACCATCTCTCCTGGCTACTCCATCCACACCTACCTGTGGCGTAGA
CAGTGA (SEQ ID NO: 10)

Sequence 11. cDNA sequence of the expression cassette for human GCase with five tandem-repeats of the 2γ3 ICAM-1-targeting peptide at the amino terminus.

ATGGGCTGGTCCTGCATCATTCTGTTTCTGGTGGCTACCGCCACCGGCGTGCACTCTGATCA
CCACCACCATCACCACGACGATGACGACAAGAACAACCAGAAGATCGTCAACATCAAAGAGA
AGGTCGCCCAGATCGAGGCTGGCGGCGGAGGATCTGGCGGAGGCGGATCTAACAATCAGAAA
ATTGTGAATATCAAAGAAAAAGTGGCTCAGATTGAAGCCGGCGGTGGTGGTAGCGGTGGCGG
AGGAAGTAACAATCAAAAGATCGTGAACATCAAAGAAAAAGTTGCACAAATCGAGGCAGGCG
GTGGCGGCAGCGGAGGTGGTGGATCCAACAACCAGAAAATCGTGAACATCAAAGAAAAGGTG
GCCCAAATCGAAGCCGGCGGAGGCGGTTCAGGCGGCGGAGGTTCAAACAATCAGAAGATCGT
TAATATCAAAGAAAAGGTTGCCCAGATTGAGGCAGGCGGAGGTGGAAGCGGCGGAGGCGGCT
CTGGATTTTTGGGAGCCAGACCTTGCATCCCCAAGTCCTTCGGCTACTCCTCTGTCGTGTGC
GTGTGCAACGCCACCTACTGCGACAGCTTCGACCCTCCTACCTTTCCTGCTCTGGGCACATT
CTCCAGATACGAGTCCACCAGATCCGGCAGACGGATGGAACTGAGCATGGGCCCTATCCAGG
CTAACCATACCGGCACAGGACTGCTGCTGACACTGCAGCCCGAGCAGAAATTCCAGAAAGTG
AAAGGCTTCGGCGGAGCCATGACCGATGCCGCCGCTCTGAATATTCTGGCTCTGAGCCCTCC
TGCTCAGAACCTGCTGCTCAAGTCCTACTTCTCCGAGGAAGGCATCGGCTACAACATCATCC
GGGTGCCAATGGCCTCCTGCGACTTCTCTATCCGGACCTACACCTACGCTGACACCCCTGAC
GATTTCCAGCTGCACAACTTCAGCCTGCCTGAAGAGGACACCAAGCTGAAGATCCCTCTGAT
CCACAGAGCCCTGCAGCTGGCTCAGAGGCCTGTTTCTCTGCTGGCCTCTCCTTGGACCTCTC
CAACCTGGCTGAAAACAAATGGCGCCGTGAACGGCAAGGGCTCCCTGAAAGGACAACCCGGC
GATATCTACCACCAGACCTGGGCCAGATACTTCGTGAAGTTCCTGGACGCCTACGCCGAGCA
CAAGCTGCAGTTTTGGGCTGTGACCGCCGAGAACGAGCCTTCTGCTGGACTGCTGTCTGGCT
ACCCTTTCCAGTGCCTGGGCTTTACCCCTGAGCACCAGAGAGACTTTATCGCCAGAGATCTG
GGCCCCACACTGGCCAATTCTACCCACCATAATGTGCGGCTGCTGATGCTGGACGACCAGAG
ACTGCTGTTGCCCCACTGGGCTAAAGTGGTGCTGACCGATCCTGAGGCCGCCAAATACGTGC
ACGGAATCGCCGTGCACTGGTATCTGGACTTTCTGGCCCCTGCCAAGGCTACCCTGGGCGAG
ACACATAGACTGTTCCCCAACACCATGCTGTTCGCCTCTGAGGCCTGTGTGGGCTCCAAGTT
CTGGGAGCAGTCTGTGCGACTCGGCTCTTGGGATAGAGGCATGCAGTACTCCCACTCCATCA
TCACCAACCTGCTGTACCACGTCGTCGGCTGGACCGATTGGAACCTGGCACTGAATCCTGAA
GGCGGCCCTAACTGGGTCCGAAACTTCGTGGACTCCCCTATCATCGTGGACATCACCAAGGA
CACCTTCTACAAGCAGCCCATGTTCTACCATCTGGGCCACTTCAGCAAGTTCATCCCCGAGG
GCTCTCAGAGAGTCGGCCTGGTTGCCTCTCAGAAGAACGACCTGGACGCTGTGGCTCTGATG

-continued

CACCCTGATGGATCTGCTGTGGTGGTCGTGCTGAACCGGTCCTCCAAAGATGTGCCCCTGAC
CATCAAGGATCCCGCCGTGGGATTCCTGGAAACCATCTCTCCTGGCTACTCCATCCACACCT
ACCTGTGGCGTAGACAGTGA (SEQ ID NO: 11)

Sequence 12. cDNA sequence of the expression cassette for human GCase control.
ATGGGCTGGTCCTGCATCATTCTGTTTCTGGTGGCTACCGCCACCGGCGTGCACTCTGATCA
CCACCACCATCACCACGACGATGACGACAAGCTGGACAACGGCCTGGCTAGAACCCCTACCA
TGGGATGGCTGCACTGGGAGAGATTCATGTGCAACCTGGACTGCCAAGAGGAACCCGACTCC
TGCATCTCCGAGAAGCTGTTCATGGAAATGGCCGAGCTGATGGTGTCCGAAGGCTGGAAGGA
TGCCGGCTACGAGTACCTGTGCATCGACGACTGTTGGATGGCCCCTCAGAGAGACTCTGAGG
GCAGACTGCAGGCCGATCCTCAGAGATTTCCCCACGGCATCAGACAGCTGGCCAACTACGTG
CACTCCAAGGGCCTGAAGCTGGGCATCTATGCCGACGTGGGCAACAAGACCTGTGCCGGCTT
TCCTGGCTCCTTCGGCTACTACGATATCGACGCCCAGACCTTCGCTGACTGGGGAGTCGATC
TGCTGAAGTTCGACGGCTGCTACTGCGACTCCCTGGAAAATCTGGCCGACGGCTACAAGCAC
ATGTCTCTGGCCCTGAACCGGACCGGCAGATCCATCGTGTATAGCTGCGAGTGGCCCCTGTA
CATGTGGCCCTTCCAGAAGCCTAACTACACCGAGATCAGACAGTACTGCAACCACTGGCGGA
ACTTCGCCGACATCGACGATAGCTGGAAGTCCATCAAGTCTATCCTGGACTGGACCTCCTTC
AATCAAGAGCGGATCGTGGATGTGGCTGGCCCTGGCGGATGGAACGATCCTGATATGCTGGT
CATCGGCAACTTCGGCCTGTCCTGGAACCAGCAAGTGACCCAGATGGCCCTGTGGGCCATTA
TGGCCGCTCCTCTGTTCATGTCCAACGACCTGAGACACATCAGCCCTCAGGCCAAGGCTCTG
CTGCAGGACAAGGATGTGATCGCTATCAACCAGGATCCTCTGGGCAAGCAGGGCTACCAGTT
GAGACAGGGCGACAACTTTGAAGTGTGGGAAAGACCCCTGTCCGGCCTGGCATGGGCTGTCG
CCATGATCAACAGACAAGAGATCGGCGGACCCCGGTCCTACACAATCGCTGTTGCTTCTCTC
GGCAAAGGCGTGGCCTGCAATCCTGCCTGTTTCATCACACAGCTGCTGCCCGTGAAGAGAAA
GCTGGGCTTTTACGAGTGGACCTCTCGGCTGCGGTCCCACATCATCCTACCGGAACAGTGC
TGCTGCAGCTGGAAAACACCATGCAGATGTCCCTGAAGGACCTGCTGTGA (SEQ ID NO: 12)

Sequence 13. Amino acid sequence of the expression cassette for human acid sphingomyelinase (ASM) with one copy of the 2γ3 ICAM-1-targeting peptide at the amino terminus
METDTLLLWVLLLWVPGSTGDHHHHHHDDDDKNNQKIVNIKEKVAQIEAGGGGSGGGGSGFL
GHPLSPQGHPARLHRIVPRLRDVFGWGNLTCPICKGLFTAINLGLKKEPNVARVGSVAIKLC
NLLKIAPPAVCQSIVHLFEDDMVEVWRRSVLSPSEACGLLLGSTCGHWDIFSSWNISLPTVP
KPPPKPPSPPAPGAPVSRILFLTDLHWDHDYLEGTDPDCADPLCCRRGSGLPPASRPGAGYW
GEYSKCDLPLRTLESLLSGLGPAGPFDMVYWTGDIPAHDVWHQTRQDQLRALTTVTALVRKF
LGPVPVYPAVGNHESTPVNSFPPPFIEGNHSSRWLYEAMAKAWEPWLPAEALRTLRIGGFYA
LSPYPGLRLISLNMNFCSRENFWLLINSTDPAGQLQWLVGELQAAEDRGDKVHIIGHIPPGH
CLKSWSWNYYRIVARYENTLAAQFFGHTHVDEFEVFYDEETLSRPLAVAFLAPSATTYIGLN
PGYRVYQIDGNYSGSSHVVLDHETYILNLTQANIPGAIPHWQLLYRARETYGLPNTLPTAWH
NLVYRMRGDMQLFQTFWFLYHKGHPPSEPCGTPCRLATLCAQLSARADSPALCRHLMPDGSL
PEAQSLWPRPLFC* (SEQ ID NO: 13)

Sequence 14. Amino acid sequence of the expression cassette for human ASM with five tandem-repeats of the 2γ3 ICAM-1-targeting peptide at the amino terminus.
METDTLLLWVLLLWVPGSTGDHHHHHHDDDDKNNQKIVNIKEKVAQIEAGGGGSGGGGSNNQ
KIVNIKEKVAQIEAGGGGSGGGGSNNQKIVNIKEKVAQIEAGGGGSGGGGSNNQKIVNIKEK
VAQIEAGGGGSGGGGSNNQKIVNIKEKVAQIEAGGGGSGGGGSGFLGHPLSPQGHPARLHRI
VPRLRDVFGWGNLTCPICKGLFTAINLGLKKEPNVARVGSVAIKLCNLLKIAPPAVCQSIVH
LFEDDMVEVWRRSVLSPSEACGLLLGSTCGHWDIFSSWNISLPTVPKPPPKPPSPPAPGAPV
SRILFLTDLHWDHDYLEGTDPDCADPLCCRRGSGLPPASRPGAGYWGEYSKCDLPLRTLESL
LSGLGPAGPFDMVYWTGDIPAHDVWHQTRQDQLRALTTVTALVRKFLGPVPVYPAVGNHEST
PVNSFPPPFIEGNHSSRWLYEAMAKAWEPWLPAEALRTLRIGGFYALSPYPGLRLISLNMNF
CSRENFWLLINSTDPAGQLQWLVGELQAAEDRGDKVHIIGHIPPGHCLKSWSWNYYRIVARY
ENTLAAQFFGHTHVDEFEVFYDEETLSRPLAVAFLAPSATTYIGLNPGYRVYQIDGNYSGSS
HVVLDHETYILNLTQANIPGAIPHWQLLYRARETYGLPNTLPTAWHNLVYRMRGDMQLFQTF
WFLYHKGHPPSEPCGTPCRLATLCAQLSARADSPALCRHLMPDGSLPEAQSLWPRPLFC*
(SEQ ID NO: 14)

Sequence 15. Amino acid sequence of the expression cassette for human ASM with ten tandem-repeats of the 2γ3 ICAM-1-targeting peptide at the amino terminus.
METDTLLLWVLLLWVPGSTGDHHHHHHDDDDKNNQKIVNIKEKVAQIEAGGGGSGGGGSNNQ
KIVNIKEKVAQIEAGGGGSGGGGSNNQKIVNIKEKVAQIEAGGGGSGGGGSNNQKIVNIKEK
VAQIEAGGGGSGGGGSNNQKIVNIKEKVAQIEAGGGGSGGGGSNNQKIVNIKEKVAQIEAGG
GGSGGGGSNNQKIVNIKEKVAQIEAGGGGSGGGGSNNQKIVNIKEKVAQIEAGGGGSGGGGS
NNQKIVNIKEKVAQIEAGGGGSGGGGSNNQKIVNIKEKVAQIEAGGGGSGGGGSGFLGHPLS
PQGHPARLHRIVPRLRDVFGWGNLTCPICKGLFTAINLGLKKEPNVARVGSVAIKLCNLLKI
APPAVCQSIVHLFEDDMVEVWRRSVLSPSEACGLLLGSTCGHWDIFSSWNISLPTVPKPPPK
PPSPPAPGAPVSRILFLTDLHWDHDYLEGTDPDCADPLCCRRGSGLPPASRPGAGYWGEYSK
CDLPLRTLESLLSGLGPAGPFDMVYWTGDIPAHDVWHQTRQDQLRALTTVTALVRKFLGPVP
VYPAVGNHESTPVNSFPPPFIEGNHSSRWLYEAMAKAWEPWLPAEALRTLRIGGFYALSPYP
GLRLISLNMNFCSRENFWLLINSTDPAGQLQWLVGELQAAEDRGDKVHIIGHIPPGHCLKSW
SWNYYRIVARYENTLAAQFFGHTHVDEFEVFYDEETLSRPLAVAFLAPSATTYIGLNPGYRV
YQIDGNYSGSSHVVLDHETYILNLTQANIPGAIPHWQLLYRARETYGLPNTLPTAWHNLVYR
MRGDMQLFQTFWFLYHKGHPPSEPCGTPCRLATLCAQLSARADSPALCRHLMPDGSLPEAQS
LWPRPLFC* (SEQ ID NO: 15)

-continued

Sequence 16. Amino acid sequence of the expression cassette for human ASM with five tandem-repeats of the 2γ3 ICAM-1-targeting peptide at the carboxyl terminus.
METDTLLLWVLLLWVPGSTGDHHHHHHDDDDKHPLSPQGHPARLHRIVPRLRDVFGWGNLTC
PICKGLFTAINLGLKKEPNVARVGSVAIKLCNLLKIAPPAVCQSIVHLFEDDMVEVWRRSVL
SPSEACGLLLGSTCGHWDIFSSWNISLPTVPKPPPKPPSPPAPGAPVSRILFLTDLHWDHDY
LEGTDPDCADPLCCRRGSGLPPASRPGAGYWGEYSKCDLPLRTLESLLSGLGPAGPFDMVYW
TGDIPAHDVWHQTRQDQLRALTTVTALVRKFLGPVPVYPAVGNHESTPVNSFPPPFIEGNHS
SRWLYEAMAKAWEPWLPAEALRTLRIGGFYALSPYPGLRLISLNMNFCSRENFWLLINSTDP
AGQLQWLVGELQAAEDRGDKVHIIGHIPPGHCLKSWSWNYYRIVARYENTLAAQFFGHTHVD
EFEVFYDEETLSRPLAVAFLAPSATTYIGLNPGYRVYQIDGNYSGSSHVVLDHETYILNLTQ
ANIPGAIPHWQLLYRARETYGLPNTLPTAWHNLVYRMRGDMQLFQTFWFLYHKGHPPSEPCG
TPCRLATLCAQLSARADSPALCRHLMPDGSLPEAQSLWPRPLFCGFLGGGGGSGGGGSNNQK
IVNIKEKVAQIEAGGGGSGGGGSNNQKIVNIKEKVAQIEAGGGGSGGGGSNNQKIVNIKEKV
AQIEAGGGGSGGGGSNNQKIVNIKEKVAQIEAGGGGSGGGGSNNQKIVNIKEKVAQIEA*
(SEQ ID NO: 16)

Sequence 17. Amino acid sequence of the expression cassette for human ASM control.
METDTLLLWVLLLWVPGSTGDHHHHHHDDDDKHPLSPQGHPARLHRIVPRLRDVFGWGNLTC
PICKGLFTAINLGLKKEPNVARVGSVAIKLCNLLKIAPPAVCQSIVHLFEDDMVEVWRRSVL
SPSEACGLLLGSTCGHWDIFSSWNISLPTVPKPPPKPPSPPAPGAPVSRILFLTDLHWDHDY
LEGTDPDCADPLCCRRGSGLPPASRPGAGYWGEYSKCDLPLRTLESLLSGLGPAGPFDMVYW
TGDIPAHDVWHQTRQDQLRALTTVTALVRKFLGPVPVYPAVGNHESTPVNSFPPPFIEGNHS
SRWLYEAMAKAWEPWLPAEALRTLRIGGFYALSPYPGLRLISLNMNFCSRENFWLLINSTDP
AGQLQWLVGELQAAEDRGDKVHIIGHIPPGHCLKSWSWNYYRIVARYENTLAAQFFGHTHVD
EFEVFYDEETLSRPLAVAFLAPSATTYIGLNPGYRVYQIDGNYSGSSHVVLDHETYILNLTQ
ANIPGAIPHWQLLYRARETYGLPNTLPTAWHNLVYRMRGDMQLFQTFWFLYHKGHPPSEPCG
TPCRLATLCAQLSARADSPALCRHLMPDGSLPEAQSLWPRPLFC* (SEQ ID NO: 17)

Sequence 18. Amino acid sequence of the expression cassette for human alpha galactosidase (αGal) with one copy of the 2γ3 ICAM-1-targeting peptide at the amino terminus.
MGWSCIILFLVATATGVHSDHHHHHHDDDDKNNQKIVNIKEKVAQIEAGGGGSGGGGSGFLG
LDNGLARTPTMGWLHWERFMCNLDCQEEPDSCISEKLFMEMAELMVSEGWKDAGYEYLCIDD
CWMAPQRDSEGRLQADPQRFPHGIRQLANYVHSKGLKLGIYADVGNKTCAGFPGSFGYYDID
AQTFADWGVDLLKFDGCYCDSLENLADGYKHMSLALNRTGRSIVYSCEWPLYMWPFQKPNYT
EIRQYCNHWRNFADIDDSWKSIKSILDWTSFNQERIVDVAGPGGWNDPDMLVIGNFGLSWNQ
QVTQMALWAIMAAPLFMSNDLRHISPQAKALLQDKDVIAINQDPLGKQGYQLRQGDNFEVWE
RPLSGLAWAVAMINRQEIGGPRSYTIAVASLGKGVACNPACFITQLLPVKRKLGFYEWTSRL
RSHINPTGTVLLQLENTMQMSLKDLL* (SEQ ID NO: 18)

Sequence 19. Amino acid sequence of the expression cassette for human αGal with five tandem-repeats of the 2γ3 ICAM-1-targeting peptide at the carboxyl terminus.
MGWSCIILFLVATATGVHSDHHHHHHDDDDKLDNGLARTPTMGWLHWERFMCNLDCQEEPDS
CISEKLFMEMAELMVSEGWKDAGYEYLCIDDCWMAPQRDSEGRLQADPQRFPHGIRQLANYV
HSKGLKLGIYADVGNKTCAGFPGSFGYYDIDAQTFADWGVDLLKFDGCYCDSLENLADGYKH
MSLALNRTGRSIVYSCEWPLYMWPFQKPNYTEIRQYCNHWRNFADIDDSWKSIKSILDWTSF
NQERIVDVAGPGGWNDPDMLVIGNFGLSWNQQVTQMALWAIMAAPLFMSNDLRHISPQAKAL
LQDKDVIAINQDPLGKQGYQLRQGDNFEVWERPLSGLAWAVAMINRQEIGGPRSYTIAVASL
GKGVACNPACFITQLLPVKRKLGFYEWTSRLRSHINPTGTVLLQLENTMQMSLKDLLGFLGG
GGGSGGGGSNNQKIVNIKEKVAQIEAGGGGSGGGGSNNQKIVNIKEKVAQIEAGGGGSGGGG
SNNQKIVNIKEKVAQIEAGGGGSGGGGSNNQKIVNIKEKVAQIEAGGGGSGGGGSNNQKIVN
IKEKVAQIEA* (SEQ ID NO: 19)

Sequence 20. Amino acid sequence of the expression cassette for human αGal control.
MGWSCIILFLVATATGVHSDHHHHHHDDDDKLDNGLARTPTMGWLHWERFMCNLDCQEEPDS
CISEKLFMEMAELMVSEGWKDAGYEYLCIDDCWMAPQRDSEGRLQADPQRFPHGIRQLANYV
HSKGLKLGIYADVGNKTCAGFPGSFGYYDIDAQTFADWGVDLLKFDGCYCDSLENLADGYKH
MSLALNRTGRSIVYSCEWPLYMWPFQKPNYTEIRQYCNHWRNFADIDDSWKSIKSILDWTSF
NQERIVDVAGPGGWNDPDMLVIGNFGLSWNQQVTQMALWAIMAAPLFMSNDLRHISPQAKAL
LQDKDVIAINQDPLGKQGYQLRQGDNFEVWERPLSGLAWAVAMINRQEIGGPRSYTIAVASL
GKGVACNPACFITQLLPVKRKLGFYEWTSRLRSHINPTGTVLLQLENTMQMSLKDLL* (SEQ
ID NO: 20)

Sequence 21. Amino acid sequence of the expression cassette for human glucocerebrosidase (GCase) with one copy of the 2γ3 ICAM-1-targeting peptide at the amino terminus.
MGWSCIILFLVATATGVHSDHHHHHHDDDDKNNQKIVNIKEKVAQIEAGGGGSGGGGSGFLG
ARPCIPKSFGYSSVVCVCNATYCDSFDPPTFPALGTFSRYESTRSGRRMELSMGPIQANHTG
TGLLLTLQPEQKFQKVKGFGGAMTDAAALNILALSPPAQNLLLKSYFSEEGIGYNIIRVPMA
SCDFSIRTYTYADTPDDFQLHNFSLPEEDTKLKIPLIHRALQLAQRPVSLLASPWTSPTWLK
TNGAVNGKGSLKGQPGDIYHQTWARYFVKFLDAYAEHKLQFWAVTAENEPSAGLLSGYPFQC
LGFTPEHQRDFIARDLGPTLANSTHHNVRLLMLDDQRLLLPHWAKVVLTDPEAAKYVHGIAV
HWYLDFLAPAKATLGETHRLFPNTMLFASEACVGSKFWEQSVRLGSWDRGMQYSHSIITNLL
YHVVGWTDWNLALNPEGGPNWVRNFVDSPIIVDITKDTFYKQPMFYHLGHFSKFIPEGSQRV
GLVASQKNDLDAVALMHPDGSAVVVVLNRSSKDVPLTIKDPAVGFLETISPGYSIHTYLWRR
Q* (SEQ ID NO: 21)

-continued

Sequence 22. Amino acid sequence of the expression cassette for human GCase with five tandem-repeats of the 2γ3 ICAM-1-targeting peptide at the amino terminus.
MGWSCIILFLVATATGVHSDHHHHHHDDDDKNNQKIVNIKEKVAQIEAGGGGSGGGGSNNQK
IVNIKEKVAQIEAGGGGSGGGGSNNQKIVNIKEKVAQIEAGGGGSGGGGSNNQKIVNIKEKV
AQIEAGGGGSGGGGSNNQKIVNIKEKVAQIEAGGGGSGGGGSGFLGARPCIPKSFGYSSVVC
VCNATYCDSFDPPTFPALGTFSRYESTRSGRRMELSMGPIQANHTGTGLLLTLQPEQKFQKV
KGFGGAMTDAAALNILALSPPAQNLLLKSYFSEEGIGYNIIRVPMASCDFSIRTYTYADTPD
DFQLHNFSLPEEDTKLKIPLIHRALQLAQRPVSLLASPWTSPTWLKTNGAVNGKGSLKGQPG
DIYHQTWARYFVKFLDAYAEHKLQFWAVTAENEPSAGLLSGYPFQCLGFTPEHQRDFIARDL
GPTLANSTHHNVRLLMLDDQRLLLPHWAKVVLTDPEAAKYVHGIAVHWYLDFLAPAKATLGE
THRLFPNTMLFASEACVGSKFWEQSVRLGSWDRGMQYSHSIITNLLYHVVGWTDWNLALNPE
GGPNWVRNFVDSPIIVDITKDTFYKQPMFYHLGHFSKFIPEGSQRVGLVASQKNDLDAVALM
HPDGSAVVVVLNRSSKDVPLTIKDPAVGFLETISPGYSIHTYLWRRQ* (SEQ ID NO: 22)

Sequence 23. Amino acid sequence of the expression cassette for human GCase control.
MGWSCIILFLVATATGVHSDHHHHHHDDDDKARPCIPKSFGYSSVVCVCNATYCDSFDPPTF
PALGTFSRYESTRSGRRMELSMGPIQANHTGTGLLLTLQPEQKFQKVKGFGGAMTDAAALNI
LALSPPAQNLLLKSYFSEEGIGYNIIRVPMASCDFSIRTYTYADTPDDFQLHNFSLPEEDTK
LKIPLIHRALQLAQRPVSLLASPWTSPTWLKTNGAVNGKGSLKGQPGDIYHQTWARYFVKFL
DAYAEHKLQFWAVTAENEPSAGLLSGYPFQCLGFTPEHQRDFIARDLGPTLANSTHHNVRLL
MLDDQRLLLPHWAKVVLTDPEAAKYVHGIAVHWYLDFLAPAKATLGETHRLFPNTMLFASEA
CVGSKFWEQSVRLGSWDRGMQYSHSIITNLLYHVVGWTDWNLALNPEGGPNWVRNFVDSPII
VDITKDTFYKQPMFYHLGHFSKFIPEGSQRVGLVASQKNDLDAVALMHPDGSAVVVVLNRSS
KDVPLTIKDPAVGFLETISPGYSIHTYLWRRQ* (SEQ ID NO: 23)

Sequence 24. Amino acid sequence of a glycine-serine linker.
GGGGS (SEQ ID NO: 24)

Sequence 25. Amino acid sequence of a two repeats of the glycine-serine linker.
GGGGSGGGGS (SEQ ID NO: 25)

Sequence 26. Amino acid sequence of alternative ICAM-1 targeting peptide.
NNQKIVNLKEKVAQLEA (SEQ ID NO: 26)

Sequence 27. Amino acid sequence of alternative ICAM-1 targeting peptide.
NNQKLVNIKEKVAQIEA (SEQ ID NO: 27)

Sequence 28. Amino acid sequence of alternative ICAM-1 targeting peptide.
YPASYQR (SEQ ID NO: 28)

Sequence 29. Amino acid sequence of alternative ICAM-1 targeting peptide.
YQATPLP (SEQ ID NO: 29)

Sequence 30. Amino acid sequence of alternative ICAM-1 targeting peptide.
GSLLSAA (SEQ ID NO: 30)

Sequence 31. Amino acid sequence of alternative ICAM-1 targeting peptide.
FSPHSRT (SEQ ID NO: 31)

Sequence 32. Amino acid sequence of alternative ICAM-1 targeting peptide.
YPFLPTA (SEQ ID NO: 32)

Sequence 33. Amino acid sequence of alternative ICAM-1 targeting peptide.
GCKLCAQ (SEQ ID NO: 33)

Sequence 34. Amino acid sequence of the first protease cleavage site, recognized by cathepsin L or cathepsin B, in the fusion proteins.
GFLG (SEQ ID NO: 34)

Sequence 35. Amino acid sequence of the second protease cleavage site, the enterokinase cleavage sequence, in the fusion proteins.
DDDDK (SEQ ID NO: 35)

Sequence 36. Amino acid sequence of the second protease cleavage site, the Tobacco etch virus cleavage sequence, in the fusion proteins.
ENLYFQ (SEQ ID NO: 36)

Sequence 37. Amino acid sequence of the second protease cleavage site, the Factor Xa cleavage site, in the fusion proteins.
IEGR (SEQ ID NO: 37)

Sequence 38. Amino acid sequence of the second protease cleavage site, the matrix metalloproteinase 9 (MMP-9) cleavage site, in the fusion proteins.
PXXXX, where X in position 2 and 3 is any residue, position 3 is a hydrophobic residue, and the X in position 5 is S or T (SEQ ID NO: 38).

-continued

Sequence 39. Amino acid sequence of the second protease cleavage site, the papain cleavage site, in the fusion proteins.
XXXXZRUXXX, where Z is a hydrophobic residue, and U is any residue but V (SEQ ID NO: 39)

Sequence 40. Amino acid sequence of the second protease cleavage site, the thrombin cleavage site, in the fusion proteins.
LVPRGS (SEQ ID NO: 40)

Sequence 41. Amino acid sequence of a secretion signal in the fusion proteins.
METDTLLLWVLLLWVPGSTG (SEQ ID NO: 41)

Sequence 42. Amino acid sequence of a secretion signal in the fusion proteins.
MGWSCIILFLVATATGVHSD (SEQ ID NO: 42)

REFERENCE

He, X., et al. (1999). "Characterization of human acid sphingomyelinase purified from the media of overexpressing Chinese hamster ovary cells." Biochimica et Biophysica Acta (BBA)—Protein Structure and Molecular Enzymology 1432(2): 251-264.

The foregoing Examples and Sequences illustrate various embodiments, but do are not intended to limit the disclosure, and those skilled in the art will recognize that various modifications to the Examples and Sequences can be made without departing from the scope of the invention.

SEQUENCE LISTING

<160> NUMBER OF SEQ ID NOS: 42

<210> SEQ ID NO 1
<211> LENGTH: 17
<212> TYPE: PRT
<213> ORGANISM: Homo sapiens

<400> SEQUENCE: 1

```
Asn Asn Gln Lys Ile Val Asn Ile Lys Glu Lys Val Ala Gln Ile Glu
1               5                   10                  15

Ala
```

<210> SEQ ID NO 2
<211> LENGTH: 1902
<212> TYPE: DNA
<213> ORGANISM: artificial sequence
<220> FEATURE:
<223> OTHER INFORMATION: cDNA sequence of the expression cassette for human acid sphingomyelinase (ASM) with one copy of the 2gamma3 ICAM-1-targeting peptide at the amino terminus

<400> SEQUENCE: 2

```
atggagaccg acacactgct cctgtgggtc ctgctcctct gggtgccagg aagtacagga      60

gatcaccatc accatcacca cgacgacgac gacaagaata accaaaagat tgtgaatatc     120

aaagagaaag tggctcagat tgaggctgga ggcggaggaa gcggcggcgg aggaagcgga     180

tttctgggac accctctttc tccccaaggc catcctgcca ggttacatcg catagtgccc     240

cggctccgag atgtctttgg gtgggggaac ctcacctgcc caatctgcaa aggtctattc     300

accgccatca acctcgggct gaagaaggaa cccaatgtgg ctcgcgtggg ctccgtggcc     360

atcaagctgt gcaatctgct gaagatagca ccacctgccg tgtgccaatc cattgtccac     420

ctctttgagg atgacatggt ggaggtgtgg agacgctcag tgctgagccc atctgaggcc     480

tgtggcctgc tcctgggctc cacctgtggg cactgggaca ttttctcatc ttggaacatc     540

tctttgccta ctgtgccgaa gccgcccccc aaacccccta gccccccagc cccaggtgcc     600

cctgtcagcc gcatcctctt cctcactgac ctgcactggg atcatgacta cctggagggc     660
```

-continued

```
acggaccctg actgtgcaga cccactgtgc tgccgccggg gttctggcct gccgcccgca    720
tcccggccag gtgccggata ctggggcgaa tacagcaagt gtgacctgcc cctgaggacc    780
ctggagagcc tgttgagtgg gctgggccca gccggccctt ttgatatggt gtactggaca    840
ggagacatcc ccgcacatga tgtctggcac cagactcgtc aggaccaact gcgggccctg    900
accaccgtca cagcacttgt gaggaagttc ctggggccag tgccagtgta ccctgctgtg    960
ggtaaccatg aaagcacacc tgtcaatagc ttccctcccc ccttcattga gggcaaccac   1020
tcctcccgct ggctctatga agcgatggcc aaggcttggg agccctggct gcctgccgaa   1080
gccctgcgca ccctcagaat tggggggttc tatgctcttt ccccataccc cggtctccgc   1140
ctcatctctc tcaatatgaa tttttgttcc cgtgagaact tctggctctt gatcaactcc   1200
acggatcccg caggacagct ccagtggctg gtgggggagc ttcaggctgc tgaggatcga   1260
ggagacaaag tgcatataat tggccacatt cccccagggc actgtctgaa gagctggagc   1320
tggaattatt accgaattgt agccaggtat gagaacaccc tggctgctca gttctttggc   1380
cacactcatg tggatgaatt tgaggtcttc tatgatgaag agactctgag ccggccgctg   1440
gctgtagcct tcctggcacc cagtgcaact acctacatcg gccttaatcc tggttaccgt   1500
gtgtaccaaa tagatggaaa ctactccggg agctctcacg tggtcctgga ccatgagacc   1560
tacatcctga atctgaccca ggcaaacata ccgggagcca taccgcactg gcagcttctc   1620
tacagggctc gagaaaccta tggctgccc aacacactgc ctaccgcctg gcacaacctg   1680
gtatatcgca tgcggggcga catgcaactt ttccagacct tctggtttct ctaccataag   1740
ggccacccac cctcggagcc ctgtggcacg ccctgccgtc tggctactct ttgtgcccag   1800
ctctctgccc gtgctgacag ccctgctctg tgccgccacc tgatgccaga tgggagcctc   1860
ccagaggccc agagcctgtg gccaaggcca ctgttttgct ag                      1902
```

<210> SEQ ID NO 3
<211> LENGTH: 2226
<212> TYPE: DNA
<213> ORGANISM: artificial sequence
<220> FEATURE:
<223> OTHER INFORMATION: cDNA sequence of the expression cassette for human ASM with five tandem-repeats of the 2?3 ICAM-1-targeting peptide at the amino terminus.

<400> SEQUENCE: 3

```
atggagaccg acacactgct cctgtgggtc ctgctcctct gggtgccagg aagtacagga     60
gatcaccatc accatcacca cgacgacgac gacaagaata accaaaagat tgtgaatatc    120
aaagagaaag tggctcagat tgaggctgga ggcggaggaa gcggcggcgg aggaagcaat    180
aatcagaaaa tcgtcaacat taaggaaaag gtcgcccaga ttgaagcagg aggcggcggc    240
agcggcggag gcggaagcaa taatcagaag attgttaaca tcaaagaaaa ggtggcccaa    300
attgaagcag gaggaggagg atctggaggc ggaggcagca ataaccagaa gatcgtcaac    360
atcaaggaaa aggtggctca gatcgaggca ggaggcggag gaagcggagg gggcggctct    420
aacaaccaga aaatcgtgaa catcaaagag aaagtggctc agatcgaagc cggcggagga    480
ggatccggag gaggaggaag cggatttctg ggacaccctc tttctcccca aggccatcct    540
gccaggttac atcgcatagt gccccggctc cgagatgtct ttgggtgggg gaacctcacc    600
tgcccaatct gcaaaggtct attcaccgcc atcaacctcg ggctgaagaa ggaacccaat    660
gtggctcgcg tgggctccgt ggccatcaag ctgtgcaatc tgctgaagat agcaccacct    720
gccgtgtgcc aatccattgt ccacctcttt gaggatgaca tggtggaggt gtggagacgc    780
```

```
tcagtgctga gcccatctga ggcctgtggc ctgctcctgg gctccacctg tgggcactgg    840

gacattttct catcttggaa catctctttg cctactgtgc cgaagccgcc ccccaaaccc    900

cctagccccc cagccccagg tgcccctgtc agccgcatcc tcttcctcac tgacctgcac    960

tgggatcatg actacctgga gggcacggac cctgactgtg cagacccact gtgctgccgc   1020

cggggttctg gcctgccgcc cgcatcccgg ccaggtgccg gatactgggg cgaatacagc   1080

aagtgtgacc tgcccctgag gaccctggag agcctgttga gtgggctggg cccagccggc   1140

ccttttgata tggtgtactg gacaggagac atccccgcac atgatgtctg gcaccagact   1200

cgtcaggacc aactgcgggc cctgaccacc gtcacagcac ttgtgaggaa gttcctgggg   1260

ccagtgccag tgtaccctgc tgtgggtaac catgaaagca cacctgtcaa tagcttccct   1320

ccccccttca ttgagggcaa ccactcctcc cgctggctct atgaagcgat ggccaaggct   1380

tgggagccct ggctgcctgc cgaagccctg cgcaccctca gaattggggg gttctatgct   1440

ctttccccat accccggtct ccgcctcatc tctctcaata tgaatttttg ttcccgtgag   1500

aacttctggc tcttgatcaa ctccacggat cccgcaggac agctccagtg gctggtgggg   1560

gagcttcagg ctgctgagga tcgaggagac aaagtgcata taattggcca cattccccca   1620

gggcactgtc tgaagagctg gagctggaat tattaccgaa ttgtagccag gtatgagaac   1680

accctggctg ctcagttctt tggccacact catgtggatg aatttgaggt cttctatgat   1740

gaagagactc tgagccggcc gctggctgta gccttcctgg cacccagtgc aactacctac   1800

atcggcctta atcctggtta ccgtgtgtac caaatagatg gaaactactc cgggagctct   1860

cacgtggtcc tggaccatga gacctacatc ctgaatctga cccaggcaaa cataccggga   1920

gccataccgc actggcagct tctctacagg gctcgagaaa cctatgggct gcccaacaca   1980

ctgcctaccg cctggcacaa cctggtatat cgcatgcggg gcgacatgca acttttccag   2040

accttctggt ttctctacca taagggccac ccaccctcgg agccctgtgg cacgccctgc   2100

cgtctggcta ctctttgtgc ccagctctct gcccgtgctg acagccctgc tctgtgccgc   2160

cacctgatgc cagatgggag cctcccagag gcccagagcc tgtggccaag gccactgttt   2220

tgctag                                                              2226
```

```
<210> SEQ ID NO 4
<211> LENGTH: 2631
<212> TYPE: DNA
<213> ORGANISM: artificial sequence
<220> FEATURE:
<223> OTHER INFORMATION: cDNA sequence of the expression cassette for
      human ASM with ten tandem-repeats of the 2gamma3 ICAM-1-targeting
      peptide at the amino terminus

<400> SEQUENCE: 4
```

```
atggagaccg acacactgct cctgtgggtc ctgctcctct gggtgccagg aagtacagga     60

gatcaccatc accatcacca cgacgacgac gacaagaata accaaaagat tgtgaatatc    120

aaagagaaag tggctcagat tgaggctgga ggcggaggaa gcggcggcgg aggaagcaat    180

aatcagaaaa tcgtcaacat taaggaaaag gtcgcccaga ttgaagcagg aggcggcggc    240

agcggcggag gcggaagcaa taatcagaag attgttaaca tcaaagaaaa ggtggcccaa    300

attgaagcag gaggaggagg atctggaggc ggaggcagca ataaccagaa gatcgtcaac    360

atcaaggaaa aggtggctca gatcgaggca ggaggcggag gaagcggagg gggcggctct    420

aacaaccaga aaatcgtgaa catcaaagag aaagtggctc agatcgaagc cggcggagga    480
```

-continued

```
ggatccggag gaggaggaag caataaccaa aagattgtga atatcaaaga gaaagtggct    540
cagattgagg ctggaggcgg aggaagcggc ggcggaggaa gcaataatca gaaaatcgtc    600
aacattaagg aaaaggtcgc ccagattgaa gcaggaggcg gcggcagcgg cggaggcgga    660
agcaataatc agaagattgt taacatcaaa gaaaaggtgg cccaaattga agcaggagga    720
ggaggatctg gaggcggagg cagcaataac cagaagatcg tcaacatcaa ggaaaaggtg    780
gctcagatcg aggcaggagg cggaggaagc ggagggggcg gctctaacaa ccagaaaatc    840
gtgaacatca aagagaaagt ggctcagatc gaagccggcg gaggaggatc cggaggagga    900
ggaagcggat ttctgggaca ccctctttct ccccaaggcc atcctgccag gttacatcgc    960
atagtgcccc ggctccgaga tgtctttggg tgggggaacc tcacctgccc aatctgcaaa   1020
ggtctattca ccgccatcaa cctcgggctg aagaaggaac ccaatgtggc tcgcgtgggc   1080
tccgtggcca tcaagctgtg caatctgctg aagatagcac cacctgccgt gtgccaatcc   1140
attgtccacc tctttgagga tgacatggtg gaggtgtgga gacgctcagt gctgagccca   1200
tctgaggcct gtggcctgct cctgggctcc acctgtgggc actgggacat tttctcatct   1260
tggaacatct ctttgcctac tgtgccgaag ccgcccccca aacccccctag cccccccagcc  1320
ccaggtgccc ctgtcagccg catcctcttc ctcactgacc tgcactggga tcatgactac   1380
ctggagggca cggaccctga ctgtgcagac ccactgtgct gccgccgggg ttctggcctg   1440
ccgcccgcat cccggccagg tgccggatac tggggcgaat acagcaagtg tgacctgccc   1500
ctgaggaccc tggagagcct gttgagtggg ctgggcccag ccggcccttt tgatatggtg   1560
tactggacag gagacatccc cgcacatgat gtctggcacc agactcgtca ggaccaactg   1620
cgggccctga ccaccgtcac agcacttgtg aggaagttcc tggggccagt gccagtgtac   1680
cctgctgtgg gtaaccatga aagcacacct gtcaatagct tccctccccc cttcattgag   1740
ggcaaccact cctcccgctg gctctatgaa gcgatggcca aggcttggga gccctggctg   1800
cctgccgaag ccctgcgcac cctcagaatt ggggggttct atgctctttc cccataccccc  1860
ggtctccgcc tcatctctct caatatgaat tttgttcccc gtgagaactt ctggctcttg   1920
atcaactcca cggatcccgc aggacagctc cagtggctgg tgggggagct tcaggctgct   1980
gaggatcgag gagacaaagt gcatataatt ggccacattc ccccagggca ctgtctgaag   2040
agctggagct ggaattatta ccgaattgta gccaggtatg agaacaccct ggctgctcag   2100
ttctttggcc acactcatgt ggatgaattt gaggtcttct atgatgaaga gactctgagc   2160
cggccgctgg ctgtagcctt cctggcaccc agtgcaacta cctacatcgg ccttaatcct   2220
ggttaccgtg tgtaccaaat agatggaaac tactccggga gctctcacgt ggtcctggac   2280
catgagacct acatcctgaa tctgacccag gcaaacatac cgggagccat accgcactgg   2340
cagcttctct acagggctcg agaaacctat gggctgccca acacactgcc taccgcctgg   2400
cacaacctgg tatatcgcat gcggggcgac atgcaacttt tccagacctt ctggtttctc   2460
taccataagg gccacccacc ctcggagccc tgtggcacgc cctgccgtct ggctactctt   2520
tgtgcccagc tctctgcccg tgctgacagc cctgctctgt gccgccacct gatgccagat   2580
gggagcctcc cagaggccca gagcctgtgg ccaaggccac tgttttgcta g            2631
```

<210> SEQ ID NO 5
<211> LENGTH: 2226
<212> TYPE: DNA
<213> ORGANISM: artificial sequence
<220> FEATURE:
<223> OTHER INFORMATION: cDNA sequence of the expression cassette for -continued human ASM with five tandem-repeats of the 2gamma3 ICAM-1-targeting peptide at the carboxyl terminus

<400> SEQUENCE: 5

```
atggagaccg acacactgct cctgtgggtc ctgctcctct gggtgccagg aagtacagga     60
gatcaccatc accatcacca cgacgacgac gacaagcacc ctctttctcc ccaaggccat    120
cctgccaggt tacatcgcat agtgccccgg ctccgagatg tctttgggtg ggggaacctc    180
acctgcccaa tctgcaaagg tctattcacc gccatcaacc tcgggctgaa gaaggaaccc    240
aatgtggctc gcgtgggctc cgtggccatc aagctgtgca atctgctgaa gatagcacca    300
cctgccgtgt gccaatccat tgtccacctc tttgaggatg acatggtgga ggtgtggaga    360
cgctcagtgc tgagcccatc tgaggcctgt ggcctgctcc tgggctccac ctgtgggcac    420
tgggacattt tctcatcttg gaacatctct ttgcctactg tgccgaagcc gccccccaaa    480
cccccctagcc ccccagcccc aggtgcccct gtcagccgca tcctcttcct cactgacctg    540
cactgggatc atgactacct ggagggcacg gaccctgact gtgcagaccc actgtgctgc    600
cgccggggtt ctggcctgcc gcccgcatcc cggccaggtg ccggatactg gggcgaatac    660
agcaagtgtg acctgcccct gaggaccctg gagagcctgt tgagtgggct gggcccagcc    720
ggcccttttg atatggtgta ctggacagga gacatccccg cacatgatgt ctggcaccag    780
actcgtcagg accaactgcg ggccctgacc accgtcacag cacttgtgag gaagttcctg    840
gggccagtgc cagtgtaccc tgctgtgggt aaccatgaaa gcacacctgt caatagcttc    900
cctcccccct tcattgaggg caaccactcc tcccgctggc tctatgaagc gatggccaag    960
gcttgggagc cctggctgcc tgccgaagcc ctgcgcaccc tcagaattgg ggggttctat   1020
gctctttccc catacccgg tctccgcctc atctctctca atatgaattt ttgttcccgt   1080
gagaacttct ggctcttgat caactccacg gatcccgcag gacagctcca gtggctggtg   1140
ggggagcttc aggctgctga ggatcgagga gacaaagtgc atataattgg ccacattccc   1200
ccagggcact gtctgaagag ctggagctgg aattattacc gaattgtagc caggtatgag   1260
aacaccctgg ctgctcagtt ctttggccac actcatgtgg atgaatttga ggtcttctat   1320
gatgaagaga ctctgagccg gccgctggct gtagccttcc tggcacccag tgcaactacc   1380
tacatcggcc ttaatcctgg ttaccgtgtg taccaaatag atggaaacta ctccgggagc   1440
tctcacgtgg tcctggacca tgagacctac atcctgaatc tgacccaggc aaacataccg   1500
ggagccatac cgcactggca gcttctctac agggctcgag aaacctatgg gctgcccaac   1560
acactgccta ccgcctggca caacctggta tatcgcatgc ggggcgacat gcaacttttc   1620
cagaccttct ggtttctcta ccataagggc cacccaccct cggagccctg tggcacgccc   1680
tgccgtctgg ctactctttg tgcccagctc tctgcccgtg ctgacagccc tgctctgtgc   1740
cgccacctga tgccagatgg gagcctccca gaggcccaga gcctgtggcc aaggccactg   1800
ttttgcggat ttctgggagg cggaggagga tccggaggag gaggaagcaa taaccaaaag   1860
attgtgaata tcaaagagaa agtggctcag attgaggctg gaggcggagg aagcggcggc   1920
ggaggaagca ataatcagaa aatcgtcaac attaaggaaa aggtcgccca gattgaagca   1980
ggaggcggcg gcagcggcgg aggcggaagc aataatcaga agattgttaa catcaaagaa   2040
aaggtggccc aaattgaagc aggaggagga ggatctggag gcggaggcag caataaccag   2100
aagatcgtca acatcaagga aaaggtggct cagatcgagg caggaggcgg aggaagcgga   2160
gggggcggct ctaacaacca gaaaatcgtg aacatcaaag agaaagtggc tcagatcgaa   2220
```

-continued

```
gcctag                                                              2226

<210> SEQ ID NO 6
<211> LENGTH: 1809
<212> TYPE: DNA
<213> ORGANISM: artificial sequence
<220> FEATURE:
<223> OTHER INFORMATION: cDNA sequence of the expression cassette for
      human ASM control

<400> SEQUENCE: 6

atggagaccg acacactgct cctgtgggtc ctgctcctct gggtgccagg aagtacagga     60

gatcaccatc accatcacca cgacgacgac gacaagcacc ctctttctcc ccaaggccat    120

cctgccaggt tacatcgcat agtgccccgg ctccgagatg tctttgggtg ggggaacctc    180

acctgcccaa tctgcaaagg tctattcacc gccatcaacc tcgggctgaa gaaggaaccc    240

aatgtggctc gcgtgggctc cgtggccatc aagctgtgca atctgctgaa gatagcacca    300

cctgccgtgt gccaatccat tgtccacctc tttgaggatg acatggtgga ggtgtggaga    360

cgctcagtgc tgagcccatc tgaggcctgt ggcctgctcc tgggctccac ctgtgggcac    420

tgggacattt tctcatcttg gaacatctct ttgcctactg tgccgaagcc gcccccccaaa    480

ccccctagcc ccccagcccc aggtgcccct gtcagccgca tcctcttcct cactgacctg    540

cactgggatc atgactacct ggagggcacg gaccctgact gtgcagaccc actgtgctgc    600

cgccggggtt ctggcctgcc gcccgcatcc cggccaggtg ccggatactg ggcgaatac    660

agcaagtgtg acctgcccct gaggaccctg gagagcctgt tgagtgggct gggcccagcc    720

ggccctttttg atatggtgta ctggacagga gacatccccg cacatgatgt ctggcaccag    780

actcgtcagg accaactgcg ggccctgacc accgtcacag cacttgtgag gaagttcctg    840

gggccagtgc cagtgtaccc tgctgtgggt aaccatgaaa gcacacctgt caatagcttc    900

cctccccccct tcattgaggg caaccactcc tcccgctggc tctatgaagc gatggccaag    960

gcttgggagc cctggctgcc tgccgaagcc ctgcgcaccc tcagaattgg ggggttctat   1020

gctctttccc cataccccgg tctccgcctc atctctctca atatgaattt ttgttcccgt   1080

gagaacttct ggctcttgat caactccacg gatcccgcag gacagctcca gtggctggtg   1140

ggggagcttc aggctgctga ggatcgagga gacaaagtgc atataattgg ccacattccc   1200

ccagggcact gtctgaagag ctggagctgg aattattacc gaattgtagc caggtatgag   1260

aacaccctgg ctgctcagtt ctttggccac actcatgtgg atgaatttga ggtcttctat   1320

gatgaagaga ctctgagccg gccgctggct gtagccttcc tggcacccag tgcaactacc   1380

tacatcggcc ttaatcctgg ttaccgtgtg taccaaatag atggaaacta ctccgggagc   1440

tctcacgtgg tcctggacca tgagacctac atcctgaatc tgacccaggc aaacataccg   1500

ggagccatac cgcactggca gcttctctac agggctcgag aaacctatgg gctgcccaac   1560

acactgccta ccgcctggca caacctggta tatcgcatgc ggggcgacat gcaacttttc   1620

cagaccttct ggtttctcta ccataagggc cacccaccct cggagccctg tggcacgccc   1680

tgccgtctgg ctactctttg tgcccagctc tctgcccgtg ctgacagccc tgctctgtgc   1740

cgccacctga tgccagatgg gagcctccca gaggcccaga gcctgtggcc aaggccactg   1800

ttttgctag                                                           1809

<210> SEQ ID NO 7
<211> LENGTH: 1383
<212> TYPE: DNA
```

<213> ORGANISM: artificial sequence
<220> FEATURE:
<223> OTHER INFORMATION: cDNA sequence of the expression cassette for
      human alpha galactosidase (?Gal) with one copy of the 2gamma3
      ICAM-1-targeting peptide at the amino terminus

<400> SEQUENCE: 7

```
atgggctggt cctgcatcat tctgtttctg gtggctaccg ccaccggcgt gcactctgat     60

caccaccacc atcaccacga cgatgacgac aagaacaacc agaagatcgt caacatcaaa    120

gagaaggtcg cccagatcga ggctggaggc ggaggatctg gtggtggcgg atctggattc    180

cttggcctgg acaacggcct ggctagaacc cctaccatgg gatggctgca ctgggagaga    240

ttcatgtgca acctggactg ccaagaggaa cccgactcct gcatctccga gaagctgttc    300

atggaaatgg ccgagctgat ggtgtccgaa ggctggaagg atgccggcta cgagtacctg    360

tgcatcgacg actgttggat ggcccctcag agagactctg agggcagact gcaggccgat    420

cctcagagat ttccccacgg catcagacag ctggccaact acgtgcactc caagggcctg    480

aagctgggca tctatgccga cgtgggcaac aagacctgtg ccggctttcc tggctccttc    540

ggctactacg atatcgacgc ccagaccttc gctgactggg gagtcgatct gctgaagttc    600

gacggctgct actgcgactc cctggaaaat ctggccgacg gctacaagca catgtctctg    660

gccctgaacc ggaccggcag atccatcgtg tatagctgcg agtggcccct gtacatgtgg    720

cccttccaga agcctaacta caccgagatc agacagtact gcaaccactg gcggaacttc    780

gccgacatcg acgatagctg gaagtccatc aagtctatcc tggactggac ctccttcaat    840

caagagcgga tcgtggatgt ggctggccct ggcggatgga acgatcctga tatgctggtc    900

atcggcaact tcggcctgtc ctggaaccag caagtgaccc agatggccct gtgggccatt    960

atggccgctc ctctgttcat gtccaacgac ctgagacaca tcagccctca ggccaaggct   1020

ctgctgcagg acaaggatgt gatcgctatc aaccaggatc ctctgggcaa gcagggctac   1080

cagttgagac agggcgacaa ctttgaagtg tgggaaagac ccctgtccgg cctggcatgg   1140

gctgtcgcca tgatcaacag acaagagatc ggcggacccc ggtcctacac aatcgctgtt   1200

gcttctctcg gcaaaggcgt ggcctgcaat cctgcctgtt tcatcacaca gctgctgccc   1260

gtgaagagaa agctgggctt ttacgagtgg acctctcggc tgcggtccca catcaatcct   1320

accggaacag tgctgctgca gctggaaaac accatgcaga tgtccctgaa ggacctgctg   1380

tga                                                                 1383
```

<210> SEQ ID NO 8
<211> LENGTH: 1707
<212> TYPE: DNA
<213> ORGANISM: artificial sequence
<220> FEATURE:
<223> OTHER INFORMATION: cDNA sequence of the expression cassette for
      human ?Gal with five tandem-repeats of the 2?3 ICAM-1-targeting
      peptide at the carboxyl terminus

<400> SEQUENCE: 8

```
atgggctggt cctgcatcat tctgtttctg gtggctaccg ccaccggcgt gcactctgat     60

caccaccacc atcaccacga cgatgacgac aagctggaca acggcctggc tagaacccct    120

accatgggat ggctgcactg ggagagattc atgtgcaacc tggactgcca agaggaaccc    180

gactcctgca tctccgagaa gctgttcatg gaaatggccg agctgatggt gtccgaaggc    240

tggaaggatg ccggctacga gtacctgtgc atcgacgact gttggatggc ccctcagaga    300

gactctgagg gcagactgca ggccgatcct cagagatttc cccacggcat cagacagctg    360
```

-continued

```
gccaactacg tgcactccaa gggcctgaag ctgggcatct atgccgacgt gggcaacaag    420

acctgtgccg gctttcctgg ctccttcggc tactacgata tcgacgccca gaccttcgct    480

gactggggag tcgatctgct gaagttcgac ggctgctact gcgactccct ggaaaatctg    540

gccgacggct acaagcacat gtctctggcc ctgaaccgga ccggcagatc catcgtgtat    600

agctgcgagt ggcccctgta catgtggccc ttccagaagc ctaactacac cgagatcaga    660

cagtactgca accactggcg gaacttcgcc gacatcgacg atagctggaa gtccatcaag    720

tctatcctgg actggacctc cttcaatcaa gagcggatcg tggatgtggc tggccctggc    780

ggatggaacg atcctgatat gctggtcatc ggcaacttcg gcctgtcctg gaaccagcaa    840

gtgacccaga tggccctgtg ggccattatg gccgctcctc tgttcatgtc caacgacctg    900

agacacatca gccctcaggc caaggctctg ctgcaggaca aggatgtgat cgctatcaac    960

caggatcctc tgggcaagca gggctaccag ttgagacagg gcgacaactt tgaagtgtgg   1020

gaaagacccc tgtccggcct ggcatgggct gtcgccatga tcaacagaca agagatcggc   1080

ggaccccggt cctacacaat cgctgttgct tctctcggca aaggcgtggc ctgcaatcct   1140

gcctgtttca tcacacagct gctgcccgtg aagagaaagc tgggctttta cgagtggacc   1200

tctcggctgc ggtcccacat caatcctacc ggaacagtgc tgctgcagct ggaaaacacc   1260

atgcagatgt ccctgaagga cctgctggga ttccttggcg gaggcggagg atctggtggt   1320

ggcggatcta acaaccagaa gatcgtcaac atcaaagaga aggtcgccca gatcgaggct   1380

ggcggcggtg gatcaggtgg cggaggaagc aacaatcaga aaattgtgaa tatcaaagaa   1440

aaagtggctc agattgaagc aggcggcgga ggtagcggag gtggtggctc taacaatcaa   1500

aaaatcgtta acatcaaaga gaaagttgct caaatcgaag ccggcggtgg tggttctggc   1560

ggtggtggta gtaacaatca aaagatcgtc aatatcaaag aaaaggtggc acaaatcgag   1620

gcaggcggag gcggctctgg cggcggagga tcaaacaatc agaagatcgt taacatcaaa   1680

gaaaaagtgg cccaaattga ggcctga                                       1707
```

<210> SEQ ID NO 9
<211> LENGTH: 1290
<212> TYPE: DNA
<213> ORGANISM: artificial sequence
<220> FEATURE:
<223> OTHER INFORMATION: cDNA sequence of the expression cassette for human ?Gal control

<400> SEQUENCE: 9

```
atgggctggt cctgcatcat tctgtttctg gtggctaccg ccaccggcgt gcactctgat     60

caccaccacc atcaccacga cgatgacgac aagctggaca acggcctggc tagaacccct    120

accatgggat ggctgcactg ggagagattc atgtgcaacc tggactgcca agaggaaccc    180

gactcctgca tctccgagaa gctgttcatg gaaatggccg agctgatggt gtccgaaggc    240

tggaaggatg ccggctacga gtacctgtgc atcgacgact gttggatggc ccctcagaga    300

gactctgagg gcagactgca ggccgatcct cagagatttc cccacggcat cagacagctg    360

gccaactacg tgcactccaa gggcctgaag ctgggcatct atgccgacgt gggcaacaag    420

acctgtgccg gctttcctgg ctccttcggc tactacgata tcgacgccca gaccttcgct    480

gactggggag tcgatctgct gaagttcgac ggctgctact gcgactccct ggaaaatctg    540

gccgacggct acaagcacat gtctctggcc ctgaaccgga ccggcagatc catcgtgtat    600

agctgcgagt ggcccctgta catgtggccc ttccagaagc ctaactacac cgagatcaga    660
```

```
cagtactgca accactggcg gaacttcgcc gacatcgacg atagctggaa gtccatcaag     720

tctatcctgg actggacctc cttcaatcaa gagcggatcg tggatgtggc tggccctggc     780

ggatggaacg atcctgatat gctggtcatc ggcaacttcg gcctgtcctg gaaccagcaa     840

gtgacccaga tggccctgtg ggccattatg gccgctcctc tgttcatgtc caacgacctg     900

agacacatca gccctcaggc caaggctctg ctgcaggaca aggatgtgat cgctatcaac     960

caggatcctc tgggcaagca gggctaccag ttgagacagg gcgacaactt tgaagtgtgg    1020

gaaagacccc tgtccggcct ggcatgggct gtcgccatga tcaacagaca agagatcggc    1080

ggaccccggt cctacacaat cgctgttgct tctctcggca aaggcgtggc ctgcaatcct    1140

gcctgtttca tcacacagct gctgcccgtg aagagaaagc tgggctttta cgagtggacc    1200

tctcggctgc ggtcccacat caatcctacc ggaacagtgc tgctgcagct ggaaaacacc    1260

atgcagatgt ccctgaagga cctgctgtga                                     1290
```

<210> SEQ ID NO 10
<211> LENGTH: 1680
<212> TYPE: DNA
<213> ORGANISM: artificial sequence
<220> FEATURE:
<223> OTHER INFORMATION: cDNA sequence of the expression cassette for human glucocerebrosidase (GCase) with one copy of the 2gamma ICAM-1-targeting peptide at the amino terminus

<400> SEQUENCE: 10

```
atgggctggt cctgcatcat tctgtttctg gtggctaccg ccaccggcgt gcactctgat      60

caccaccacc atcaccacga cgatgacgac aagaacaacc agaagatcgt caacatcaaa     120

gagaaggtcg cccagatcga ggctggcggc ggaggatctg gcggaggcgg atctggattt     180

ttgggagcca gaccttgcat ccccaagtcc ttcggctact cctctgtcgt gtgcgtgtgc     240

aacgccacct actgcgacag cttcgaccct cctacctttc ctgctctggg cacattctcc     300

agatacgagt ccaccagatc cggcagacgg atggaactga gcatgggccc tatccaggct     360

aaccataccg gcacaggact gctgctgaca ctgcagcccg agcagaaatt ccagaaagtg     420

aaaggcttcg gcggagccat gaccgatgcc gccgctctga atattctggc tctgagccct     480

cctgctcaga acctgctgct caagtcctac ttctccgagg aaggcatcgg ctacaacatc     540

atccgggtgc caatggcctc ctgcgacttc tctatccgga cctacaccta cgctgacacc     600

cctgacgatt tccagctgca caacttcagc ctgcctgaag aggacaccaa gctgaagatc     660

cctctgatcc acagagccct gcagctggct cagaggcctg tttctctgct ggcctctcct     720

tggacctctc caacctggct gaaaacaaat ggcgccgtga acggcaaggg ctccctgaaa     780

ggacaacccg gcgatatcta ccaccagacc tgggccagat acttcgtgaa gttcctggac     840

gcctacgccg agcacaagct gcagttttgg gctgtgaccg ccgagaacga gccttctgct     900

ggactgctgt ctggctaccc tttccagtgc ctgggcttta cccctgagca ccagagagac     960

tttatcgcca gagatctggg ccccacactg gccaattcta cccaccataa tgtgcggctg    1020

ctgatgctgg acgaccagag actgctgttg ccccactggg ctaaagtggt gctgaccgat    1080

cctgaggccg ccaaatacgt gcacggaatc gccgtgcact ggtatctgga ctttctggcc    1140

cctgccaagg ctaccctggg cgagacacat agactgttcc ccaacaccat gctgttcgcc    1200

tctgaggcct gtgtgggctc caagttctgg gagcagtctg tgcgactcgg ctcttgggat    1260

agaggcatgc agtactccca ctccatcatc accaacctgc tgtaccacgt cgtcggctgg    1320
```

-continued accgattgga acctggcact gaatcctgaa ggcggcccta actgggtccg aaacttcgtg 1380
gactccccta tcatcgtgga catcaccaag gacaccttct acaagcagcc catgttctac 1440
catctgggcc acttcagcaa gttcatcccc gagggctctc agagagtcgg cctggttgcc 1500
tctcagaaga acgacctgga cgctgtggct ctgatgcacc ctgatggatc tgctgtggtg 1560
gtcgtgctga accggtcctc caaagatgtg cccctgacca tcaaggatcc cgccgtggga 1620
ttcctggaaa ccatctctcc tggctactcc atccacacct acctgtggcg tagacagtga 1680

<210> SEQ ID NO 11
<211> LENGTH: 2004
<212> TYPE: DNA
<213> ORGANISM: artificial sequence
<220> FEATURE:
<223> OTHER INFORMATION: cDNA sequence of the expression cassette for human GCase with five tandem-repeats of the 2?gamma ICAM-1-targeting peptide at the amino terminus

<400> SEQUENCE: 11
atgggctggt cctgcatcat tctgtttctg gtggctaccg ccaccggcgt gcactctgat 60
caccaccacc atcaccacga cgatgacgac aagaacaacc agaagatcgt caacatcaaa 120
gagaaggtcg cccagatcga ggctggcggc ggaggatctg gcggaggcgg atctaacaat 180
cagaaaattg tgaatatcaa agaaaaagtg gctcagattg aagccggcgg tggtggtagc 240
ggtggcggag gaagtaacaa tcaaaagatc gtgaacatca aagaaaaagt tgcacaaatc 300
gaggcaggcg gtggcggcag cggaggtggt ggatccaaca accagaaaat cgtgaacatc 360
aaagaaaagg tggcccaaat cgaagccggc ggaggcggtt caggcggcgg aggttcaaac 420
aatcagaaga tcgttaatat caaagaaaag gttgcccaga ttgaggcagg cggaggtgga 480
agcggcggag gcggctctgg atttttggga gccagacctt gcatccccaa gtccttcggc 540
tactcctctg tcgtgtgcgt gtgcaacgcc acctactgcg acagcttcga ccctcctacc 600
tttcctgctc tgggcacatt ctccagatac gagtccacca gatccggcag acggatggaa 660
ctgagcatgg gccctatcca ggctaaccat accggcacag gactgctgct gacactgcag 720
cccgagcaga aattccagaa agtgaaaggc ttcggcggag ccatgaccga tgccgccgct 780
ctgaatattc tggctctgag ccctcctgct cagaacctgc tgctcaagtc ctacttctcc 840
gaggaaggca tcggctacaa catcatccgg gtgccaatgg cctcctgcga cttctctatc 900
cggacctaca cctacgctga cacccctgac gatttccagc tgcacaactt cagcctgcct 960
gaagaggaca ccaagctgaa gatccctctg atccacagag ccctgcagct ggctcagagg 1020
cctgtttctc tgctggcctc tccttggacc tctccaacct ggctgaaaac aaatggcgcc 1080
gtgaacggca agggctccct gaaaggacaa cccggcgata tctaccacca gacctgggcc 1140
agatacttcg tgaagttcct ggacgcctac gccgagcaca agctgcagtt ttgggctgtg 1200
accgccgaga acgagccttc tgctggactg ctgtctggct acccctttcca gtgcctgggc 1260 tttacccctg agcaccagag agactttatc gccagagatc tgggccccac actggccaat 1320
tctacccacc ataatgtgcg gctgctgatg ctggacgacc agagactgct gttgccccac 1380
tgggctaaag tggtgctgac cgatcctgag gccgccaaat acgtgcacgg aatcgccgtg 1440
cactggtatc tggactttct ggcccctgcc aaggctaccc tgggcgagac acatagactg 1500
ttccccaaca ccatgctgtt cgcctctgag gcctgtgtgg gctccaagtt ctgggagcag 1560
tctgtgcgac tcggctcttg ggatagaggc atgcagtact cccactccat catcaccaac 1620
ctgctgtacc acgtcgtcgg ctggaccgat tggaacctgg cactgaatcc tgaaggcggc 1680

-continued cctaactggg tccgaaactt cgtggactcc cctatcatcg tggacatcac caaggacacc 1740
ttctacaagc agcccatgtt ctaccatctg ggccacttca gcaagttcat ccccgagggc 1800
tctcagagag tcggcctggt tgcctctcag aagaacgacc tggacgctgt ggctctgatg 1860
caccctgatg gatctgctgt ggtggtcgtg ctgaaccggt cctccaaaga tgtgcccctg 1920
accatcaagg atcccgccgt gggattcctg gaaaccatct ctcctggcta ctccatccac 1980
acctacctgt ggcgtagaca gtga 2004

<210> SEQ ID NO 12
<211> LENGTH: 1290
<212> TYPE: DNA
<213> ORGANISM: artificial sequence
<220> FEATURE:
<223> OTHER INFORMATION: cDNA sequence of the expression cassette for human GCase control

<400> SEQUENCE: 12
atgggctggt cctgcatcat tctgtttctg gtggctaccg ccaccggcgt gcactctgat 60
caccaccacc atcaccacga cgatgacgac aagctggaca acggcctggc tagaacccct 120
accatgggat ggctgcactg ggagagattc atgtgcaacc tggactgcca agaggaaccc 180
gactcctgca tctccgagaa gctgttcatg gaaatggccg agctgatggt gtccgaaggc 240
tggaaggatg ccggctacga gtacctgtgc atcgacgact gttggatggc ccctcagaga 300
gactctgagg gcagactgca ggccgatcct cagagatttc cccacggcat cagacagctg 360
gccaactacg tgcactccaa gggcctgaag ctgggcatct atgccgacgt gggcaacaag 420
acctgtgccg gctttcctgg ctccttcggc tactacgata tcgacgccca gaccttcgct 480
gactggggag tcgatctgct gaagttcgac ggctgctact gcgactccct ggaaaatctg 540
gccgacggct acaagcacat gtctctggcc ctgaaccgga ccggcagatc catcgtgtat 600
agctgcgagt ggcccctgta catgtggccc ttccagaagc ctaactacac cgagatcaga 660
cagtactgca accactggcg gaacttcgcc gacatcgacg atagctggaa gtccatcaag 720
tctatcctgg actggacctc cttcaatcaa gagcggatcg tggatgtggc tggccctggc 780
ggatggaacg atcctgatat gctggtcatc ggcaacttcg gcctgtcctg gaaccagcaa 840
gtgacccaga tggccctgtg ggccattatg gccgctcctc tgttcatgtc caacgacctg 900
agacacatca gccctcaggc caaggctctg ctgcaggaca aggatgtgat cgctatcaac 960
caggatcctc tgggcaagca gggctaccag ttgagacagg gcgacaactt tgaagtgtgg 1020
gaaagacccc tgtccggcct ggcatgggct gtcgccatga tcaacagaca agagatcggc 1080
ggaccccggt cctacacaat cgctgttgct tctctcggca aaggcgtggc ctgcaatcct 1140
gcctgtttca tcacacagct gctgcccgtg aagagaaagc tgggctttta cgagtggacc 1200
tctcggctgc ggtcccacat caatcctacc ggaacagtgc tgctgcagct ggaaaacacc 1260
atgcagatgt ccctgaagga cctgctgtga 1290

<210> SEQ ID NO 13
<211> LENGTH: 633
<212> TYPE: PRT
<213> ORGANISM: artificial sequence
<220> FEATURE:
<223> OTHER INFORMATION: Amino acid sequence of the expression cassette for human acid sphingomyelinase (ASM) with one copy of the 2gamma3 ICAM-1-targeting peptide at the amino terminus

<400> SEQUENCE: 13

-continued

```
Met Glu Thr Asp Thr Leu Leu Leu Trp Val Leu Leu Leu Trp Val Pro
1               5                   10                  15

Gly Ser Thr Gly Asp His His His His His His Asp Asp Asp Asp Lys
            20                  25                  30

Asn Asn Gln Lys Ile Val Asn Ile Lys Glu Lys Val Ala Gln Ile Glu
        35                  40                  45

Ala Gly Gly Gly Gly Ser Gly Gly Gly Gly Ser Gly Phe Leu Gly His
    50                  55                  60

Pro Leu Ser Pro Gln Gly His Pro Ala Arg Leu His Arg Ile Val Pro
65                  70                  75                  80

Arg Leu Arg Asp Val Phe Gly Trp Gly Asn Leu Thr Cys Pro Ile Cys
                85                  90                  95

Lys Gly Leu Phe Thr Ala Ile Asn Leu Gly Leu Lys Lys Glu Pro Asn
            100                 105                 110

Val Ala Arg Val Gly Ser Val Ala Ile Lys Leu Cys Asn Leu Leu Lys
        115                 120                 125

Ile Ala Pro Pro Ala Val Cys Gln Ser Ile Val His Leu Phe Glu Asp
    130                 135                 140

Asp Met Val Glu Val Trp Arg Arg Ser Val Leu Ser Pro Ser Glu Ala
145                 150                 155                 160

Cys Gly Leu Leu Leu Gly Ser Thr Cys Gly His Trp Asp Ile Phe Ser
                165                 170                 175

Ser Trp Asn Ile Ser Leu Pro Thr Val Pro Lys Pro Pro Pro Lys Pro
            180                 185                 190

Pro Ser Pro Pro Ala Pro Gly Ala Pro Val Ser Arg Ile Leu Phe Leu
        195                 200                 205

Thr Asp Leu His Trp Asp His Asp Tyr Leu Glu Gly Thr Asp Pro Asp
    210                 215                 220

Cys Ala Asp Pro Leu Cys Cys Arg Arg Gly Ser Gly Leu Pro Pro Ala
225                 230                 235                 240

Ser Arg Pro Gly Ala Gly Tyr Trp Gly Glu Tyr Ser Lys Cys Asp Leu
                245                 250                 255

Pro Leu Arg Thr Leu Glu Ser Leu Leu Ser Gly Leu Gly Pro Ala Gly
            260                 265                 270

Pro Phe Asp Met Val Tyr Trp Thr Gly Asp Ile Pro Ala His Asp Val
        275                 280                 285

Trp His Gln Thr Arg Gln Asp Gln Leu Arg Ala Leu Thr Thr Val Thr
    290                 295                 300

Ala Leu Val Arg Lys Phe Leu Gly Pro Val Pro Val Tyr Pro Ala Val
305                 310                 315                 320

Gly Asn His Glu Ser Thr Pro Val Asn Ser Phe Pro Pro Pro Phe Ile
                325                 330                 335

Glu Gly Asn His Ser Ser Arg Trp Leu Tyr Glu Ala Met Ala Lys Ala
            340                 345                 350

Trp Glu Pro Trp Leu Pro Ala Glu Ala Leu Arg Thr Leu Arg Ile Gly
        355                 360                 365

Gly Phe Tyr Ala Leu Ser Pro Tyr Pro Gly Leu Arg Leu Ile Ser Leu
    370                 375                 380

Asn Met Asn Phe Cys Ser Arg Glu Asn Phe Trp Leu Leu Ile Asn Ser
385                 390                 395                 400

Thr Asp Pro Ala Gly Gln Leu Gln Trp Leu Val Gly Glu Leu Gln Ala
                405                 410                 415
```

-continued

Ala Glu Asp Arg Gly Asp Lys Val His Ile Ile Gly His Ile Pro Pro
420 425 430

Gly His Cys Leu Lys Ser Trp Ser Trp Asn Tyr Tyr Arg Ile Val Ala
435 440 445

Arg Tyr Glu Asn Thr Leu Ala Ala Gln Phe Phe Gly His Thr His Val
450 455 460

Asp Glu Phe Glu Val Phe Tyr Asp Glu Glu Thr Leu Ser Arg Pro Leu
465 470 475 480

Ala Val Ala Phe Leu Ala Pro Ser Ala Thr Thr Tyr Ile Gly Leu Asn
485 490 495

Pro Gly Tyr Arg Val Tyr Gln Ile Asp Gly Asn Tyr Ser Gly Ser Ser
500 505 510

His Val Val Leu Asp His Glu Thr Tyr Ile Leu Asn Leu Thr Gln Ala
515 520 525

Asn Ile Pro Gly Ala Ile Pro His Trp Gln Leu Leu Tyr Arg Ala Arg
530 535 540

Glu Thr Tyr Gly Leu Pro Asn Thr Leu Pro Thr Ala Trp His Asn Leu
545 550 555 560

Val Tyr Arg Met Arg Gly Asp Met Gln Leu Phe Gln Thr Phe Trp Phe
565 570 575

Leu Tyr His Lys Gly His Pro Pro Ser Glu Pro Cys Gly Thr Pro Cys
580 585 590

Arg Leu Ala Thr Leu Cys Ala Gln Leu Ser Ala Arg Ala Asp Ser Pro
595 600 605

Ala Leu Cys Arg His Leu Met Pro Asp Gly Ser Leu Pro Glu Ala Gln
610 615 620

Ser Leu Trp Pro Arg Pro Leu Phe Cys
625 630

<210> SEQ ID NO 14
<211> LENGTH: 741
<212> TYPE: PRT
<213> ORGANISM: artificial seqence
<220> FEATURE:
<223> OTHER INFORMATION: Amino acid sequence of the expression cassette
for human ASM with five tandem-repeats of the 2?gamma
ICAM-1-targeting peptide at the amino terminus

<400> SEQUENCE: 14

Met Glu Thr Asp Thr Leu Leu Leu Trp Val Leu Leu Leu Trp Val Pro
1 5 10 15

Gly Ser Thr Gly Asp His His His His His His Asp Asp Asp Asp Lys
20 25 30

Asn Asn Gln Lys Ile Val Asn Ile Lys Glu Lys Val Ala Gln Ile Glu
35 40 45

Ala Gly Gly Gly Gly Ser Gly Gly Gly Gly Ser Asn Asn Gln Lys Ile
50 55 60

Val Asn Ile Lys Glu Lys Val Ala Gln Ile Glu Ala Gly Gly Gly Gly
65 70 75 80

Ser Gly Gly Gly Gly Ser Asn Asn Gln Lys Ile Val Asn Ile Lys Glu
85 90 95

Lys Val Ala Gln Ile Glu Ala Gly Gly Gly Gly Ser Gly Gly Gly Gly
100 105 110

Ser Asn Asn Gln Lys Ile Val Asn Ile Lys Glu Lys Val Ala Gln Ile
115 120 125

Glu Ala Gly Gly Gly Gly Ser Gly Gly Gly Gly Ser Asn Asn Gln Lys

-continued

```
    130                 135                 140

Ile Val Asn Ile Lys Glu Lys Val Ala Gln Ile Glu Ala Gly Gly Gly
145                 150                 155                 160

Gly Ser Gly Gly Gly Gly Ser Gly Phe Leu Gly His Pro Leu Ser Pro
                165                 170                 175

Gln Gly His Pro Ala Arg Leu His Arg Ile Val Pro Arg Leu Arg Asp
            180                 185                 190

Val Phe Gly Trp Gly Asn Leu Thr Cys Pro Ile Cys Lys Gly Leu Phe
        195                 200                 205

Thr Ala Ile Asn Leu Gly Leu Lys Lys Glu Pro Asn Val Ala Arg Val
    210                 215                 220

Gly Ser Val Ala Ile Lys Leu Cys Asn Leu Leu Lys Ile Ala Pro Pro
225                 230                 235                 240

Ala Val Cys Gln Ser Ile Val His Leu Phe Glu Asp Asp Met Val Glu
                245                 250                 255

Val Trp Arg Arg Ser Val Leu Ser Pro Ser Glu Ala Cys Gly Leu Leu
            260                 265                 270

Leu Gly Ser Thr Cys Gly His Trp Asp Ile Phe Ser Ser Trp Asn Ile
        275                 280                 285

Ser Leu Pro Thr Val Pro Lys Pro Pro Pro Lys Pro Pro Ser Pro Pro
    290                 295                 300

Ala Pro Gly Ala Pro Val Ser Arg Ile Leu Phe Leu Thr Asp Leu His
305                 310                 315                 320

Trp Asp His Asp Tyr Leu Glu Gly Thr Asp Pro Asp Cys Ala Asp Pro
                325                 330                 335

Leu Cys Cys Arg Arg Gly Ser Gly Leu Pro Pro Ala Ser Arg Pro Gly
            340                 345                 350

Ala Gly Tyr Trp Gly Glu Tyr Ser Lys Cys Asp Leu Pro Leu Arg Thr
        355                 360                 365

Leu Glu Ser Leu Leu Ser Gly Leu Gly Pro Ala Gly Pro Phe Asp Met
    370                 375                 380

Val Tyr Trp Thr Gly Asp Ile Pro Ala His Asp Val Trp His Gln Thr
385                 390                 395                 400

Arg Gln Asp Gln Leu Arg Ala Leu Thr Thr Val Thr Ala Leu Val Arg
                405                 410                 415

Lys Phe Leu Gly Pro Val Pro Val Tyr Pro Ala Val Gly Asn His Glu
            420                 425                 430

Ser Thr Pro Val Asn Ser Phe Pro Pro Pro Phe Ile Glu Gly Asn His
        435                 440                 445

Ser Ser Arg Trp Leu Tyr Glu Ala Met Ala Lys Ala Trp Glu Pro Trp
    450                 455                 460

Leu Pro Ala Glu Ala Leu Arg Thr Leu Arg Ile Gly Gly Phe Tyr Ala
465                 470                 475                 480

Leu Ser Pro Tyr Pro Gly Leu Arg Leu Ile Ser Leu Asn Met Asn Phe
                485                 490                 495

Cys Ser Arg Glu Asn Phe Trp Leu Leu Ile Asn Ser Thr Asp Pro Ala
            500                 505                 510

Gly Gln Leu Gln Trp Leu Val Gly Glu Leu Gln Ala Ala Glu Asp Arg
        515                 520                 525

Gly Asp Lys Val His Ile Ile Gly His Ile Pro Pro Gly His Cys Leu
    530                 535                 540

Lys Ser Trp Ser Trp Asn Tyr Tyr Arg Ile Val Ala Arg Tyr Glu Asn
545                 550                 555                 560
```

```
Thr Leu Ala Ala Gln Phe Phe Gly His Thr His Val Asp Glu Phe Glu
                565                 570                 575

Val Phe Tyr Asp Glu Glu Thr Leu Ser Arg Pro Leu Ala Val Ala Phe
            580                 585                 590

Leu Ala Pro Ser Ala Thr Thr Tyr Ile Gly Leu Asn Pro Gly Tyr Arg
        595                 600                 605

Val Tyr Gln Ile Asp Gly Asn Tyr Ser Gly Ser Ser His Val Val Leu
    610                 615                 620

Asp His Glu Thr Tyr Ile Leu Asn Leu Thr Gln Ala Asn Ile Pro Gly
625                 630                 635                 640

Ala Ile Pro His Trp Gln Leu Leu Tyr Arg Ala Arg Glu Thr Tyr Gly
                645                 650                 655

Leu Pro Asn Thr Leu Pro Thr Ala Trp His Asn Leu Val Tyr Arg Met
            660                 665                 670

Arg Gly Asp Met Gln Leu Phe Gln Thr Phe Trp Phe Leu Tyr His Lys
        675                 680                 685

Gly His Pro Pro Ser Glu Pro Cys Gly Thr Pro Cys Arg Leu Ala Thr
    690                 695                 700

Leu Cys Ala Gln Leu Ser Ala Arg Ala Asp Ser Pro Ala Leu Cys Arg
705                 710                 715                 720

His Leu Met Pro Asp Gly Ser Leu Pro Glu Ala Gln Ser Leu Trp Pro
                725                 730                 735

Arg Pro Leu Phe Cys
            740


<210> SEQ ID NO 15
<211> LENGTH: 876
<212> TYPE: PRT
<213> ORGANISM: artificial sequence
<220> FEATURE:
<223> OTHER INFORMATION: Amino acid sequence of the expression cassette
      for human ASM with ten tandem-repeats of the 2gamma3
      ICAM-1-targeting peptide at the amino terminus

<400> SEQUENCE: 15

Met Glu Thr Asp Thr Leu Leu Leu Trp Val Leu Leu Leu Trp Val Pro
1               5                   10                  15

Gly Ser Thr Gly Asp His His His His His His Asp Asp Asp Asp Lys
            20                  25                  30

Asn Asn Gln Lys Ile Val Asn Ile Lys Glu Lys Val Ala Gln Ile Glu
        35                  40                  45

Ala Gly Gly Gly Gly Ser Gly Gly Gly Gly Ser Asn Asn Gln Lys Ile
    50                  55                  60

Val Asn Ile Lys Glu Lys Val Ala Gln Ile Glu Ala Gly Gly Gly Gly
65                  70                  75                  80

Ser Gly Gly Gly Gly Ser Asn Asn Gln Lys Ile Val Asn Ile Lys Glu
                85                  90                  95

Lys Val Ala Gln Ile Glu Ala Gly Gly Gly Gly Ser Gly Gly Gly Gly
            100                 105                 110

Ser Asn Asn Gln Lys Ile Val Asn Ile Lys Glu Lys Val Ala Gln Ile
        115                 120                 125

Glu Ala Gly Gly Gly Gly Ser Gly Gly Gly Gly Ser Asn Asn Gln Lys
    130                 135                 140

Ile Val Asn Ile Lys Glu Lys Val Ala Gln Ile Glu Ala Gly Gly Gly
145                 150                 155                 160
```

-continued

```
Gly Ser Gly Gly Gly Gly Ser Asn Asn Gln Lys Ile Val Asn Ile Lys
                165                 170                 175

Glu Lys Val Ala Gln Ile Glu Ala Gly Gly Gly Gly Ser Gly Gly Gly
            180                 185                 190

Gly Ser Asn Asn Gln Lys Ile Val Asn Ile Lys Glu Lys Val Ala Gln
        195                 200                 205

Ile Glu Ala Gly Gly Gly Gly Ser Gly Gly Gly Gly Ser Asn Asn Gln
    210                 215                 220

Lys Ile Val Asn Ile Lys Glu Lys Val Ala Gln Ile Glu Ala Gly Gly
225                 230                 235                 240

Gly Gly Ser Gly Gly Gly Gly Ser Asn Asn Gln Lys Ile Val Asn Ile
                245                 250                 255

Lys Glu Lys Val Ala Gln Ile Glu Ala Gly Gly Gly Gly Ser Gly Gly
            260                 265                 270

Gly Gly Ser Asn Asn Gln Lys Ile Val Asn Ile Lys Glu Lys Val Ala
        275                 280                 285

Gln Ile Glu Ala Gly Gly Gly Gly Ser Gly Gly Gly Gly Ser Gly Phe
    290                 295                 300

Leu Gly His Pro Leu Ser Pro Gln Gly His Pro Ala Arg Leu His Arg
305                 310                 315                 320

Ile Val Pro Arg Leu Arg Asp Val Phe Gly Trp Gly Asn Leu Thr Cys
                325                 330                 335

Pro Ile Cys Lys Gly Leu Phe Thr Ala Ile Asn Leu Gly Leu Lys Lys
            340                 345                 350

Glu Pro Asn Val Ala Arg Val Gly Ser Val Ala Ile Lys Leu Cys Asn
        355                 360                 365

Leu Leu Lys Ile Ala Pro Pro Ala Val Cys Gln Ser Ile Val His Leu
    370                 375                 380

Phe Glu Asp Asp Met Val Glu Val Trp Arg Arg Ser Val Leu Ser Pro
385                 390                 395                 400

Ser Glu Ala Cys Gly Leu Leu Leu Gly Ser Thr Cys Gly His Trp Asp
                405                 410                 415

Ile Phe Ser Ser Trp Asn Ile Ser Leu Pro Thr Val Pro Lys Pro Pro
            420                 425                 430

Pro Lys Pro Pro Ser Pro Pro Ala Pro Gly Ala Pro Val Ser Arg Ile
        435                 440                 445

Leu Phe Leu Thr Asp Leu His Trp Asp His Asp Tyr Leu Glu Gly Thr
    450                 455                 460

Asp Pro Asp Cys Ala Asp Pro Leu Cys Cys Arg Arg Gly Ser Gly Leu
465                 470                 475                 480

Pro Pro Ala Ser Arg Pro Gly Ala Gly Tyr Trp Gly Glu Tyr Ser Lys
                485                 490                 495

Cys Asp Leu Pro Leu Arg Thr Leu Glu Ser Leu Leu Ser Gly Leu Gly
            500                 505                 510

Pro Ala Gly Pro Phe Asp Met Val Tyr Trp Thr Gly Asp Ile Pro Ala
        515                 520                 525

His Asp Val Trp His Gln Thr Arg Gln Asp Gln Leu Arg Ala Leu Thr
    530                 535                 540

Thr Val Thr Ala Leu Val Arg Lys Phe Leu Gly Pro Val Pro Val Tyr
545                 550                 555                 560

Pro Ala Val Gly Asn His Glu Ser Thr Pro Val Asn Ser Phe Pro Pro
                565                 570                 575

Pro Phe Ile Glu Gly Asn His Ser Ser Arg Trp Leu Tyr Glu Ala Met
```

580 585 590

Ala Lys Ala Trp Glu Pro Trp Leu Pro Ala Glu Ala Leu Arg Thr Leu
595 600 605

Arg Ile Gly Gly Phe Tyr Ala Leu Ser Pro Tyr Pro Gly Leu Arg Leu
610 615 620

Ile Ser Leu Asn Met Asn Phe Cys Ser Arg Glu Asn Phe Trp Leu Leu
625 630 635 640

Ile Asn Ser Thr Asp Pro Ala Gly Gln Leu Gln Trp Leu Val Gly Glu
645 650 655

Leu Gln Ala Ala Glu Asp Arg Gly Asp Lys Val His Ile Ile Gly His
660 665 670

Ile Pro Pro Gly His Cys Leu Lys Ser Trp Ser Trp Asn Tyr Tyr Arg
675 680 685

Ile Val Ala Arg Tyr Glu Asn Thr Leu Ala Ala Gln Phe Phe Gly His
690 695 700

Thr His Val Asp Glu Phe Glu Val Phe Tyr Asp Glu Glu Thr Leu Ser
705 710 715 720

Arg Pro Leu Ala Val Ala Phe Leu Ala Pro Ser Ala Thr Thr Tyr Ile
725 730 735

Gly Leu Asn Pro Gly Tyr Arg Val Tyr Gln Ile Asp Gly Asn Tyr Ser
740 745 750

Gly Ser Ser His Val Val Leu Asp His Glu Thr Tyr Ile Leu Asn Leu
755 760 765

Thr Gln Ala Asn Ile Pro Gly Ala Ile Pro His Trp Gln Leu Leu Tyr
770 775 780

Arg Ala Arg Glu Thr Tyr Gly Leu Pro Asn Thr Leu Pro Thr Ala Trp
785 790 795 800

His Asn Leu Val Tyr Arg Met Arg Gly Asp Met Gln Leu Phe Gln Thr
805 810 815

Phe Trp Phe Leu Tyr His Lys Gly His Pro Pro Ser Glu Pro Cys Gly
820 825 830

Thr Pro Cys Arg Leu Ala Thr Leu Cys Ala Gln Leu Ser Ala Arg Ala
835 840 845

Asp Ser Pro Ala Leu Cys Arg His Leu Met Pro Asp Gly Ser Leu Pro
850 855 860

Glu Ala Gln Ser Leu Trp Pro Arg Pro Leu Phe Cys
865 870 875

<210> SEQ ID NO 16
<211> LENGTH: 741
<212> TYPE: PRT
<213> ORGANISM: artificial sequence
<220> FEATURE:
<223> OTHER INFORMATION: Amino acid sequence of the expression cassette for human ASM with five tandem-repeats of the 2?gamma ICAM-1-targeting peptide at the carboxyl terminus

<400> SEQUENCE: 16

Met Glu Thr Asp Thr Leu Leu Leu Trp Val Leu Leu Leu Trp Val Pro
1 5 10 15

Gly Ser Thr Gly Asp His His His His His His Asp Asp Asp Asp Lys
20 25 30

His Pro Leu Ser Pro Gln Gly His Pro Ala Arg Leu His Arg Ile Val
35 40 45

Pro Arg Leu Arg Asp Val Phe Gly Trp Gly Asn Leu Thr Cys Pro Ile
50 55 60

-continued

```
Cys Lys Gly Leu Phe Thr Ala Ile Asn Leu Gly Leu Lys Lys Glu Pro
65                  70                  75                  80

Asn Val Ala Arg Val Gly Ser Val Ala Ile Lys Leu Cys Asn Leu Leu
                85                  90                  95

Lys Ile Ala Pro Pro Ala Val Cys Gln Ser Ile Val His Leu Phe Glu
            100                 105                 110

Asp Asp Met Val Glu Val Trp Arg Arg Ser Val Leu Ser Pro Ser Glu
        115                 120                 125

Ala Cys Gly Leu Leu Leu Gly Ser Thr Cys Gly His Trp Asp Ile Phe
    130                 135                 140

Ser Ser Trp Asn Ile Ser Leu Pro Thr Val Pro Lys Pro Pro Pro Lys
145                 150                 155                 160

Pro Pro Ser Pro Pro Ala Pro Gly Ala Pro Val Ser Arg Ile Leu Phe
                165                 170                 175

Leu Thr Asp Leu His Trp Asp His Asp Tyr Leu Glu Gly Thr Asp Pro
            180                 185                 190

Asp Cys Ala Asp Pro Leu Cys Cys Arg Arg Gly Ser Gly Leu Pro Pro
        195                 200                 205

Ala Ser Arg Pro Gly Ala Gly Tyr Trp Gly Glu Tyr Ser Lys Cys Asp
    210                 215                 220

Leu Pro Leu Arg Thr Leu Glu Ser Leu Leu Ser Gly Leu Gly Pro Ala
225                 230                 235                 240

Gly Pro Phe Asp Met Val Tyr Trp Thr Gly Asp Ile Pro Ala His Asp
                245                 250                 255

Val Trp His Gln Thr Arg Gln Asp Gln Leu Arg Ala Leu Thr Thr Val
            260                 265                 270

Thr Ala Leu Val Arg Lys Phe Leu Gly Pro Val Pro Val Tyr Pro Ala
        275                 280                 285

Val Gly Asn His Glu Ser Thr Pro Val Asn Ser Phe Pro Pro Pro Phe
    290                 295                 300

Ile Glu Gly Asn His Ser Ser Arg Trp Leu Tyr Glu Ala Met Ala Lys
305                 310                 315                 320

Ala Trp Glu Pro Trp Leu Pro Ala Glu Ala Leu Arg Thr Leu Arg Ile
                325                 330                 335

Gly Gly Phe Tyr Ala Leu Ser Pro Tyr Pro Gly Leu Arg Leu Ile Ser
            340                 345                 350

Leu Asn Met Asn Phe Cys Ser Arg Glu Asn Phe Trp Leu Leu Ile Asn
        355                 360                 365

Ser Thr Asp Pro Ala Gly Gln Leu Gln Trp Leu Val Gly Glu Leu Gln
    370                 375                 380

Ala Ala Glu Asp Arg Gly Asp Lys Val His Ile Ile Gly His Ile Pro
385                 390                 395                 400

Pro Gly His Cys Leu Lys Ser Trp Ser Trp Asn Tyr Tyr Arg Ile Val
                405                 410                 415

Ala Arg Tyr Glu Asn Thr Leu Ala Ala Gln Phe Phe Gly His Thr His
            420                 425                 430

Val Asp Glu Phe Glu Val Phe Tyr Asp Glu Glu Thr Leu Ser Arg Pro
        435                 440                 445

Leu Ala Val Ala Phe Leu Ala Pro Ser Ala Thr Thr Tyr Ile Gly Leu
    450                 455                 460

Asn Pro Gly Tyr Arg Val Tyr Gln Ile Asp Gly Asn Tyr Ser Gly Ser
465                 470                 475                 480
```

-continued

Ser His Val Val Leu Asp His Glu Thr Tyr Ile Leu Asn Leu Thr Gln
485 490 495

Ala Asn Ile Pro Gly Ala Ile Pro His Trp Gln Leu Leu Tyr Arg Ala
500 505 510

Arg Glu Thr Tyr Gly Leu Pro Asn Thr Leu Pro Thr Ala Trp His Asn
515 520 525

Leu Val Tyr Arg Met Arg Gly Asp Met Gln Leu Phe Gln Thr Phe Trp
530 535 540

Phe Leu Tyr His Lys Gly His Pro Pro Ser Glu Pro Cys Gly Thr Pro
545 550 555 560

Cys Arg Leu Ala Thr Leu Cys Ala Gln Leu Ser Ala Arg Ala Asp Ser
565 570 575

Pro Ala Leu Cys Arg His Leu Met Pro Asp Gly Ser Leu Pro Glu Ala
580 585 590

Gln Ser Leu Trp Pro Arg Pro Leu Phe Cys Gly Phe Leu Gly Gly Gly
595 600 605

Gly Gly Ser Gly Gly Gly Gly Ser Asn Asn Gln Lys Ile Val Asn Ile
610 615 620

Lys Glu Lys Val Ala Gln Ile Glu Ala Gly Gly Gly Gly Ser Gly Gly
625 630 635 640

Gly Gly Ser Asn Asn Gln Lys Ile Val Asn Ile Lys Glu Lys Val Ala
645 650 655

Gln Ile Glu Ala Gly Gly Gly Gly Ser Gly Gly Gly Gly Ser Asn Asn
660 665 670

Gln Lys Ile Val Asn Ile Lys Glu Lys Val Ala Gln Ile Glu Ala Gly
675 680 685

Gly Gly Gly Ser Gly Gly Gly Gly Ser Asn Asn Gln Lys Ile Val Asn
690 695 700

Ile Lys Glu Lys Val Ala Gln Ile Glu Ala Gly Gly Gly Gly Ser Gly
705 710 715 720

Gly Gly Gly Ser Asn Asn Gln Lys Ile Val Asn Ile Lys Glu Lys Val
725 730 735

Ala Gln Ile Glu Ala
740

<210> SEQ ID NO 17
<211> LENGTH: 602
<212> TYPE: PRT
<213> ORGANISM: artificial sequence
<220> FEATURE:
<223> OTHER INFORMATION: Amino acid sequence of the expression cassette
for human ASM control

<400> SEQUENCE: 17

Met Glu Thr Asp Thr Leu Leu Leu Trp Val Leu Leu Leu Trp Val Pro
1 5 10 15

Gly Ser Thr Gly Asp His His His His His His Asp Asp Asp Asp Lys
20 25 30

His Pro Leu Ser Pro Gln Gly His Pro Ala Arg Leu His Arg Ile Val
35 40 45

Pro Arg Leu Arg Asp Val Phe Gly Trp Gly Asn Leu Thr Cys Pro Ile
50 55 60

Cys Lys Gly Leu Phe Thr Ala Ile Asn Leu Gly Leu Lys Lys Glu Pro
65 70 75 80

Asn Val Ala Arg Val Gly Ser Val Ala Ile Lys Leu Cys Asn Leu Leu
85 90 95

-continued

```
Lys Ile Ala Pro Pro Ala Val Cys Gln Ser Ile Val His Leu Phe Glu
            100                 105                 110

Asp Asp Met Val Glu Val Trp Arg Arg Ser Val Leu Ser Pro Ser Glu
        115                 120                 125

Ala Cys Gly Leu Leu Leu Gly Ser Thr Cys Gly His Trp Asp Ile Phe
    130                 135                 140

Ser Ser Trp Asn Ile Ser Leu Pro Thr Val Pro Lys Pro Pro Pro Lys
145                 150                 155                 160

Pro Pro Ser Pro Pro Ala Pro Gly Ala Pro Val Ser Arg Ile Leu Phe
                165                 170                 175

Leu Thr Asp Leu His Trp Asp His Asp Tyr Leu Glu Gly Thr Asp Pro
            180                 185                 190

Asp Cys Ala Asp Pro Leu Cys Cys Arg Arg Gly Ser Gly Leu Pro Pro
        195                 200                 205

Ala Ser Arg Pro Gly Ala Gly Tyr Trp Gly Glu Tyr Ser Lys Cys Asp
    210                 215                 220

Leu Pro Leu Arg Thr Leu Glu Ser Leu Leu Ser Gly Leu Gly Pro Ala
225                 230                 235                 240

Gly Pro Phe Asp Met Val Tyr Trp Thr Gly Asp Ile Pro Ala His Asp
                245                 250                 255

Val Trp His Gln Thr Arg Gln Asp Gln Leu Arg Ala Leu Thr Thr Val
            260                 265                 270

Thr Ala Leu Val Arg Lys Phe Leu Gly Pro Val Pro Val Tyr Pro Ala
        275                 280                 285

Val Gly Asn His Glu Ser Thr Pro Val Asn Ser Phe Pro Pro Pro Phe
    290                 295                 300

Ile Glu Gly Asn His Ser Ser Arg Trp Leu Tyr Glu Ala Met Ala Lys
305                 310                 315                 320

Ala Trp Glu Pro Trp Leu Pro Ala Glu Ala Leu Arg Thr Leu Arg Ile
                325                 330                 335

Gly Gly Phe Tyr Ala Leu Ser Pro Tyr Pro Gly Leu Arg Leu Ile Ser
            340                 345                 350

Leu Asn Met Asn Phe Cys Ser Arg Glu Asn Phe Trp Leu Leu Ile Asn
        355                 360                 365

Ser Thr Asp Pro Ala Gly Gln Leu Gln Trp Leu Val Gly Glu Leu Gln
    370                 375                 380

Ala Ala Glu Asp Arg Gly Asp Lys Val His Ile Ile Gly His Ile Pro
385                 390                 395                 400

Pro Gly His Cys Leu Lys Ser Trp Ser Trp Asn Tyr Tyr Arg Ile Val
                405                 410                 415

Ala Arg Tyr Glu Asn Thr Leu Ala Ala Gln Phe Phe Gly His Thr His
            420                 425                 430

Val Asp Glu Phe Glu Val Phe Tyr Asp Glu Glu Thr Leu Ser Arg Pro
        435                 440                 445

Leu Ala Val Ala Phe Leu Ala Pro Ser Ala Thr Thr Tyr Ile Gly Leu
    450                 455                 460

Asn Pro Gly Tyr Arg Val Tyr Gln Ile Asp Gly Asn Tyr Ser Gly Ser
465                 470                 475                 480

Ser His Val Val Leu Asp His Glu Thr Tyr Ile Leu Asn Leu Thr Gln
                485                 490                 495

Ala Asn Ile Pro Gly Ala Ile Pro His Trp Gln Leu Leu Tyr Arg Ala
            500                 505                 510
```

-continued

```
Arg Glu Thr Tyr Gly Leu Pro Asn Thr Leu Pro Thr Ala Trp His Asn
        515                 520                 525

Leu Val Tyr Arg Met Arg Gly Asp Met Gln Leu Phe Gln Thr Phe Trp
    530                 535                 540

Phe Leu Tyr His Lys Gly His Pro Pro Ser Glu Pro Cys Gly Thr Pro
545                 550                 555                 560

Cys Arg Leu Ala Thr Leu Cys Ala Gln Leu Ser Ala Arg Ala Asp Ser
                565                 570                 575

Pro Ala Leu Cys Arg His Leu Met Pro Asp Gly Ser Leu Pro Glu Ala
            580                 585                 590

Gln Ser Leu Trp Pro Arg Pro Leu Phe Cys
        595                 600


<210> SEQ ID NO 18
<211> LENGTH: 460
<212> TYPE: PRT
<213> ORGANISM: artificial sequence
<220> FEATURE:
<223> OTHER INFORMATION: Amino acid sequence of the expression cassette
      for human alpha galactosidase with one copy of the 2gamma3
      ICAM-1-targeting peptide at the amino terminus

<400> SEQUENCE: 18

Met Gly Trp Ser Cys Ile Ile Leu Phe Leu Val Ala Thr Ala Thr Gly
1               5                   10                  15

Val His Ser Asp His His His His His His Asp Asp Asp Asp Lys Asn
            20                  25                  30

Asn Gln Lys Ile Val Asn Ile Lys Glu Lys Val Ala Gln Ile Glu Ala
        35                  40                  45

Gly Gly Gly Gly Ser Gly Gly Gly Gly Ser Gly Phe Leu Gly Leu Asp
    50                  55                  60

Asn Gly Leu Ala Arg Thr Pro Thr Met Gly Trp Leu His Trp Glu Arg
65                  70                  75                  80

Phe Met Cys Asn Leu Asp Cys Gln Glu Glu Pro Asp Ser Cys Ile Ser
                85                  90                  95

Glu Lys Leu Phe Met Glu Met Ala Glu Leu Met Val Ser Glu Gly Trp
            100                 105                 110

Lys Asp Ala Gly Tyr Glu Tyr Leu Cys Ile Asp Asp Cys Trp Met Ala
        115                 120                 125

Pro Gln Arg Asp Ser Glu Gly Arg Leu Gln Ala Asp Pro Gln Arg Phe
    130                 135                 140

Pro His Gly Ile Arg Gln Leu Ala Asn Tyr Val His Ser Lys Gly Leu
145                 150                 155                 160

Lys Leu Gly Ile Tyr Ala Asp Val Gly Asn Lys Thr Cys Ala Gly Phe
                165                 170                 175

Pro Gly Ser Phe Gly Tyr Tyr Asp Ile Asp Ala Gln Thr Phe Ala Asp
            180                 185                 190

Trp Gly Val Asp Leu Leu Lys Phe Asp Gly Cys Tyr Cys Asp Ser Leu
        195                 200                 205

Glu Asn Leu Ala Asp Gly Tyr Lys His Met Ser Leu Ala Leu Asn Arg
    210                 215                 220

Thr Gly Arg Ser Ile Val Tyr Ser Cys Glu Trp Pro Leu Tyr Met Trp
225                 230                 235                 240

Pro Phe Gln Lys Pro Asn Tyr Thr Glu Ile Arg Gln Tyr Cys Asn His
                245                 250                 255

Trp Arg Asn Phe Ala Asp Ile Asp Asp Ser Trp Lys Ser Ile Lys Ser
```

```
            260                 265                 270

Ile Leu Asp Trp Thr Ser Phe Asn Gln Glu Arg Ile Val Asp Val Ala
        275                 280                 285

Gly Pro Gly Gly Trp Asn Asp Pro Asp Met Leu Val Ile Gly Asn Phe
    290                 295                 300

Gly Leu Ser Trp Asn Gln Gln Val Thr Gln Met Ala Leu Trp Ala Ile
305                 310                 315                 320

Met Ala Ala Pro Leu Phe Met Ser Asn Asp Leu Arg His Ile Ser Pro
                325                 330                 335

Gln Ala Lys Ala Leu Leu Gln Asp Lys Asp Val Ile Ala Ile Asn Gln
            340                 345                 350

Asp Pro Leu Gly Lys Gln Gly Tyr Gln Leu Arg Gln Gly Asp Asn Phe
        355                 360                 365

Glu Val Trp Glu Arg Pro Leu Ser Gly Leu Ala Trp Ala Val Ala Met
    370                 375                 380

Ile Asn Arg Gln Glu Ile Gly Gly Pro Arg Ser Tyr Thr Ile Ala Val
385                 390                 395                 400

Ala Ser Leu Gly Lys Gly Val Ala Cys Asn Pro Ala Cys Phe Ile Thr
                405                 410                 415

Gln Leu Leu Pro Val Lys Arg Lys Leu Gly Phe Tyr Glu Trp Thr Ser
            420                 425                 430

Arg Leu Arg Ser His Ile Asn Pro Thr Gly Thr Val Leu Leu Gln Leu
        435                 440                 445

Glu Asn Thr Met Gln Met Ser Leu Lys Asp Leu Leu
    450                 455                 460


<210> SEQ ID NO 19
<211> LENGTH: 568
<212> TYPE: PRT
<213> ORGANISM: artificial sequence
<220> FEATURE:
<223> OTHER INFORMATION: Amino acid sequence of the expression cassette
      for human alphaGal with five tandem-repeats of the 2beta3
      ICAM-1-targeting peptide at the carboxyl terminus

<400> SEQUENCE: 19

Met Gly Trp Ser Cys Ile Ile Leu Phe Leu Val Ala Thr Ala Thr Gly
1               5                   10                  15

Val His Ser Asp His His His His His His Asp Asp Asp Asp Lys Leu
            20                  25                  30

Asp Asn Gly Leu Ala Arg Thr Pro Thr Met Gly Trp Leu His Trp Glu
        35                  40                  45

Arg Phe Met Cys Asn Leu Asp Cys Gln Glu Glu Pro Asp Ser Cys Ile
    50                  55                  60

Ser Glu Lys Leu Phe Met Glu Met Ala Glu Leu Met Val Ser Glu Gly
65                  70                  75                  80

Trp Lys Asp Ala Gly Tyr Glu Tyr Leu Cys Ile Asp Asp Cys Trp Met
                85                  90                  95

Ala Pro Gln Arg Asp Ser Glu Gly Arg Leu Gln Ala Asp Pro Gln Arg
            100                 105                 110

Phe Pro His Gly Ile Arg Gln Leu Ala Asn Tyr Val His Ser Lys Gly
        115                 120                 125

Leu Lys Leu Gly Ile Tyr Ala Asp Val Gly Asn Lys Thr Cys Ala Gly
    130                 135                 140

Phe Pro Gly Ser Phe Gly Tyr Tyr Asp Ile Asp Ala Gln Thr Phe Ala
145                 150                 155                 160
```

-continued

```
Asp Trp Gly Val Asp Leu Leu Lys Phe Asp Gly Cys Tyr Cys Asp Ser
                165                 170                 175

Leu Glu Asn Leu Ala Asp Gly Tyr Lys His Met Ser Leu Ala Leu Asn
            180                 185                 190

Arg Thr Gly Arg Ser Ile Val Tyr Ser Cys Glu Trp Pro Leu Tyr Met
        195                 200                 205

Trp Pro Phe Gln Lys Pro Asn Tyr Thr Glu Ile Arg Gln Tyr Cys Asn
    210                 215                 220

His Trp Arg Asn Phe Ala Asp Ile Asp Asp Ser Trp Lys Ser Ile Lys
225                 230                 235                 240

Ser Ile Leu Asp Trp Thr Ser Phe Asn Gln Glu Arg Ile Val Asp Val
                245                 250                 255

Ala Gly Pro Gly Gly Trp Asn Asp Pro Asp Met Leu Val Ile Gly Asn
            260                 265                 270

Phe Gly Leu Ser Trp Asn Gln Gln Val Thr Gln Met Ala Leu Trp Ala
        275                 280                 285

Ile Met Ala Ala Pro Leu Phe Met Ser Asn Asp Leu Arg His Ile Ser
    290                 295                 300

Pro Gln Ala Lys Ala Leu Leu Gln Asp Lys Asp Val Ile Ala Ile Asn
305                 310                 315                 320

Gln Asp Pro Leu Gly Lys Gln Gly Tyr Gln Leu Arg Gln Gly Asp Asn
                325                 330                 335

Phe Glu Val Trp Glu Arg Pro Leu Ser Gly Leu Ala Trp Ala Val Ala
            340                 345                 350

Met Ile Asn Arg Gln Glu Ile Gly Gly Pro Arg Ser Tyr Thr Ile Ala
        355                 360                 365

Val Ala Ser Leu Gly Lys Gly Val Ala Cys Asn Pro Ala Cys Phe Ile
    370                 375                 380

Thr Gln Leu Leu Pro Val Lys Arg Lys Leu Gly Phe Tyr Glu Trp Thr
385                 390                 395                 400

Ser Arg Leu Arg Ser His Ile Asn Pro Thr Gly Thr Val Leu Leu Gln
                405                 410                 415

Leu Glu Asn Thr Met Gln Met Ser Leu Lys Asp Leu Leu Gly Phe Leu
            420                 425                 430

Gly Gly Gly Gly Gly Ser Gly Gly Gly Gly Ser Asn Asn Gln Lys Ile
        435                 440                 445

Val Asn Ile Lys Glu Lys Val Ala Gln Ile Glu Ala Gly Gly Gly Gly
    450                 455                 460

Ser Gly Gly Gly Gly Ser Asn Asn Gln Lys Ile Val Asn Ile Lys Glu
465                 470                 475                 480

Lys Val Ala Gln Ile Glu Ala Gly Gly Gly Gly Ser Gly Gly Gly Gly
                485                 490                 495

Ser Asn Asn Gln Lys Ile Val Asn Ile Lys Glu Lys Val Ala Gln Ile
            500                 505                 510

Glu Ala Gly Gly Gly Gly Ser Gly Gly Gly Gly Ser Asn Asn Gln Lys
        515                 520                 525

Ile Val Asn Ile Lys Glu Lys Val Ala Gln Ile Glu Ala Gly Gly Gly
    530                 535                 540

Gly Ser Gly Gly Gly Gly Ser Asn Asn Gln Lys Ile Val Asn Ile Lys
545                 550                 555                 560

Glu Lys Val Ala Gln Ile Glu Ala
                565
```

<210> SEQ ID NO 20
<211> LENGTH: 429
<212> TYPE: PRT
<213> ORGANISM: artificial sequence
<220> FEATURE:
<223> OTHER INFORMATION: Amino acid sequence of the expression cassette
for human alphaGal control

<400> SEQUENCE: 20

```
Met Gly Trp Ser Cys Ile Ile Leu Phe Leu Val Ala Thr Ala Thr Gly
1               5                   10                  15

Val His Ser Asp His His His His His His Asp Asp Asp Asp Lys Leu
            20                  25                  30

Asp Asn Gly Leu Ala Arg Thr Pro Thr Met Gly Trp Leu His Trp Glu
        35                  40                  45

Arg Phe Met Cys Asn Leu Asp Cys Gln Glu Glu Pro Asp Ser Cys Ile
    50                  55                  60

Ser Glu Lys Leu Phe Met Glu Met Ala Glu Leu Met Val Ser Glu Gly
65                  70                  75                  80

Trp Lys Asp Ala Gly Tyr Glu Tyr Leu Cys Ile Asp Asp Cys Trp Met
                85                  90                  95

Ala Pro Gln Arg Asp Ser Glu Gly Arg Leu Gln Ala Asp Pro Gln Arg
            100                 105                 110

Phe Pro His Gly Ile Arg Gln Leu Ala Asn Tyr Val His Ser Lys Gly
        115                 120                 125

Leu Lys Leu Gly Ile Tyr Ala Asp Val Gly Asn Lys Thr Cys Ala Gly
    130                 135                 140

Phe Pro Gly Ser Phe Gly Tyr Tyr Asp Ile Asp Ala Gln Thr Phe Ala
145                 150                 155                 160

Asp Trp Gly Val Asp Leu Leu Lys Phe Asp Gly Cys Tyr Cys Asp Ser
                165                 170                 175

Leu Glu Asn Leu Ala Asp Gly Tyr Lys His Met Ser Leu Ala Leu Asn
            180                 185                 190

Arg Thr Gly Arg Ser Ile Val Tyr Ser Cys Glu Trp Pro Leu Tyr Met
        195                 200                 205

Trp Pro Phe Gln Lys Pro Asn Tyr Thr Glu Ile Arg Gln Tyr Cys Asn
    210                 215                 220

His Trp Arg Asn Phe Ala Asp Ile Asp Asp Ser Trp Lys Ser Ile Lys
225                 230                 235                 240

Ser Ile Leu Asp Trp Thr Ser Phe Asn Gln Glu Arg Ile Val Asp Val
                245                 250                 255

Ala Gly Pro Gly Gly Trp Asn Asp Pro Asp Met Leu Val Ile Gly Asn
            260                 265                 270

Phe Gly Leu Ser Trp Asn Gln Gln Val Thr Gln Met Ala Leu Trp Ala
        275                 280                 285

Ile Met Ala Ala Pro Leu Phe Met Ser Asn Asp Leu Arg His Ile Ser
    290                 295                 300

Pro Gln Ala Lys Ala Leu Leu Gln Asp Lys Asp Val Ile Ala Ile Asn
305                 310                 315                 320

Gln Asp Pro Leu Gly Lys Gln Gly Tyr Gln Leu Arg Gln Gly Asp Asn
                325                 330                 335

Phe Glu Val Trp Glu Arg Pro Leu Ser Gly Leu Ala Trp Ala Val Ala
            340                 345                 350

Met Ile Asn Arg Gln Glu Ile Gly Gly Pro Arg Ser Tyr Thr Ile Ala
        355                 360                 365
```

```
Val Ala Ser Leu Gly Lys Gly Val Ala Cys Asn Pro Ala Cys Phe Ile
    370                 375                 380

Thr Gln Leu Leu Pro Val Lys Arg Lys Leu Gly Phe Tyr Glu Trp Thr
385                 390                 395                 400

Ser Arg Leu Arg Ser His Ile Asn Pro Thr Gly Thr Val Leu Leu Gln
                405                 410                 415

Leu Glu Asn Thr Met Gln Met Ser Leu Lys Asp Leu Leu
            420                 425


<210> SEQ ID NO 21
<211> LENGTH: 559
<212> TYPE: PRT
<213> ORGANISM: artificial sequence
<220> FEATURE:
<223> OTHER INFORMATION: Amino acid sequence of the expression cassette
      for human glucocerebrosidase (GCase) with one copy of the 2gamma3
      ICAM-1-targeting peptide at the amino terminus

<400> SEQUENCE: 21

Met Gly Trp Ser Cys Ile Ile Leu Phe Leu Val Ala Thr Ala Thr Gly
1               5                   10                  15

Val His Ser Asp His His His His His His Asp Asp Asp Asp Lys Asn
            20                  25                  30

Asn Gln Lys Ile Val Asn Ile Lys Glu Lys Val Ala Gln Ile Glu Ala
        35                  40                  45

Gly Gly Gly Gly Ser Gly Gly Gly Gly Ser Gly Phe Leu Gly Ala Arg
    50                  55                  60

Pro Cys Ile Pro Lys Ser Phe Gly Tyr Ser Ser Val Val Cys Val Cys
65                  70                  75                  80

Asn Ala Thr Tyr Cys Asp Ser Phe Asp Pro Pro Thr Phe Pro Ala Leu
                85                  90                  95

Gly Thr Phe Ser Arg Tyr Glu Ser Thr Arg Ser Gly Arg Arg Met Glu
            100                 105                 110

Leu Ser Met Gly Pro Ile Gln Ala Asn His Thr Gly Thr Gly Leu Leu
        115                 120                 125

Leu Thr Leu Gln Pro Glu Gln Lys Phe Gln Lys Val Lys Gly Phe Gly
    130                 135                 140

Gly Ala Met Thr Asp Ala Ala Ala Leu Asn Ile Leu Ala Leu Ser Pro
145                 150                 155                 160

Pro Ala Gln Asn Leu Leu Leu Lys Ser Tyr Phe Ser Glu Glu Gly Ile
                165                 170                 175

Gly Tyr Asn Ile Ile Arg Val Pro Met Ala Ser Cys Asp Phe Ser Ile
            180                 185                 190

Arg Thr Tyr Thr Tyr Ala Asp Thr Pro Asp Asp Phe Gln Leu His Asn
        195                 200                 205

Phe Ser Leu Pro Glu Glu Asp Thr Lys Leu Lys Ile Pro Leu Ile His
    210                 215                 220

Arg Ala Leu Gln Leu Ala Gln Arg Pro Val Ser Leu Leu Ala Ser Pro
225                 230                 235                 240

Trp Thr Ser Pro Thr Trp Leu Lys Thr Asn Gly Ala Val Asn Gly Lys
                245                 250                 255

Gly Ser Leu Lys Gly Gln Pro Gly Asp Ile Tyr His Gln Thr Trp Ala
            260                 265                 270

Arg Tyr Phe Val Lys Phe Leu Asp Ala Tyr Ala Glu His Lys Leu Gln
        275                 280                 285
```

```
Phe Trp Ala Val Thr Ala Glu Asn Glu Pro Ser Ala Gly Leu Leu Ser
    290                 295                 300

Gly Tyr Pro Phe Gln Cys Leu Gly Phe Thr Pro Glu His Gln Arg Asp
305                 310                 315                 320

Phe Ile Ala Arg Asp Leu Gly Pro Thr Leu Ala Asn Ser Thr His His
                325                 330                 335

Asn Val Arg Leu Leu Met Leu Asp Asp Gln Arg Leu Leu Leu Pro His
            340                 345                 350

Trp Ala Lys Val Val Leu Thr Asp Pro Glu Ala Ala Lys Tyr Val His
        355                 360                 365

Gly Ile Ala Val His Trp Tyr Leu Asp Phe Leu Ala Pro Ala Lys Ala
    370                 375                 380

Thr Leu Gly Glu Thr His Arg Leu Phe Pro Asn Thr Met Leu Phe Ala
385                 390                 395                 400

Ser Glu Ala Cys Val Gly Ser Lys Phe Trp Glu Gln Ser Val Arg Leu
                405                 410                 415

Gly Ser Trp Asp Arg Gly Met Gln Tyr Ser His Ser Ile Ile Thr Asn
            420                 425                 430

Leu Leu Tyr His Val Val Gly Trp Thr Asp Trp Asn Leu Ala Leu Asn
        435                 440                 445

Pro Glu Gly Gly Pro Asn Trp Val Arg Asn Phe Val Asp Ser Pro Ile
    450                 455                 460

Ile Val Asp Ile Thr Lys Asp Thr Phe Tyr Lys Gln Pro Met Phe Tyr
465                 470                 475                 480

His Leu Gly His Phe Ser Lys Phe Ile Pro Glu Gly Ser Gln Arg Val
                485                 490                 495

Gly Leu Val Ala Ser Gln Lys Asn Asp Leu Asp Ala Val Ala Leu Met
            500                 505                 510

His Pro Asp Gly Ser Ala Val Val Val Val Leu Asn Arg Ser Ser Lys
        515                 520                 525

Asp Val Pro Leu Thr Ile Lys Asp Pro Ala Val Gly Phe Leu Glu Thr
    530                 535                 540

Ile Ser Pro Gly Tyr Ser Ile His Thr Tyr Leu Trp Arg Arg Gln
545                 550                 555
```

```
<210> SEQ ID NO 22
<211> LENGTH: 667
<212> TYPE: PRT
<213> ORGANISM: artificial sequence
<220> FEATURE:
<223> OTHER INFORMATION: Amino acid sequence of the expression cassette
      for human GCase with five tandem-repeats of the 2gamma3
      ICAM-1-targeting peptide at the amino terminus

<400> SEQUENCE: 22

Met Gly Trp Ser Cys Ile Ile Leu Phe Leu Val Ala Thr Ala Thr Gly
1               5                   10                  15

Val His Ser Asp His His His His His His Asp Asp Asp Asp Lys Asn
            20                  25                  30

Asn Gln Lys Ile Val Asn Ile Lys Glu Lys Val Ala Gln Ile Glu Ala
        35                  40                  45

Gly Gly Gly Gly Ser Gly Gly Gly Gly Ser Asn Asn Gln Lys Ile Val
    50                  55                  60

Asn Ile Lys Glu Lys Val Ala Gln Ile Glu Ala Gly Gly Gly Gly Ser
65                  70                  75                  80

Gly Gly Gly Gly Ser Asn Asn Gln Lys Ile Val Asn Ile Lys Glu Lys
```

-continued

```
                85                  90                  95

Val Ala Gln Ile Glu Ala Gly Gly Gly Gly Ser Gly Gly Gly Gly Ser
            100                 105                 110

Asn Asn Gln Lys Ile Val Asn Ile Lys Glu Lys Val Ala Gln Ile Glu
        115                 120                 125

Ala Gly Gly Gly Gly Ser Gly Gly Gly Gly Ser Asn Asn Gln Lys Ile
    130                 135                 140

Val Asn Ile Lys Glu Lys Val Ala Gln Ile Glu Ala Gly Gly Gly Gly
145                 150                 155                 160

Ser Gly Gly Gly Gly Ser Gly Phe Leu Gly Ala Arg Pro Cys Ile Pro
                165                 170                 175

Lys Ser Phe Gly Tyr Ser Ser Val Val Cys Val Cys Asn Ala Thr Tyr
            180                 185                 190

Cys Asp Ser Phe Asp Pro Pro Thr Phe Pro Ala Leu Gly Thr Phe Ser
        195                 200                 205

Arg Tyr Glu Ser Thr Arg Ser Gly Arg Arg Met Glu Leu Ser Met Gly
    210                 215                 220

Pro Ile Gln Ala Asn His Thr Gly Thr Gly Leu Leu Leu Thr Leu Gln
225                 230                 235                 240

Pro Glu Gln Lys Phe Gln Lys Val Lys Gly Phe Gly Gly Ala Met Thr
                245                 250                 255

Asp Ala Ala Ala Leu Asn Ile Leu Ala Leu Ser Pro Pro Ala Gln Asn
            260                 265                 270

Leu Leu Leu Lys Ser Tyr Phe Ser Glu Glu Gly Ile Gly Tyr Asn Ile
        275                 280                 285

Ile Arg Val Pro Met Ala Ser Cys Asp Phe Ser Ile Arg Thr Tyr Thr
    290                 295                 300

Tyr Ala Asp Thr Pro Asp Asp Phe Gln Leu His Asn Phe Ser Leu Pro
305                 310                 315                 320

Glu Glu Asp Thr Lys Leu Lys Ile Pro Leu Ile His Arg Ala Leu Gln
                325                 330                 335

Leu Ala Gln Arg Pro Val Ser Leu Leu Ala Ser Pro Trp Thr Ser Pro
            340                 345                 350

Thr Trp Leu Lys Thr Asn Gly Ala Val Asn Gly Lys Gly Ser Leu Lys
        355                 360                 365

Gly Gln Pro Gly Asp Ile Tyr His Gln Thr Trp Ala Arg Tyr Phe Val
    370                 375                 380

Lys Phe Leu Asp Ala Tyr Ala Glu His Lys Leu Gln Phe Trp Ala Val
385                 390                 395                 400

Thr Ala Glu Asn Glu Pro Ser Ala Gly Leu Leu Ser Gly Tyr Pro Phe
                405                 410                 415

Gln Cys Leu Gly Phe Thr Pro Glu His Gln Arg Asp Phe Ile Ala Arg
            420                 425                 430

Asp Leu Gly Pro Thr Leu Ala Asn Ser Thr His His Asn Val Arg Leu
        435                 440                 445

Leu Met Leu Asp Asp Gln Arg Leu Leu Leu Pro His Trp Ala Lys Val
    450                 455                 460

Val Leu Thr Asp Pro Glu Ala Ala Lys Tyr Val His Gly Ile Ala Val
465                 470                 475                 480

His Trp Tyr Leu Asp Phe Leu Ala Pro Ala Lys Ala Thr Leu Gly Glu
                485                 490                 495

Thr His Arg Leu Phe Pro Asn Thr Met Leu Phe Ala Ser Glu Ala Cys
            500                 505                 510
```

```
Val Gly Ser Lys Phe Trp Glu Gln Ser Val Arg Leu Gly Ser Trp Asp
        515                 520                 525

Arg Gly Met Gln Tyr Ser His Ser Ile Ile Thr Asn Leu Leu Tyr His
    530                 535                 540

Val Val Gly Trp Thr Asp Trp Asn Leu Ala Leu Asn Pro Glu Gly Gly
545                 550                 555                 560

Pro Asn Trp Val Arg Asn Phe Val Asp Ser Pro Ile Ile Val Asp Ile
                565                 570                 575

Thr Lys Asp Thr Phe Tyr Lys Gln Pro Met Phe Tyr His Leu Gly His
            580                 585                 590

Phe Ser Lys Phe Ile Pro Glu Gly Ser Gln Arg Val Gly Leu Val Ala
        595                 600                 605

Ser Gln Lys Asn Asp Leu Asp Ala Val Ala Leu Met His Pro Asp Gly
    610                 615                 620

Ser Ala Val Val Val Val Leu Asn Arg Ser Ser Lys Asp Val Pro Leu
625                 630                 635                 640

Thr Ile Lys Asp Pro Ala Val Gly Phe Leu Glu Thr Ile Ser Pro Gly
                645                 650                 655

Tyr Ser Ile His Thr Tyr Leu Trp Arg Arg Gln
            660                 665


<210> SEQ ID NO 23
<211> LENGTH: 528
<212> TYPE: PRT
<213> ORGANISM: artificial sequence
<220> FEATURE:
<223> OTHER INFORMATION: Amino acid sequence of the expression cassette
      for human GCase control

<400> SEQUENCE: 23

Met Gly Trp Ser Cys Ile Ile Leu Phe Leu Val Ala Thr Ala Thr Gly
1               5                   10                  15

Val His Ser Asp His His His His His His Asp Asp Asp Asp Lys Ala
            20                  25                  30

Arg Pro Cys Ile Pro Lys Ser Phe Gly Tyr Ser Ser Val Val Cys Val
        35                  40                  45

Cys Asn Ala Thr Tyr Cys Asp Ser Phe Asp Pro Pro Thr Phe Pro Ala
    50                  55                  60

Leu Gly Thr Phe Ser Arg Tyr Glu Ser Thr Arg Ser Gly Arg Arg Met
65                  70                  75                  80

Glu Leu Ser Met Gly Pro Ile Gln Ala Asn His Thr Gly Thr Gly Leu
                85                  90                  95

Leu Leu Thr Leu Gln Pro Glu Gln Lys Phe Gln Lys Val Lys Gly Phe
            100                 105                 110

Gly Gly Ala Met Thr Asp Ala Ala Ala Leu Asn Ile Leu Ala Leu Ser
        115                 120                 125

Pro Pro Ala Gln Asn Leu Leu Leu Lys Ser Tyr Phe Ser Glu Glu Gly
    130                 135                 140

Ile Gly Tyr Asn Ile Ile Arg Val Pro Met Ala Ser Cys Asp Phe Ser
145                 150                 155                 160

Ile Arg Thr Tyr Thr Tyr Ala Asp Thr Pro Asp Asp Phe Gln Leu His
                165                 170                 175

Asn Phe Ser Leu Pro Glu Glu Asp Thr Lys Leu Lys Ile Pro Leu Ile
            180                 185                 190

His Arg Ala Leu Gln Leu Ala Gln Arg Pro Val Ser Leu Leu Ala Ser
```

-continued

```
        195                 200                 205

Pro Trp Thr Ser Pro Thr Trp Leu Lys Thr Asn Gly Ala Val Asn Gly
    210                 215                 220

Lys Gly Ser Leu Lys Gly Gln Pro Gly Asp Ile Tyr His Gln Thr Trp
225                 230                 235                 240

Ala Arg Tyr Phe Val Lys Phe Leu Asp Ala Tyr Ala Glu His Lys Leu
                245                 250                 255

Gln Phe Trp Ala Val Thr Ala Glu Asn Glu Pro Ser Ala Gly Leu Leu
            260                 265                 270

Ser Gly Tyr Pro Phe Gln Cys Leu Gly Phe Thr Pro Glu His Gln Arg
        275                 280                 285

Asp Phe Ile Ala Arg Asp Leu Gly Pro Thr Leu Ala Asn Ser Thr His
    290                 295                 300

His Asn Val Arg Leu Leu Met Leu Asp Asp Gln Arg Leu Leu Leu Pro
305                 310                 315                 320

His Trp Ala Lys Val Val Leu Thr Asp Pro Glu Ala Ala Lys Tyr Val
                325                 330                 335

His Gly Ile Ala Val His Trp Tyr Leu Asp Phe Leu Ala Pro Ala Lys
            340                 345                 350

Ala Thr Leu Gly Glu Thr His Arg Leu Phe Pro Asn Thr Met Leu Phe
        355                 360                 365

Ala Ser Glu Ala Cys Val Gly Ser Lys Phe Trp Glu Gln Ser Val Arg
    370                 375                 380

Leu Gly Ser Trp Asp Arg Gly Met Gln Tyr Ser His Ser Ile Ile Thr
385                 390                 395                 400

Asn Leu Leu Tyr His Val Val Gly Trp Thr Asp Trp Asn Leu Ala Leu
                405                 410                 415

Asn Pro Glu Gly Gly Pro Asn Trp Val Arg Asn Phe Val Asp Ser Pro
            420                 425                 430

Ile Ile Val Asp Ile Thr Lys Asp Thr Phe Tyr Lys Gln Pro Met Phe
        435                 440                 445

Tyr His Leu Gly His Phe Ser Lys Phe Ile Pro Glu Gly Ser Gln Arg
    450                 455                 460

Val Gly Leu Val Ala Ser Gln Lys Asn Asp Leu Asp Ala Val Ala Leu
465                 470                 475                 480

Met His Pro Asp Gly Ser Ala Val Val Val Val Leu Asn Arg Ser Ser
                485                 490                 495

Lys Asp Val Pro Leu Thr Ile Lys Asp Pro Ala Val Gly Phe Leu Glu
            500                 505                 510

Thr Ile Ser Pro Gly Tyr Ser Ile His Thr Tyr Leu Trp Arg Arg Gln
        515                 520                 525


<210> SEQ ID NO 24
<211> LENGTH: 5
<212> TYPE: PRT
<213> ORGANISM: artificial sequence
<220> FEATURE:
<223> OTHER INFORMATION: Amino acid sequence of a glycine-serine linker

<400> SEQUENCE: 24

Gly Gly Gly Gly Ser
1               5


<210> SEQ ID NO 25
<211> LENGTH: 10
<212> TYPE: PRT
```

<213> ORGANISM: artificial sequence
<220> FEATURE:
<223> OTHER INFORMATION: Amino acid sequence of a two repeats of the glycine-serine linker

<400> SEQUENCE: 25

Gly Gly Gly Gly Ser Gly Gly Gly Gly Ser
1 5 10

<210> SEQ ID NO 26
<211> LENGTH: 17
<212> TYPE: PRT
<213> ORGANISM: artificial sequence
<220> FEATURE:
<223> OTHER INFORMATION: Amino acid sequence of alternative ICAM-1 targeting peptide

<400> SEQUENCE: 26

Asn Asn Gln Lys Ile Val Asn Leu Lys Glu Lys Val Ala Gln Leu Glu
1 5 10 15

Ala

<210> SEQ ID NO 27
<211> LENGTH: 17
<212> TYPE: PRT
<213> ORGANISM: artificial sequence
<220> FEATURE:
<223> OTHER INFORMATION: Amino acid sequence of alternative ICAM-1 targeting peptide

<400> SEQUENCE: 27

Asn Asn Gln Lys Leu Val Asn Ile Lys Glu Lys Val Ala Gln Ile Glu
1 5 10 15

Ala

<210> SEQ ID NO 28
<211> LENGTH: 7
<212> TYPE: PRT
<213> ORGANISM: artificial sequence
<220> FEATURE:
<223> OTHER INFORMATION: Amino acid sequence of alternative ICAM-1 targeting peptide

<400> SEQUENCE: 28

Tyr Pro Ala Ser Tyr Gln Arg
1 5

<210> SEQ ID NO 29
<211> LENGTH: 7
<212> TYPE: PRT
<213> ORGANISM: artificial sequence
<220> FEATURE:
<223> OTHER INFORMATION: Amino acid sequence of alternative ICAM-1 targeting peptide

<400> SEQUENCE: 29

Tyr Gln Ala Thr Pro Leu Pro
1 5

<210> SEQ ID NO 30
<211> LENGTH: 7
<212> TYPE: PRT
<213> ORGANISM: artificial sequence
<220> FEATURE:
<223> OTHER INFORMATION: Amino acid sequence of alternative ICAM-1 targeting peptide

<400> SEQUENCE: 30

Gly Ser Leu Leu Ser Ala Ala
1 5

<210> SEQ ID NO 31
<211> LENGTH: 7
<212> TYPE: PRT
<213> ORGANISM: artificial sequence
<220> FEATURE:
<223> OTHER INFORMATION: Amino acid sequence of alternative ICAM-1 targeting peptide

<400> SEQUENCE: 31

Phe Ser Pro His Ser Arg Thr
1 5

<210> SEQ ID NO 32
<211> LENGTH: 7
<212> TYPE: PRT
<213> ORGANISM: artificial sequence
<220> FEATURE:
<223> OTHER INFORMATION: Amino acid sequence of alternative ICAM-1 targeting peptide

<400> SEQUENCE: 32

Tyr Pro Phe Leu Pro Thr Ala
1 5

<210> SEQ ID NO 33
<211> LENGTH: 7
<212> TYPE: PRT
<213> ORGANISM: artificial sequence
<220> FEATURE:
<223> OTHER INFORMATION: Amino acid sequence of alternative ICAM-1 targeting peptide

<400> SEQUENCE: 33

Gly Cys Lys Leu Cys Ala Gln
1 5

<210> SEQ ID NO 34
<211> LENGTH: 4
<212> TYPE: PRT
<213> ORGANISM: artificial sequence
<220> FEATURE:
<223> OTHER INFORMATION: Amino acid sequence of the first protease cleavage site, recognized by cathepsin L or cathepsin B, in the fusion proteins

<400> SEQUENCE: 34

Gly Phe Leu Gly
1

<210> SEQ ID NO 35
<211> LENGTH: 5
<212> TYPE: PRT
<213> ORGANISM: artificial sequence
<220> FEATURE:
<223> OTHER INFORMATION: Amino acid sequence of the second protease cleavage site, the enterokinase cleavage sequence, in the fusion proteins

<400> SEQUENCE: 35

Asp Asp Asp Asp Lys
1 5

<210> SEQ ID NO 36

```
<211> LENGTH: 6
<212> TYPE: PRT
<213> ORGANISM: artificial sequence
<220> FEATURE:
<223> OTHER INFORMATION: Amino acid sequence of the second protease
      cleavage site, the Tobacco etch virus cleavage sequence, in the
      fusion proteins

<400> SEQUENCE: 36

Glu Asn Leu Tyr Phe Gln
1               5


<210> SEQ ID NO 37
<211> LENGTH: 4
<212> TYPE: PRT
<213> ORGANISM: artificial sequence
<220> FEATURE:
<223> OTHER INFORMATION: Amino acid sequence of the second protease
      cleavage site, the Factor Xa cleavage site, in the fusion proteins

<400> SEQUENCE: 37

Ile Glu Gly Arg
1


<210> SEQ ID NO 38
<211> LENGTH: 5
<212> TYPE: PRT
<213> ORGANISM: artificial sequence
<220> FEATURE:
<223> OTHER INFORMATION: X in position 2 and 3 is any residue, position
      3 is a hydrophobic residue, and the X in position 5 is S or T
<220> FEATURE:
<221> NAME/KEY: misc_feature
<222> LOCATION: (2)..(5)
<223> OTHER INFORMATION: Xaa can be any naturally occurring amino acid

<400> SEQUENCE: 38

Pro Xaa Xaa Xaa Xaa
1               5


<210> SEQ ID NO 39
<211> LENGTH: 9
<212> TYPE: PRT
<213> ORGANISM: artificial sequence
<220> FEATURE:
<223> OTHER INFORMATION: position 5 is a hydrophobic residue position 7
      is any residue but V
<220> FEATURE:
<221> NAME/KEY: misc_feature
<222> LOCATION: (1)..(4)
<223> OTHER INFORMATION: Xaa can be any naturally occurring amino acid
<220> FEATURE:
<221> NAME/KEY: misc_feature
<222> LOCATION: (6)..(9)
<223> OTHER INFORMATION: Xaa can be any naturally occurring amino acid

<400> SEQUENCE: 39

Xaa Xaa Xaa Xaa Arg Xaa Xaa Xaa Xaa
1               5


<210> SEQ ID NO 40
<211> LENGTH: 6
<212> TYPE: PRT
<213> ORGANISM: artificial sequence
<220> FEATURE:
<223> OTHER INFORMATION: Amino acid sequence of the second protease
      cleavage site, the thrombin cleavage site, in the fusion proteins

<400> SEQUENCE: 40

Leu Val Pro Arg Gly Ser
```

-continued

```
1               5


<210> SEQ ID NO 41
<211> LENGTH: 20
<212> TYPE: PRT
<213> ORGANISM: artificial sequence
<220> FEATURE:
<223> OTHER INFORMATION: Amino acid sequence of a secretion signal in
      the fusion protein

<400> SEQUENCE: 41

Met Glu Thr Asp Thr Leu Leu Leu Trp Val Leu Leu Leu Trp Val Pro
1               5                   10                  15

Gly Ser Thr Gly
            20


<210> SEQ ID NO 42
<211> LENGTH: 20
<212> TYPE: PRT
<213> ORGANISM: artificial sequence
<220> FEATURE:
<223> OTHER INFORMATION: Amino acid sequence of a secretion signal in
      the fusion proteins

<400> SEQUENCE: 42

Met Gly Trp Ser Cys Ile Ile Leu Phe Leu Val Ala Thr Ala Thr Gly
1               5                   10                  15

Val His Ser Asp
            20
```

What is claimed is:

1. A fusion protein comprising:

five to ten tandemly connected intercellular adhesion molecule-1 (ICAM-1) targeting segments, wherein each ICAM-1 targeting segment comprises SEQ ID NO: 1 (NNQKIVNIKEKVAQIEA (2γ3));

ii) an enzyme segment that can be catalytically active at the pH of a lysosome, wherein the enzyme segment comprises Acid sphingomyelinase (ASM), Alpha galactosidase, or Glucocerebrosidase;

iii) a first protease cleavage sequence segment between i) and ii), and optionally, one or more of:

iv) a secretion signal;

v) a protein purification tag; and vi) a second protease cleavage sequence.

2. The fusion protein of claim 1, further comprising iv).

3. The fusion protein of claim 2, further comprising v).

4. The fusion protein of claim 2, further comprising vi).

5. The fusion protein of claim 1, wherein the enzyme segment comprises the ASM.

6. The fusion protein of claim 1, wherein the enzyme segment comprises the Alpha galactosidase.

7. The fusion protein of claim 1, wherein the enzyme segment comprises the Glucocerebrosidase.

8. The fusion protein of claim 1, wherein the fusion protein comprises an amino acid sequence having at least 92% sequence identity to SEQ ID NO: 14, SEQ ID NO: 15, SEQ ID NO: 16, SEQ ID NO: 19 or SEQ ID NO: 22.

9. A method comprising administering to an individual in need thereof a therapeutically effective amount of the fusion protein of claim 1.

10. The method of claim 9, wherein the fusion protein further comprises at least iv).

11. The method of claim 10, wherein the individual is in need of treatment for any of Pompe Disease, GM1 gangliosidosis, Tay-Sachs disease, GM2 gangliosidosis, Sandhoff disease, Fabry disease, Gaucher disease, metachromatic leukodystrophy, Krabbe disease, Niemann-Pick disease type A, Niemann-Pick disease type B, Niemann-Pick disease type C, Niemann-Pick disease type D, Farber disease, Wolman disease, Hurler Syndrome, Scheie Syndrome, Hurler-Scheie Syndrome, Hunter Syndrome, Sanfilippo A Syndrome, Sanfilippo B Syndrome, Sanfilippo C Syndrome, Sanfilippo D Syndrome, Morquio A disease, Morquio B disease, Maroteaux-Lamy disease, Sly Syndrome, α-mannosidosis, β-mannosidosis, fucosidosis, aspartylglucosaminuria, sialidosis, mucolipidosis II, mucolipidosis III, mucolipidosis IV, Goldberg Syndrome, Schindler disease, cystinosis, Salla disease, infantile sialic acid storage disease, Batten disease, infantile neuronal ceroid lipofuscinosis, and prosaposin, Parkinson's Disease, or a combination thereof.

12. An expression vector encoding the fusion protein of claim 1.

13. One or more modified cells that are modified to express the fusion protein of claim 1.

* * * * *